(12) United States Patent
Romine et al.

(10) Patent No.: US 6,271,249 B1
(45) Date of Patent: Aug. 7, 2001

(54) DIPHENYL IMIDAZOLES AS POTASSIUM CHANNEL MODULATORS

(75) Inventors: Jeffrey L. Romine, Meriden; Scott W. Martin; Piyasena Hewawasam, both of Middletown; Nicholas A. Meanwell, East Hampton; Valentin K. Gribkoff, Wallingford; John E. Starrett, Jr., Middletown, all of CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/538,520

(22) Filed: Mar. 29, 2000

Related U.S. Application Data

(62) Division of application No. 09/197,887, filed on Nov. 23, 1998, which is a division of application No. 08/902,684, filed on Jul. 30, 1997, now Pat. No. 5,869,509.
(60) Provisional application No. 60/022,983, filed on Jul. 31, 1996.

(51) Int. Cl.[7] .......................... A61K 31/402; A61P 25/08; C07D 233/64
(52) U.S. Cl. ...................... 514/392; 514/235.8; 514/341; 514/392; 514/399; 514/254.05; 514/227.8; 544/139; 544/60; 544/370; 546/274.4; 548/325.5; 548/343.5
(58) Field of Search .................................... 514/399, 392, 514/235.8, 341, 227.8, 254.05; 548/325.5, 343.5; 544/139, 60, 370; 546/274.4

(56) References Cited

U.S. PATENT DOCUMENTS

| 3,971,803 |   | 7/1976 | Rosenberger et al. . |         |
|-----------|---|--------|----------------------|---------|
| 4,450,277 | * | 5/1984 | Graf et al.          | 548/346 |
| 5,116,858 |   | 5/1992 | Hayashi et al. .     |         |
| 5,179,210 | * | 1/1993 | Ebel                 | 548/335.1 |
| 5,331,002 |   | 7/1994 | Miller .             |         |
| 5,436,252 |   | 7/1995 | Sorensen et al. .    |         |
| 5,612,363 | * | 3/1997 | Mohan et al.         | 514/392 |
| 5,869,509 | * | 2/1999 | Romine et al.        | 514/364 |

FOREIGN PATENT DOCUMENTS

| 435 177  | 7/1991 | (EP) . |
| 533 276  | 3/1993 | (EP) . |
| WO 93/08800 | 5/1993 | (WO) . |
| WO 97/17345 | 5/1997 | (WO) . |

OTHER PUBLICATIONS

Ahmed, F. et al., "Some Features of the Spasmogenic Actions of Acetylcholine and Histamine in Guinea–Pig Isolated Trachealis", *Br. J. Pharmacol.*, 83, p. 227–233 (1984).
Baró, I. and Escande, D., "A $Ca^{2+}$–activated $K^+$ Current in Guinea–pig Atrial Myocytes", *Pflügers Archiv.*, 414, (Suppl. 1), p. S168–S–170 (1989).

Cook, N.S., "The Pharmacology of Potassium Channels and Their Therapeutic Potential", *Trends in Pharmacol. Sciences*, 9, p. 21–28 (Jan., 1988).
Koh, D–S., et al., "Effect of the Flavoid Phloretin on $Ca^{2+}$–activated $K^+$ Channels in Myelinated Nerve Fibres of *Xenopus Laevis*", *Neuroscience Lett.* 165, p. 167–170 (1994).
Laurent, F. et al., "Evaluation of the Relaxant Effects of SCA40, A Novel Charybdotoxin–Sensitive Potassium Channel Opener, in Guinea–Pig Trachealis", *Br. J. Pharmacol.*, 108, p. 622–626 (1993).
Quast, U. and Cook, N. S , "Moving Together: $K^+$ Channel Openers and ATP–sensitive $K^+$ Channels", *Trends in Pharmacol. Sciences*, 10, p. 431–435 Nov., 1989).

(List continued on next page.)

*Primary Examiner*—Cecilia Tsang
*Assistant Examiner*—Donna N. Wright
(74) *Attorney, Agent, or Firm*—Aldo A. Algieri

(57) ABSTRACT

Novel compounds of Formula 1 are useful to treat disorders responsive to openers of the large conductance calcium-activated potassium channels:

(1)

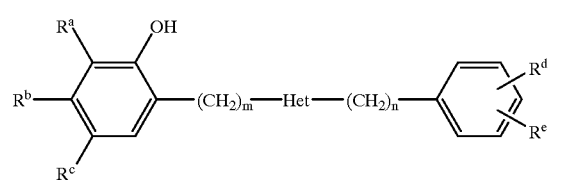

wherein "Het" is one of a select group of heterocyclic moieties; Z is independently for each occurrence selected from O or S; $R^a$, $R^b$ and $R^c$ each are independently selected from hydrogen, halogen, OH, $CF_3$, $NO_2$, or

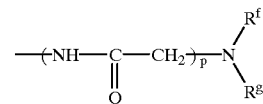

provided $R^c$ is not hydrogen; and when $R^a$ and $R^b$ are hydrogen, $R^c$ may be a heterocyclic moiety selected from the group consisting of imidazol-1-yl, morpholinomethyl, N-methylimidazol-2-yl, and pyridin-2-yl; $R^d$ and $R^e$ each are independently selected from hydrogen, halogen, $CF_3$, $NO_2$ or imidazol-1-yl; m, n and p each are independently selected from an integer of 0 or 1; and $R^f$ and $R^g$ each are independently hydrogen; $C_{1-4}$ alkyl; or $R^f$ and $R^g$, taken together with the nitrogen atom to which they are attached, is a heterocyclic moiety selected from the group consisting of N-methylpiperazine, morpholine, thiomorpholine, N-benzylpiperazine and imidazolinone.

8 Claims, No Drawings

OTHER PUBLICATIONS

Singer, J. J. and Walsh, J.V., "Characterization of Calcium-activated Potassium Channels in Single Smooth Muscle Cells Using the Patch–clamp Technique", *Pflügers Archiv.*, *408*, p. 98–111 (1987).

Trivedi, S., et al., "Calcium Dependent K–Channels In Guinea Pig and Human Urinary Bladder", *Biochemical and Biophysical Research Communications, 213*, No. 2, p. 404–409 (Aug., 1995).

Wilder Smith, A.E., "Preparation of Some New 4–Substituted Derivatives of p–Amino–o–hydroxy–phenyl–1,3, 4–oxadiazolone–5 and Study of their Mycobacteriostatic Activity", *Arzneim. Forsch., 67*, No. 17, p. 768–72 (1967).

* cited by examiner

DIPHENYL IMIDAZOLES AS POTASSIUM CHANNEL MODULATORS

CROSS-REFERENCE TO RELATED APPLICATION

This is a divisional application of co-pending application U.S. Ser. No. 09/197,887, filed Nov. 23, 1998, which is a divisional of U.S. Ser. No. 08/902,684, filed Jul. 30, 1997, now U.S. Pat. No. 5,869,509, which claims the benefit of provisional application U.S. Ser. No. 60/022,983, filed Jul. 31, 1996.

FIELD OF THE INVENTION

The present invention is directed to novel diphenyl heterocyclic derivatives which are modulators of the large-conductance calcium-activated potassium (BK) channels and, therefore, useful in the protection of neuronal cells, especially in the treatment or prevention of ischemic stroke. The present invention is also directed to a method of treatment with the novel compounds and to pharmaceutical compositions containing them.

BACKGROUND OF THE INVENTION

Stroke is presently recognized as the third leading cause of adult disability and death in the United States and Europe. In the past decade, several therapeutic approaches for the minimization of stroke-related brain damage have been pursued including inhibitors of AMPA/kainate, N-methyl-D-aspartate (NMDA) and adenosine reuptake inhibitors. It is the object of the present invention to provide novel compounds that will modulate potassium channels, in particular, large-conductance calcium-activated potassium (BK) channels which will be useful in reducing neuronal damage during ischemic conditions of a stroke episode.

Potassium channels play a key role in regulation of cell membrane potential and modulation of cell excitability. Potassium channels are themselves regulated by voltage, cell metabolism, calcium ion and receptor mediated processes. [Cook, N. S., *Trends in Pharmacol. Sciences* (1988), 9, p. 21–28; and Quast, U. and Cook, N. S., *Trends in Pharmacol. Sciences* (1989), 10, p. 431–435]. Calcium-activated potassium ($K_{Ca}$) channels are a diverse group of ion channels that share a dependence on intracellular calcium ions for activity. The activity of $K_{Ca}$ channels is regulated by intracellular [$Ca^{2+}$], membrane potential and phosphorylation. On the basis of their single-channel conductances in symmetrical $K^+$ solutions, $K_{Ca}$ channels are divided into three subclasses: large conductance (BK)>150 pS; intermediate conductance 50–150 pS; small conductance<50 pS. ("pS" stands for picosiemen, a unit of electrical conductance.) Large-conductance calcium-activated potassium (BK) channels are present in many excitable cells including neurons, cardiac cells and various types of smooth muscle cells. [Singer, J. J. and Walsh, J. V., *Pflügers Archiv.* (1987) 408, p. 98–111; Baró, I., and Escande, D., *Pflügers Archiv.* (1989) 414 (Suppl. 1), p. S168–S170; and Ahmed, F. et al., *Br. J. Pharmacol.* (1984) 83, p. 227–233].

Potassium ions play a dominant role in controlling the resting membrane potential in most excitable cells and in maintaining the transmembrane voltage near the $K^+$ equilibrium potential ($E_k$) of about −90 mV. It has been shown that opening of potassium channels shifts the cell membrane potential towards the equilibrium potassium membrane potential ($E_k$), resulting in hyperpolarization of the cell. [Cook, N. S., *Trends in Pharmacol. Sciences* (1988), 9, p. 21–28]. Hyperpolarized cells show a reduced response to potentially damaging depolarizing stimuli. BK channels which are regulated by both voltage and intracellular $Ca^{2+}$ act to limit depolarization and calcium entry and may be particularly effective in blocking damaging stimuli. Therefore cell hyperpolarization via opening of BK channels may result in protection of neuronal cells under ischemic conditions.

The role of potassium channels in the operation of the smooth muscle of the human urinary bladder is discussed by S. Trivedi, et al. in *Biochemical and Biophysical Research Communications*, (1995), 213, No. 2, p. 404–409.

A range of synthetic and naturally occuring compounds with BK opening activity have been reported. The avena pyrone extracted from avena sativa-common oats has been identified as a BK channel opener using a lipid bi-layer technique [International Patent application WO 93/08800, published May 13, 1993]. 6-Bromo-8-(methylamino) imidazo[1,2-a]pyrazine-2-carbonitrile (SCA-40) has been described as a BK channel opener on the basis of limited electrophysiological experiments [Laurent, F. et al., *Br. J. Pharmacol.* (1993) 108, p. 622–626]. The flavanoid, Phloretin has been found to affect the opening of $Ca^{2+}$-activated potassium channels in myelinated nerve fibers of *Xenopus laevis* using outside-out patches [Koh, D-S., et al., *Neuroscience Lett.* (1994) 165, p.167–170].

EPO 0-435177-A2 published on Jul. 3, 1991, discloses substituted triazolones of Formula (i)

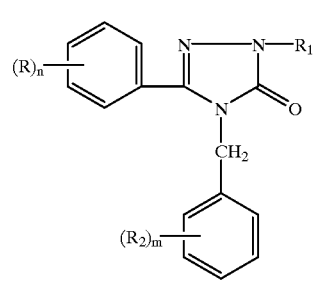

(i)

wherein

R and $R_2$ are $C_{1-4}$ alkyl, $C_{1-4}$ alkoxy, halogen, or trifluoromethyl and $(R_2)_m$ is methylenedioxy;

$R_1$ is hydrogen or $C_{1-4}$ alkyl; and m and n are 0, 1 or 2.

These compounds are anticonvulsants. Note that, in Formula (i) compounds, R cannot be hydroxyl.

U.S. Pat. No. 5,331,002 issued to J. A. Miller on Jul. 19, 1994, discloses compounds of Formula ii:

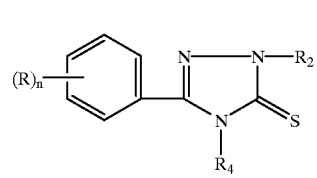

(ii)

wherein

R is halogen, trifluoromethyl, $C_{1-4}$ alkyl or $C_{1-4}$ alkoxy;

n=0, 1 or 2;

$R_2$ is hydrogen or $C_{1-3}$ alkyl; and $R_4$ is $C_{1-3}$ alkyl.

These Formula ii compounds are memory enhancers. Note that the hetero rings bear only one substituted phenyl moiety in structure ii.

U.S. Pat. No. 3,971,803 issued to S. Rosenberger and K. Schwarzenbach on Jul. 27, 1976, relates to compounds of Formula iii:

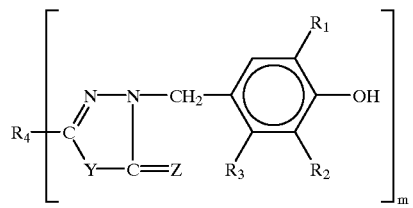

(iii)

wherein $R_1$ is alkyl, cycloalkyl or aralkyl;

$R_2$ is hydrogen or $R_1$;

$R_3$ is hydrogen or $C_{1-4}$ alkyl;

Y and Z are independently O or S;

$R_4$ is either (1), if m=1, $C_{1-8}$ alkylene, —$C_xH_{2x}$—Q—$C_yH_{2y}$— (Q is O or S, x and y are integers whose sum is 2 to 4), phenylene, diphenylene or naphthalene or a

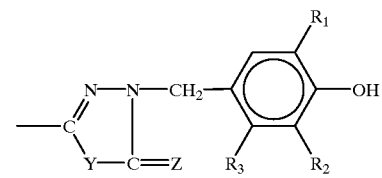

group;

or (2) if m=2, alkylene, alkylene ether, alkylene thioether, diphenylene, or napthalene. The compounds are antioxidants for organic polymers.

EPO 0-533276-A1 published on Mar. 24, 1993, shows compounds of Formula iv:

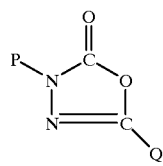

(iv)

wherein one of P or Q is an ortho-substituted phenyl group and the other a substituted benzyl. The Formula iv compounds are miticides and insecticides.

U.S. Pat. No. 5,116,858 issued to Y. Hayashi, et al. on May 26, 1992, discusses 4-imidazolone compounds which have activity as lipid peroxidase inhibitors. They may be of Formula v:

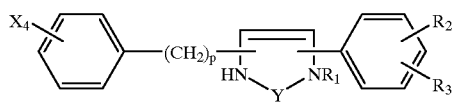

(v)

wherein $X_4$ is H, halogen, alkyl or alkoxy, p is 1 to 3, Y is

or =C(OH)—, $R_1$ is (cyclo)alkyl, alkenyl, or aralkyl and $R_2$ and $R_3$ are H or a variety of hydrocarbon, or hydrocarbon-oxy groups.

A. E. Wilder Smith disclosed in *Arzneim. Forsch.* (1967) 67, No. 17, p. 768–772, the preparation and study of compounds of Formula vi:

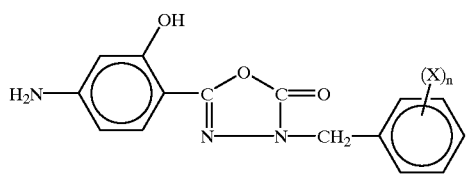

(vi)

wherein X is H or Cl and n is 1 or 2. The compounds have tuberculostatic properties. Formula vi compounds do not encompass substitution para to the hydroxyl group.

U.S. Pat. No. 5,436,252 issued to S. M. Sorensen, et al., on Jul. 25, 1995, describes the treatment of neurodegenerative disorders using 5-aryl-3H-1,2,4-triazol-3-ones of Formula vii:

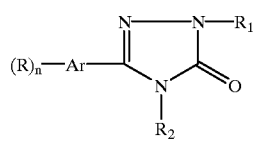

(vii)

wherein Ar is individually phenyl, naphthyl or an aromatic heterocyclic group, $R_1$ is hydrogen or lower alkyl, $R_2$ is lower alkyl, R is individually alkyl, alkoxy, hydroxy, halogen or trifluoromethyl, n is 0–2 or $(R)_n$—Ar together is methylenedioxyphenyl. Formula vii does not encompass diphenyl compounds.

None of these discloses all of the compounds of the invention or their use as potassium channel modulators.

SUMMARY OF THE INVENTION

The present invention provides novel diphenyl heterocyclic derivatives having the general formula (1)

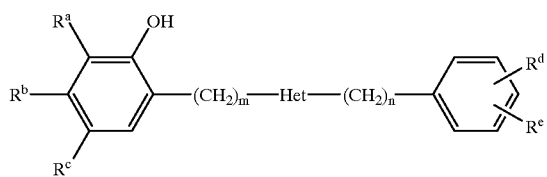

wherein "Het" is a moiety selected from the group consisting of (A) through (H):

(A)

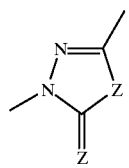

(B)

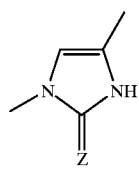

(C)

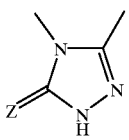

(D)

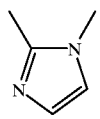

(E)

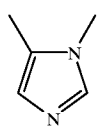

(F)

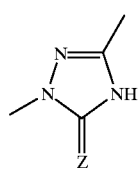

(G)

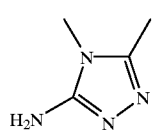

(H)

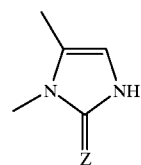

wherein Z is independently for each occurrence selected from O or S; $R^a$, $R^b$ and $R^c$ each are independently selected from hydrogen, halogen, OH, $CF_3$, $NO_2$, or

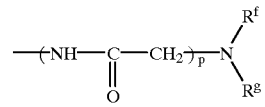

provided $R^c$ is not hydrogen; and when $R^a$ and $R^b$ are hydrogen, $R^c$ may be a heterocyclic moiety selected from the group consisting of imidazol-1-yl, morpholinomethyl, N-methylimidazol-2-yl, and pyridin-2-yl; $R^d$ and $R^e$ each are independently selected from hydrogen, halogen, $CF_3$, $NO_2$ or imidazol-1-yl; m, n and p each are independently selected from an integer of 0 or 1; and $R^f$ and $R^g$ each are independently hydrogen; $C_{1-4}$ alkyl; or $R^f$ and $R^g$, taken together with the nitrogen atom to which they are attached, is a heterocyclic moiety selected from the group consisting of N-methylpiperazine, morpholine, thiomorpholine, N-benzylpiperazine and imidazolinone.

Nontoxic pharmaceutically acceptable salts, solvates or hydrates of Formula 1 compounds are also covered by this invention. The invention provides these compounds as well as compositions and methods which employ them.

DETAILED DESCRIPTION OF THE INVENTION

The present invention provides novel diphenyl heterocyclic derivatives which are potent openers of the high conductance, calcium-activated $K^+$-channels (BK channel) and which have Formula 1

(1)

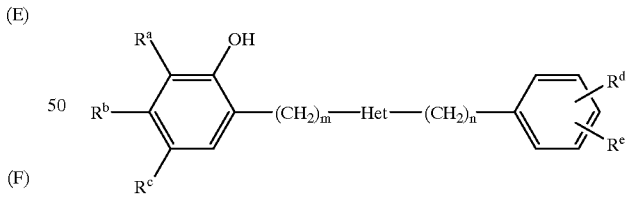

wherein "Het" is a moiety selected from the group consisting of (A) through (H):

(A)

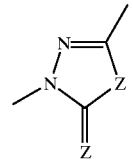

-continued (B)
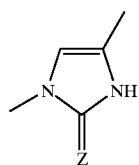

(C)
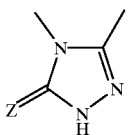

(D)
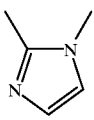

(E)
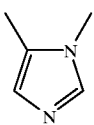

(F)
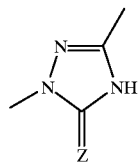

(G)
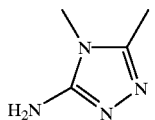

(H)
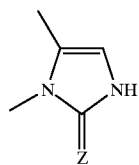

wherein Z is independently for each occurrence selected from O or S; $R^a$, $R^b$ and $R^c$ each are independently selected from hydrogen, halogen, OH, $CF_3$, $NO_2$, or

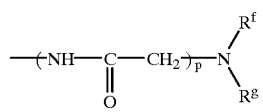

provided $R^c$ is not hydrogen; and when $R^a$ and $R^b$ are hydrogen, $R^c$ may be a heterocyclic moiety selected from the group consisting of imidazol-1-yl, morpholinomethyl, N-methylimidazol-2-yl, and pyridin-2-yl; $R^d$ and $R^e$ each are independently selected from hydrogen, halogen, $CF_3$, $NO_2$ or imidazol-1-yl; m, n and p each are independently selected from an integer of 0 or 1; and $R^f$ and $R^g$ each are independently hydrogen; $C_{1-4}$ alkyl; or $R^f$ and $R^g$, taken together with the nitrogen atom to which they are attached, is a heterocyclic moiety selected from the group consisting of N-methylpiperazine, morpholine, thiomorpholine, N-benzylpiperazine and imidazolinone.

The present invention also provides a method for the treatment of or protection from disorders which are mediated by opening of the large conductance calcium-activated $K^+$ channels (BK channels) in a mammal in need thereof, which comprises administering to said mammal a therapeutically effective amount of a compound of Formula 1 or a nontoxic pharmaceutically acceptable salt thereof. Preferably, the compounds of Formula 1 are useful in the treatment of ischemia, convulsions, asthma, irritable bowel syndrome, migraine, traumatic brain injury, male erectile dysfunction, and urinary incontinence and other disorders sensitive to BK channel activating activity.

The term "Z" as used herein and in the claims is independently selected from O or S. It is to be understood that when Z is oxygen the O atom may be part of an ether link (C—O—C) or a carbonyl (C=O) group; and when Z is sulfur, the S atom may be part of a thioether (C—S—C) or thiocarbonyl (C=S) moiety.

Optical isomers and other isomers of heterocyclic moieties (A) through (H) are useful, as are all isomers of Formula 1 compounds in general. Prodrugs and other forms can be employed.

The term "$C_{1-4}$ alkyl" as used herein and in the claims (unless the context indicates otherwise) means straight or branched chain alkyl groups such as methyl, ethyl, propyl, isopropyl, butyl, isobutyl, t-butyl, Preferably, these groups contain from 1 to 2 carbon atoms. Unless otherwise specified, the term "halogen" as used herein and in the claims is intended to include bromine, chlorine, iodine and fluorine while the term "halide" is intended to include bromine, chloride and iodide anion.

The term "Het" as used herein and in the claims (unless the context indicates otherwise) is intended to include all the heterocyclic moieties defined by the Formulas (A) through (H) in which each heterocyclic moiety is disubstituted and attached as indicated by the two bonds shown in the structural formulas. Furthermore, it is to be understood that attachment of the phenyl groups can be either, for example, 4,5- or 5,4-disubstituted; 3,5 or 5,3-disubstituted; 1,5 or 5,1-disubstituted and other isomers of the "Het" moieties (A) through (H).

The term "nontoxic pharmaceutically acceptable salt" as used herein and in the claims is intended to include nontoxic acid and base addition salts. Suitable acids include sulfuric, phosphoric, hydrochloric, hydrobromic, hydroiodic, citric, acetic, benzoic, cinnamic, fumaric, mandelic, phosphoric, nitric, mucic, isethionic, palmitic, heptanoic, and the like. Suitable inorganic bases, such as alkali and alkaline earth metal bases, include metallic cations such as sodium, potassium, magnesium, calcium and the like.

Generally, pharmaceutically acceptable salts of the invention are those in which the counter-ion does not contribute significantly to the toxicity or pharmacological activity of the salt. In some instances, they have physical properties which make them more desirable for pharmaceutical formulations, such as solubility, lack of hygroscopicity, compressibility with respect to tablet formation and compatibility with other ingredients with which the substance may be used for pharmaceutical purposes. The salts are routinely made by admixture of a Formula 1 compound with the selected acid or base, preferably by contact in solution employing an excess of commonly used inert solvents such as water, ether, benzene, methanol, ethanol, ethyl acetate and acetonitrile. They may also be made by metathesis or treatment with an ion exchange resin under conditions in which the appropriate ion of a salt of the substance of the Formula 1 is replaced by another ion under conditions which allow for separation of the desired species such as by precipitation from solution or extraction into a solvent, or elution from or retention on an ion exchange resin.

Certain compounds of the present invention can exist as solvated forms including hydrated forms such as monohydrate, dihydrate, hemihydrate, trihydrate, tetrahydrate and the like. The products may be true solvates, while in other cases, the products may merely retain adventitious solvent or be a mixture of solvate plus some adventitious solvent. It should be appreciated by those skilled in the art that solvated forms are equivalent to unsolvated forms and are intended to be encompassed within the scope of the present invention.

In the method of the present invention, the term "therapeutically effective amount" means the total amount of each active component of the composition that is sufficient to show a meaningful patient benefit, i.e., healing of acute conditions characterized by openers of large conductance calcium-activated $K^+$ channels or increase in the rate of healing of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing or ameliorating diseases, tissue damage and/or symptoms associated with dysfunction of cellular membrane polarization and conductance.

The compounds of Formula 1 may be prepared by various procedures such as those illustrated herein in the examples, in the Reaction Schemes and variations thereof which would be evident to those skilled in the art.

1,2-Diarylheterocycles

The triazolones of type I and II were prepared as outlined in Reaction Schemes 1 and 2. For instance, phenylacetic acid or benzoic acids (where n=0) were activated as their acid chlorides and coupled with an aniline. The resultant amides III and IV were treated with phosphorus pentachloride in benzene at reflux and intermediate iminoyl chlorides trapped with anhydrous hydrazine to give amidrazones V and VI, respectively. Cyclization of the amidrazones by treatment with carbonyldiimidazole in THF gave the triazolone ring system. Demethylation was accomplished upon heating the triazolones at 225° C. in the presence of pyridine hydrochloride and the phenols I and II were isolated in good overall yields (~45–55%).

Reaction Schemes 3–5 depict the preparation of several related ring-systems. The triazolothione VII was prepared from amidrazone V upon treatment with 1,1'-thiocarbonyldiimidazole in THF, followed by demethylation with pyridinium hydrochloride (Reaction Scheme 3). Condensing the same amidrazone V with cyanogen bromide in the presence of sodium bicarbonate lead to the amino triazole VIII after demethylation of the more sensitive amino triazole was performed with boron tribromide in cold (0° C.) methylene chloride.

REACTION SCHEME 1

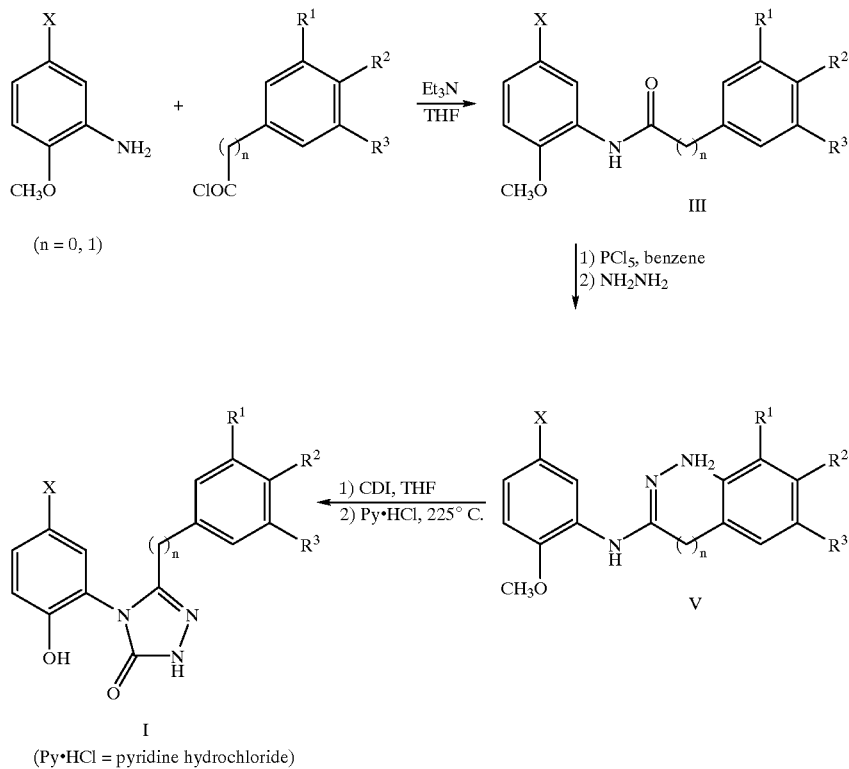

(Py•HCl = pyridine hydrochloride)

REACTION SCHEME 2
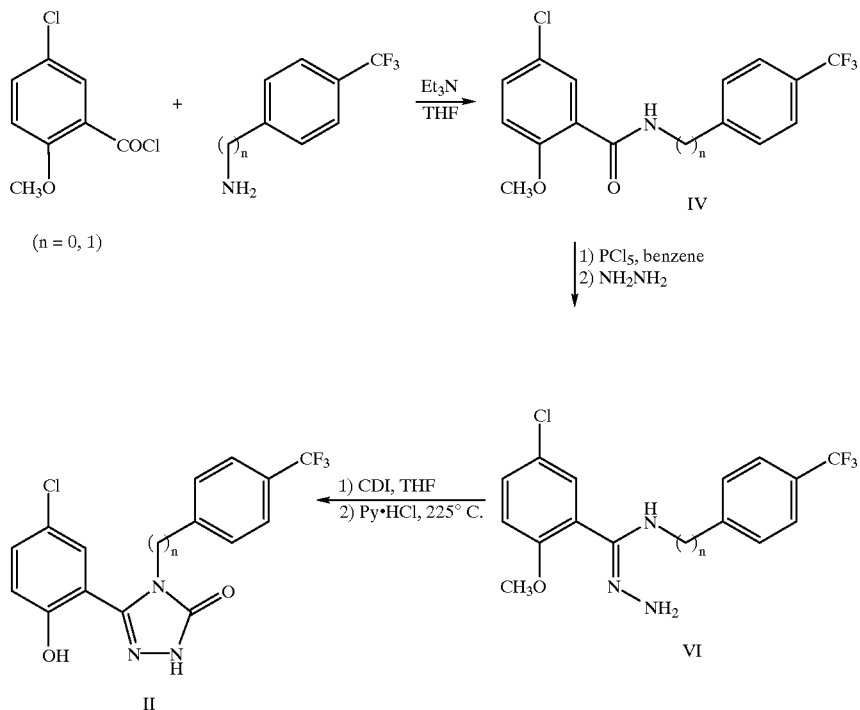
REACTION SCHEME 3
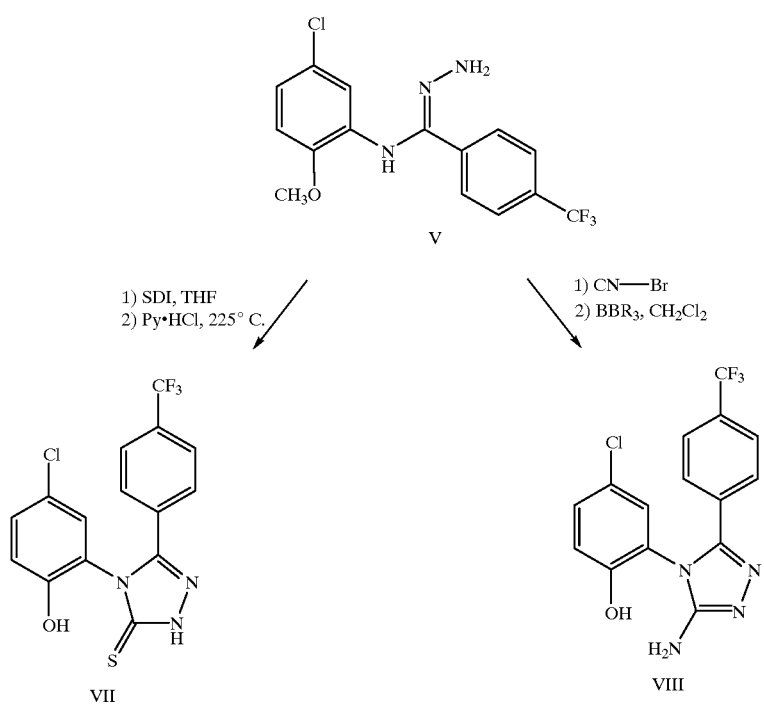

REACTION SCHEME 4

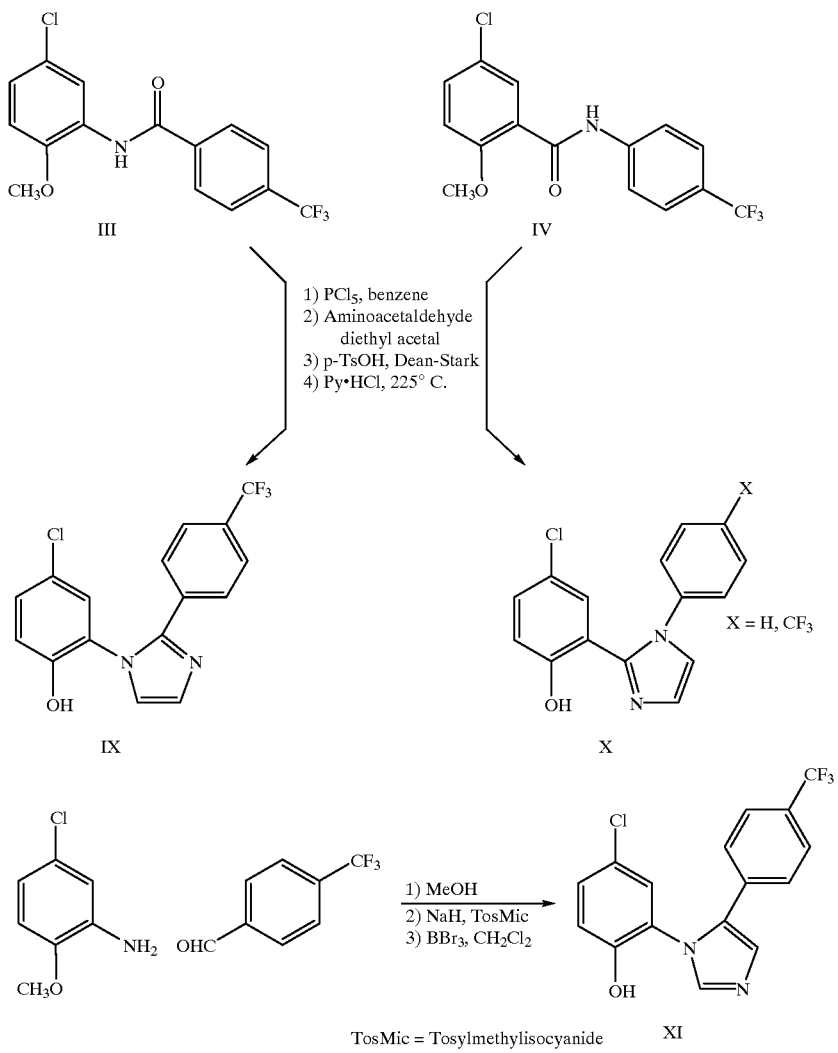

Imidazoles, as illustrated in Reaction Scheme 4, were obtained when the intermediate iminoyl chlorides III and IV were trapped with aminoacetaldehyde diethyl acetal. Heating the acetals at reflux in benzene under Dean-Stark conditions caused cyclization to the imidazole rings which underwent demethylation with pyridinium hydrochloride to afford systems IX and X. A third imidazole XI was prepared upon condensation of an aniline with 5-chloro-2-methoxybenzaldehyde. The intermediate imine was treated with tosylmethylisocyanide under basic conditions to generate imidazole IX after demethylation with BBr$_3$.

REACTION SCHEME 5

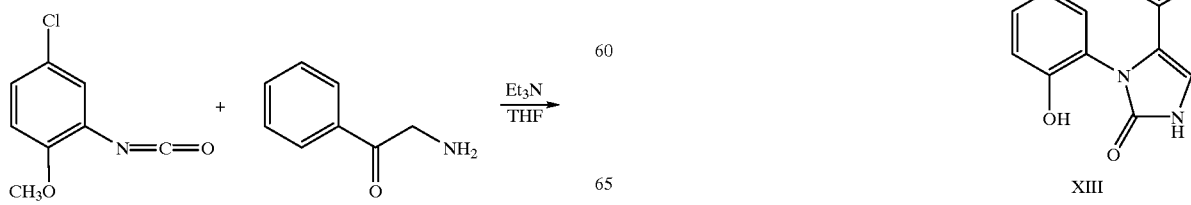

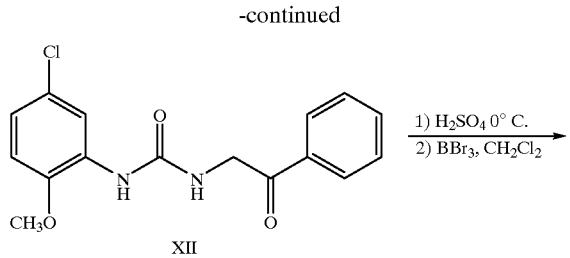

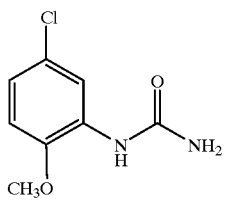

+

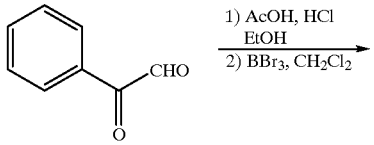

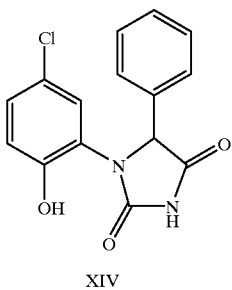

XIV

Addition of 2-aminoacetophenone to 5-chloro-2-methoxyisocyanate as outlined in Reaction Scheme 5 gave a 2-oxophenethylurea XII which upon dissolution in concentrated sulfuric acid at 0° C. cyclized, and after demethylation with boron tribromide, provided imidazolone XIII. An imidazolinedione derivative XIV was obtained upon condensation of N-(5-chloro-2-methoxyphenyl)urea with phenylglyoxal followed by demethylation upon exposure to boron tribromide.

1-Aryl-3-benzylheterocycles

The synthesis of 1-aryl-3-benzylheterocycles is described in Reaction Schemes 6 and 8–10. Oxadiazolones prepared according to literature methods were alkylated with benzyl bromides in the presence of potassium carbonate in acetonitrile at reflux. A second method, alkylation of oxadiazolones with benzyl alcohols under Mitsunobu conditions, was also employed to secure the same products. When Y=H, boron tribromide mediated demethylation gave product XV. For analogs wherein Y=NHAc, the methylether derivatives were hydrolyzed in 10% HCl/ethanol at reflux to give anilines, and demethylation gave products of structure XVI.

A further analog, chloro derivative XVII, was prepared upon demethylation and selective chlorination with sulfuryl chloride in the presence of catalytic diisobutylamine prior to acetate hydrolysis.

REACTION SCHEME 6

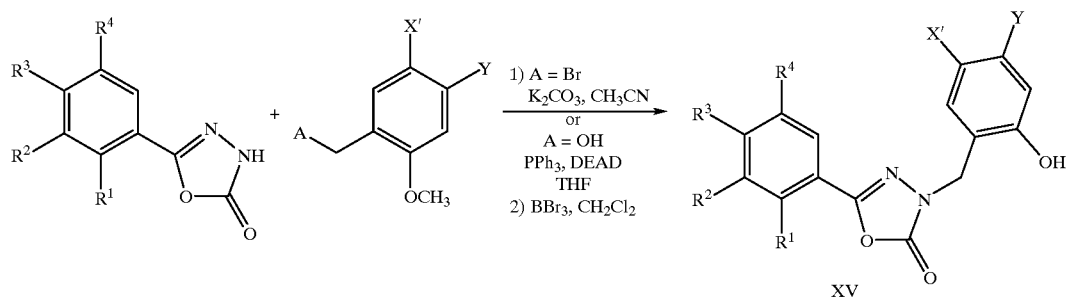

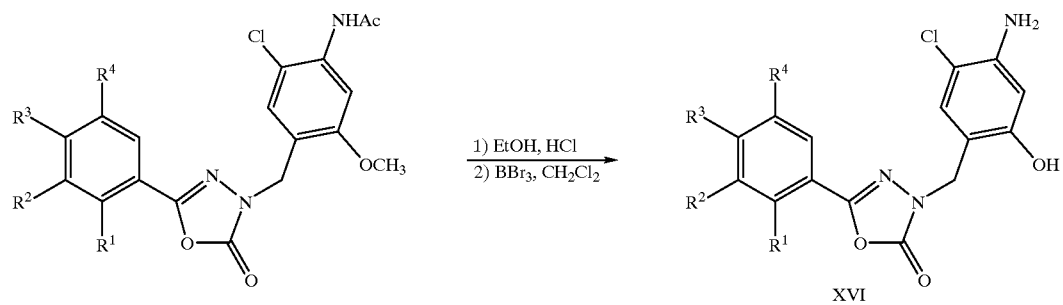

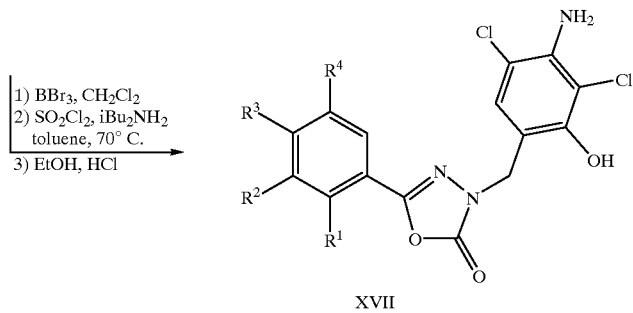

XVII

X'=chloro, 2-pyridinyl, 1-imidazole, 1-methyl-2-imidazole, or 4-morpholinylmethyl and Y=ethylmethylamino or hydrogen.

In several analogs (i.e., when X'=2-pyridinyl, 1-imidazole, 1-methyl-2-imidazole, ethylmethylamino, or 4-morpholinylmethyl) the precursor benzyl alcohols for the Mitsunobu reaction were not commercially available. The preparation of these compounds is illustrated in Reaction Scheme 7.

Reaction Scheme 7

In all the compounds, the benzyl alcohols were prepared through reduction of either an aldehyde or ester. The aryl rings were functionalized either through coupling methods or alkylation.

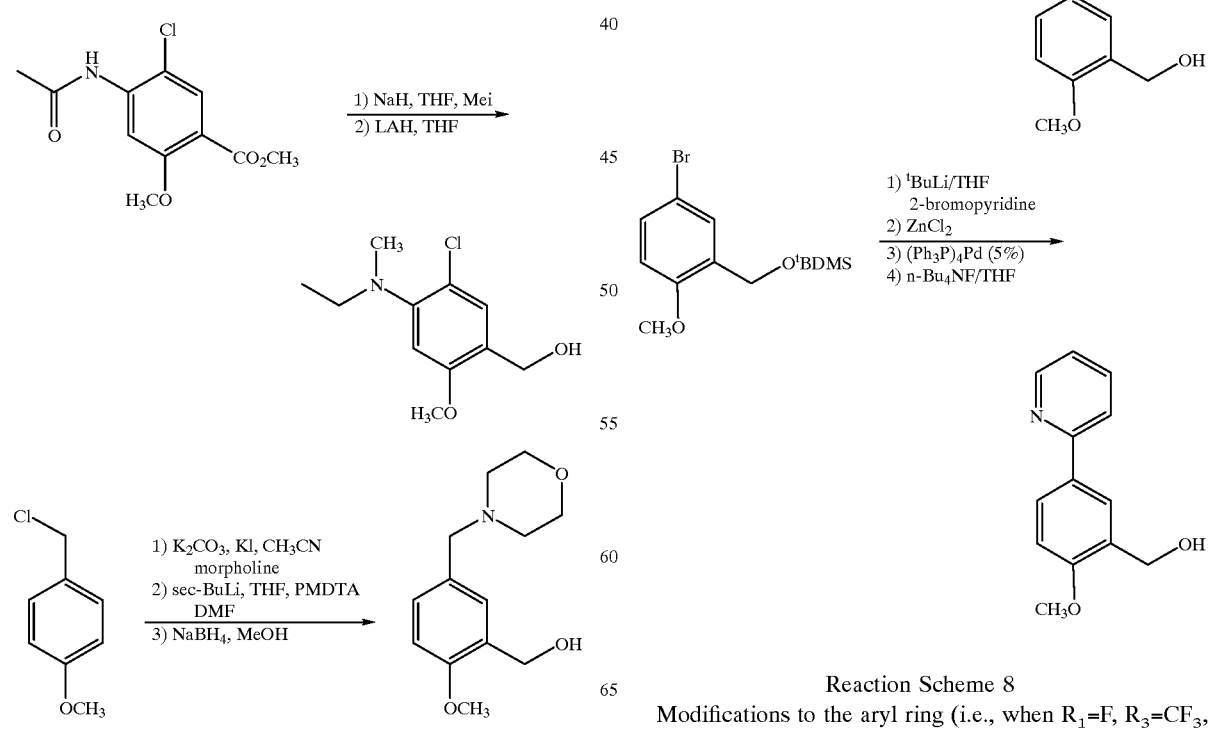

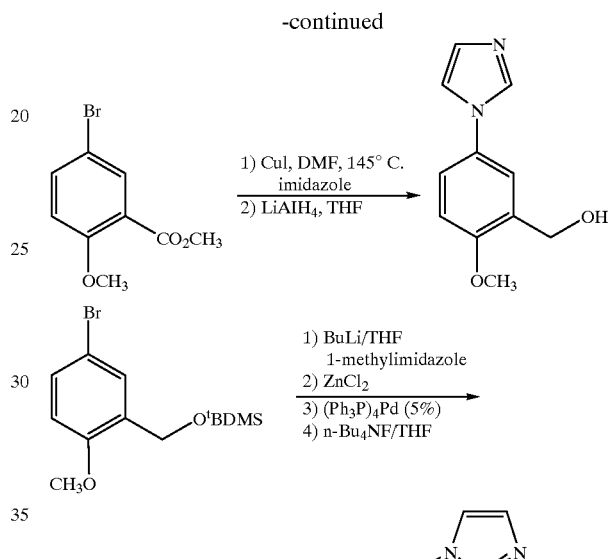

Reaction Scheme 8

Modifications to the aryl ring (i.e., when $R_1$=F, $R_3$=CF$_3$, and $R_3$=F, $R_4$=CF$_3$) were affected by ipso substitution of the fluorine with imidazole to give XVIII after demethylation with pyridine hydrochloride (Reaction Scheme 8).

In one example, the oxadiazolone ring system reacted smoothly with Lawesson's reagent to give the thione analog XIX after demethylation with boron tribromide.

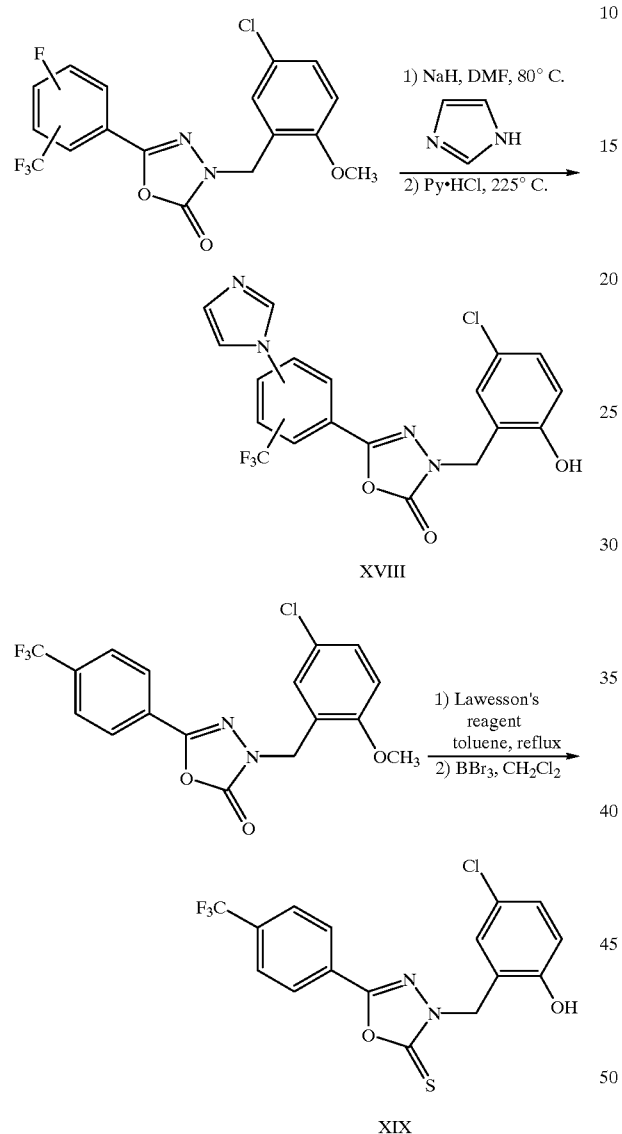

REACTION SCHEME 9

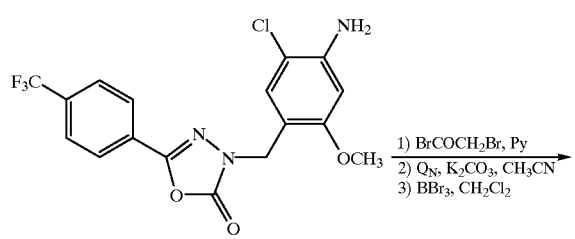

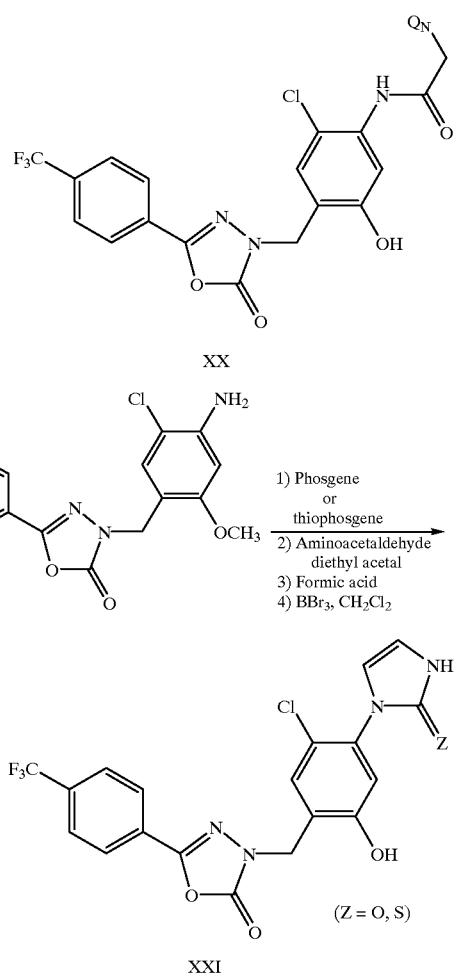

Reaction Scheme 9 outlines the modification of an aniline to several derivatives upon treatment with bromoacetyl bromide and subsequent alkylation (with $Q_N$=morpholine, thiomorpholine, N-methyl piperazine, N-phenyl piperazine, N-benzyl piperazine, dimethylamine) to give product XX after demethylation.

Alternatively, conversion of the same aniline to an isocyanate, or isothiocyanate, and addition of aminoacetaldehyde diethyl acetal and cyclization afforded imidazolone (thione) XXI.

REACTION SCHEME 10

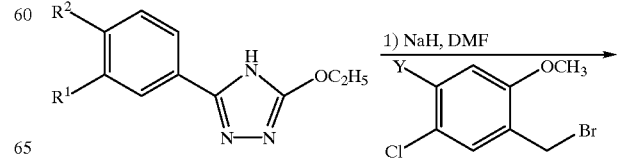

21
-continued

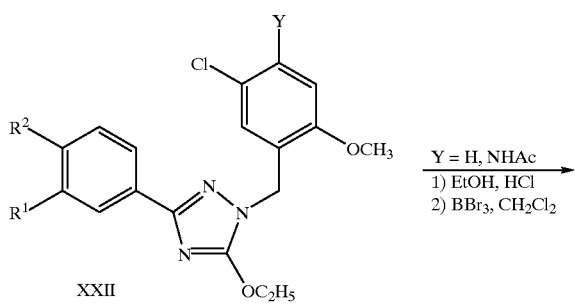

XXII

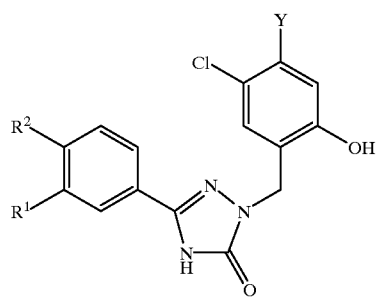

XXIII (Y = H or NH₂)

Triazolone products were prepared as outlined in Reaction Scheme 10. Alkylation of an ethoxy triazole in sodium hydride DMF gave products XXII and a regioisomer (not shown) as a mixture (1:1). The products were purified by silica gel chromatography and the ethoxy triazole subjected to hydrolysis in 10% HCl/ethanol in order to afford the triazolone ring system. Hydrolysis of the acetate also occurred under these conditions (Y=NHAc), and demethylation with boron tribromide gave triazolone products of Formula XXIII.

1,3-Diarylheterocycles

REACTION SCHEME 11

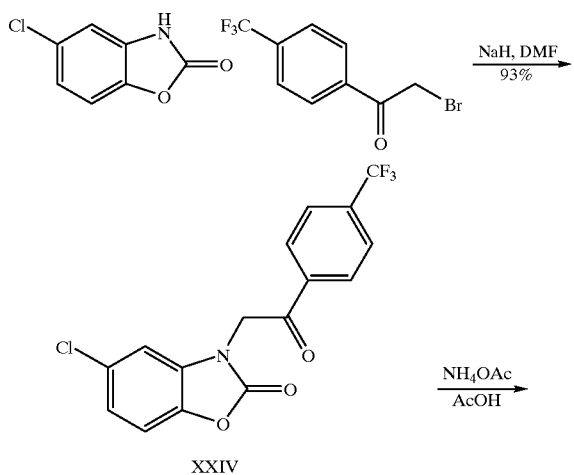

XXIV

22
-continued

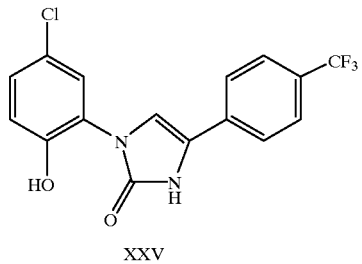

XXV

Alkylation of chloroxazone with α'-bromo-4-(trifluoromethyl)-acetophenone in sodium hydride/DMF gave the benzoxazolone XXIV in good yield (Reaction Scheme 11). Further treatment with ammonium acetate at reflux in acetic acid caused rearrangement to imidazolone product XXV.

REACTION SCHEME 12

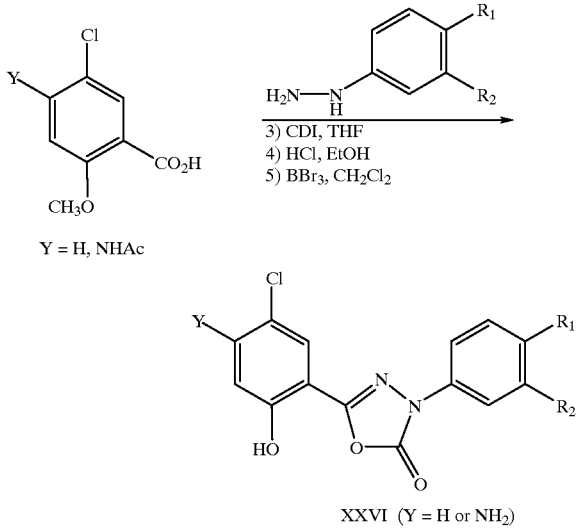

XXVI (Y = H or NH₂)

Oxadiazolone XXVI, illustrated in Reaction Scheme 12, was prepared upon acylation of a phenyldhydrazine with activated benzoic acids. Cyclization of the resultant hydrazide with carbonyidiimidazole gave the oxadiazolone ring system, and hydrolysis (as above when Y=NHAc) prior to demethylation with boron tribromide gave XXVI.

REACTION SCHEME 13

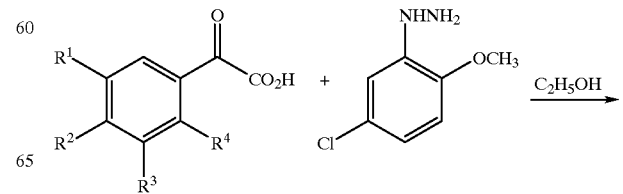

-continued

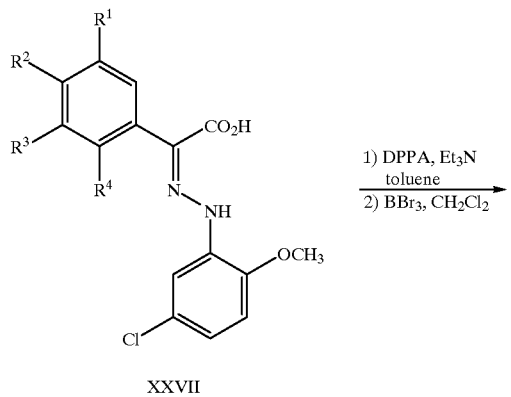

XXVII

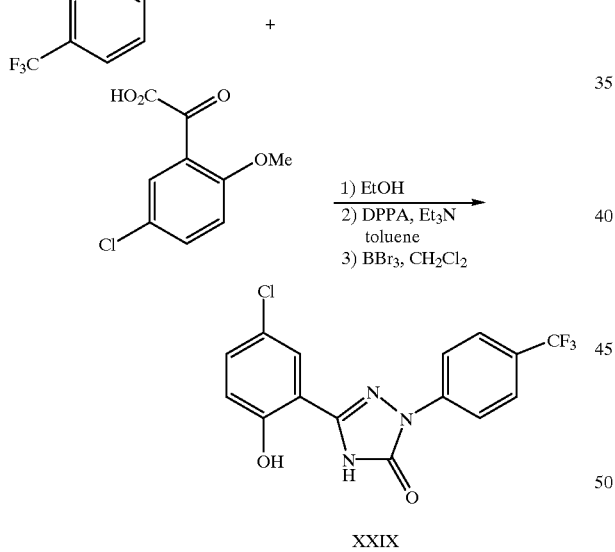

XXVIII

REACTION SCHEME 14

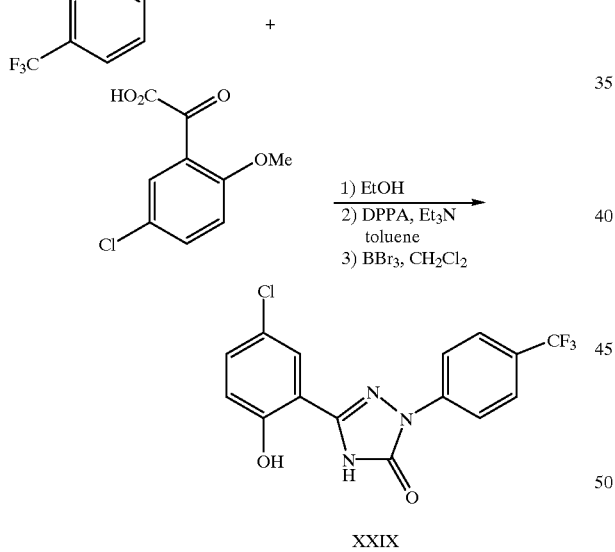

XXIX

A series of triazolones was prepared as depicted in Reaction Scheme 13. Condensation of glyoxalic acids with phenylhydrazines in refluxing ethanol gave carboxylic acids XXVII. Exposure to diphenylphosphorylazide generated isocyanates which were trapped intramolecularly to give triazolones XXVIII after demethylation with boron tribromide. The regioisomeric triazolone XXIX was prepared in a similar manner by reversing the substitution pattern of the hydrazine and glyoxalic acid starting materials as shown in Reaction Scheme 14.

In one preferred embodiment of the invention, the compounds are of Formula (1a) or Formula (1b)

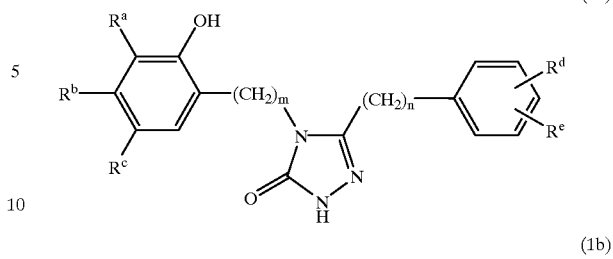

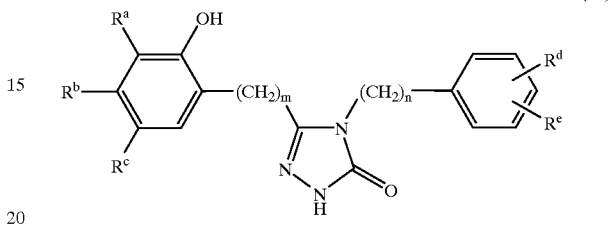

wherein $R^a$ through $R^e$ are as defined above. In preferred compounds of Formula (1a) or Formula (1b), $R^a$ and $R^b$ are H, OH, $NH_2$ or Cl; $R^c$ is Cl; $R^d$ and $R^e$ are $CF_3$ or H; with m=0 and n=0 or 1.

In another preferred embodiment of the invention the compounds are of Formula (1c)

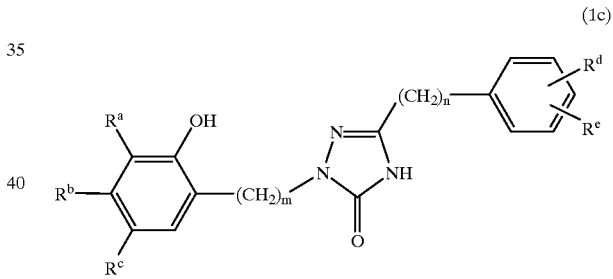

wherein $R^a$ through $R^e$ are as defined above. In preferred Formula 1c compounds, $R^a$ and $R^b$ are OH, H, $NH_2$ or Cl; $R^c$ is Cl; $R^d$ and $R^e$ are H, $CF_3$ or Cl; with m=0 or 1 and n=0.

In yet another preferred embodiment, the compounds of the invention conform to Formula (1d) or Formula (1e)

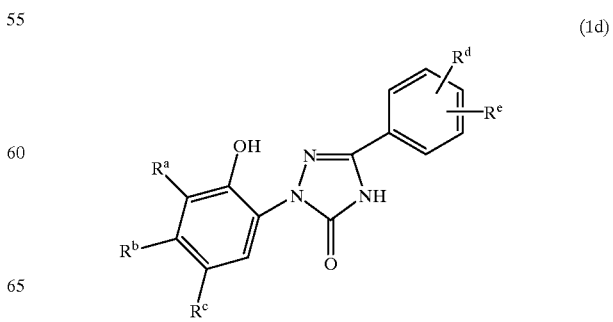

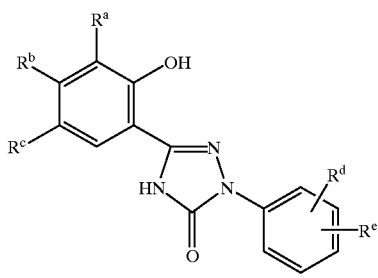

(1e)

wherein $R^a$ and $R^b$ are hydrogen, hydroxyl, chloro or $NH_2$; $R^c$ is chloro; $R^d$ and $R^e$ are hydrogen, trifluoromethyl, fluoro or chloro. It is generally preferred that at least one of $R^d$ and $R^e$ be trifluoromethyl or chloro.

In still another preferred embodiment of the invention the compounds have Formula (1f)

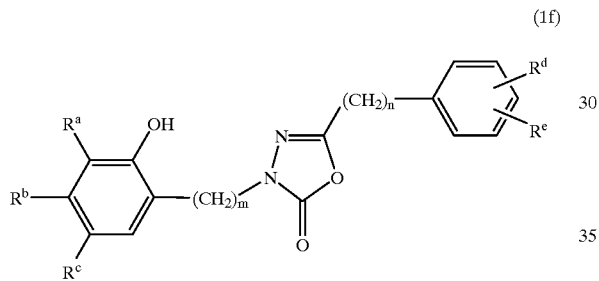

(1f)

$R^a$, $R^b$ and $R^c$ each are independently selected from hydrogen, halogen, OH, $CF_3$, $NO_2$, or

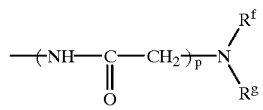

provided $R^c$ is not hydrogen; and when $R^a$ and $R^b$ are hydrogen, $R^c$ may be a heterocyclic moiety selected from the group consisting of imidazol-1-yl, morpholinomethyl, N-methylimidazol-2-yl, and pyridin-2-yl; $R^d$ and $R^e$ each are independently selected from hydrogen, halogen, $CF_3$, $NO_2$ or imidazol-1-yl; m, n and p each are independently selected from an integer of 0 or 1; and $R^f$ and $R^g$ each are independently hydrogen; $C_{1-4}$ alkyl; or $R^f$ and $R^g$, taken together with the nitrogen atom to which they are attached, is a heterocyclic moiety selected from the group consisting of N-methylpiperazine, morpholine, thiomorpholine, N-benzylpiperazine and imidazolinone.

In yet another preferred embodiment, the compounds of the invention conform to Formula (1g)

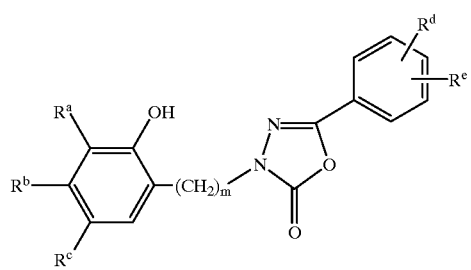

(1g)

wherein $R^a$ and $R^b$ are H, OH, Cl, or $NH_2$; $R^c$ is chloro; $R^d$ and $R^e$ are H, $CF_3$ or Cl; with m=1. It is generally preferred that at least one of $R^d$ and $R^e$ be $CF_3$ or Cl in the (1g) compounds.

In still another preferred embodiment, the compounds of the invention conform to Formula (1h)

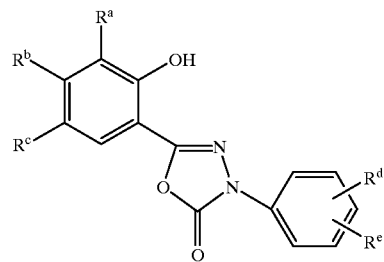

(1h)

wherein $R^a$ and $R^b$ are hydrogen, hydroxyl, chloro or $NH_2$; $R^c$ is chloro; $R^d$ and $R^e$ are hydrogen, trifluomethyl or chloro. It is generally preferred that at least one of $R^d$ and $R^e$ be $CF_3$ or Cl in the Formula (1h) compounds.

Preferred compounds include:
  4-(5-Chloro-2-hydroxyphenyl)-5-[3,5-bis(trifluoromethyl)phenyl]-2,4-dihydro-3H-1,2,4-triazol-3-one;
  4-(5-Chloro-2-hydroxyphenyl)-5-[4-(trifluoromethyl)phenyl]-2,4-dihydro-3H-1,2,4-triazol-3-one;
  4-(5-Chloro-2-hydroxyphenyl)-5-[3-(trifluoromethyl)phenyl]-2,4-dihydro-3H-1,2,4-triazol-3-one;
  4-(5-Chloro-2-hydroxyphenyl)-5-(4-fluorophenyl)-2,4-dihydro-3H-1,2,4-triazol-3-one;
  4-[2-Hydroxy-5-(trifluoromethyl)phenyl]-5-[4-(trifluoromethyl)phenyl]-2,4-dihydro-4-3H-1,2,4-triazol-3-one;
  4-(5-Chloro-2-hydroxyphenyl)-5-[[(trifluoromethyl)phenyl]methyl]-2,4-dihydro-3H-1,2,4-triazol-3-one;
  4-(5-Chloro-2-hydroxyphenyl)-5-[4-(trifluoromethyl)phenyl]-2,4-dihydro-3H-1,2,4-triazol-3-thione;
  4-Chloro-2-[2-[4-(trifluoromethyl)phenyl]-1H-imidazol-1-yl]phenol;
  5-(5-Chloro-2-hydroxyphenyl)-4-[4-(trifluoromethyl)phenyl]-2,4-dihydro-3H-1,2,4-triazol-3-one;
  5-(5-Chloro-2-hydroxyphenyl)-4-[[4-(trifluoromethyl)phenyl]methyl]-2,4-dihydro-3H-1,2,4-triazol-3-one;
  4-Chloro-2-[1-[4-(trifluoromethyl)phenyl]-1H-imidazol-2-yl]phenol;
  4-Chloro-2-[1-phenyl-1H-imidazol-2-yl]phenol;
  4-Chloro-2-[3-amino[5-[4-(trifluoromethyl)phenyl]-4H-1,2,4-triazol-4-yl]]phenol;

1-(5-Chloro-2-hydroxyphenyl)-5-[4-(trifluoromethyl) phenyl]-1H-imidazole;

1-(5-Chloro-2-hydroxyphenyl)-1,3-dihydro-5-phenyl-2H-imidazol-2-one;

3-[(4-Amino-5-chloro-2-hydroxyphenyl)methyl]-5-[3,4-dichlorophenyl]-1,3,4-oxadiazol-2(3H)-one;

3-[[4-(Amino)-5-chloro-2-hydroxyphenyl]methyl]-5-[3,5-dichlorophenyl]-1,3,4-oxadiazol-2(3H)-one;

3-[(4-Amino-5-chloro-2-hydroxyphenyl)methyl]-5-[4-(trifluoromethyl)-phenyl]-1,3,4-oxadiazol-2(3H)-one;

3-[2-Hydroxyphenyl)methyl]-5-[4-(trifluoromethyl) phenyl]-1,3,4-oxadiazol-2(3H)-one;

3-[(5-Chloro-2-hydroxyphenyl)methyl]-5-[4-(trifluoromethyl)phenyl]-1,3,4-oxadiazol-2(3H)-one;

3-[[2-Hydroxy-5-chlorophenyl]methyl]-5-[3,5-bis(trifluoromethyl)phenyl]-1,3,4-oxadiazol-2(3H)-one;

3-[(5-Chloro-2-hydroxyphenyl)methyl]-5-[4-fluoro-3-(trifluoromethyl)-phenyl]-1,3,4-oxadiazol-2(3H)-one 3-[[2-Hydroxy-5-chlorophenyl]methyl]-5-[2-chloro-5-(trifluoromethyl)-phenyl]-1,3,4-oxadiazol-2(3H)-one;

3-[[2-Hydroxy-5-chlorophenyl]methyl]-5-[3,5-dichlorophenyl]-1,3,4-oxadiazol-2(3H)-one;

3-[(5-Chloro-2-hydroxyphenyl)methyl]-5-[2-fluoro-4-(trifluoromethyl)-phenyl]1,3,4-oxadiazol-2(3H)-one;

3-[(4-Amino-3,5-dichloro-2-hydroxyphenyl)methyl]-5-[3,4-dichlorophenyl]1,3,4-oxadiazol-2(3H)-one;

3-[(5-Chloro-2-hydroxyphenyl)methyl]-5-[2-(1H-imidazol-1-yl)-4-(trifluoro-methyl)phenyl]-1,3,4-oxadiazol-2(3H)-one;

3-[(5-Chloro-2-hydroxyphenyl)methyl]-5-[4-(1H-imidazol-1-yl)-3-(trifluoro-methyl)phenyl]-1,3,4-oxadiazol-2(3H)-one;

3-[[2-Hydroxy-5-(4-morpholinylmethyl)phenyl]methyl]-5-[4-trifluoromethyl)phenyl]-1,3,4-oxadiazol-2(3H)-one;

3-[5-Chloro-4-[(ethylmethylamino)-2-hydroxyphenyl] methyl]-5-[4-trifluoromethyl)phenyl]-1,3,4-oxadiazl-2(3H)-one;

3-[[2-Hydroxy-5-(2-pyridinyl)phenyl]methyl]-5-[4-(trifluoromethyl)phenyl]-1,3,4-oxadiazol-2(3H)-one;

3-[[5-(1-Methyl-1H-imidazol-2-yl)-2-hydroxyphenyl] methyl]-5-[4-(trifluoromethyl)phenyl]-1,3,4-oxadiazol-2(3H)-one;

3-[[2-hydroxy-5-(1-methyl-1H-imidazo-2-yl)phenyl] methyl]-5-[3,5-bis(trifluoromethyl)phenyl]-1,3,4-oxadiazol-2(3H)-one;

3-[[2-Hydroxy-5-(1H-imidazol-1-yl)phenyl]methyl]-5-[4-(trifluoromethyl)-phenyl]-1,3,4-oxadiazol-2(3H)-one;

3-[[2-Hydroxy-5-(1H-imidazol-1-yl)phenyl]methyl]-5-[3,5-bis(trifluoromethyl)phenyl]-1,3,4-oxadiazol-2 (3H)-one;

N-[2-Chloro-4-[[1,5-dihydro-5-oxo-3-[4-(trifluoromethyl)phenyl]-1,2,4-oxadiazol-1-yl] methyl]-5-hydroxyphenyl]-4-morpholineacetamide;

N-[2-Chloro-4-[[2,3-dihydro-2-oxo-5-[4-(trifluoromethyl)phenyl]-1,3,4-oxadiazol-3-yl] methyl]-5-hydroxyphenyl]-4-thiomorpholineacetamide;

N-[2-Chloro-4-[[2,3-dihydro-2-oxo-5-[4-(trifluoromethyl)phenyl]-1,3,4-oxadiazol-3-yl] methyl]-5-hydroxyphenyl]-4-methyl-1-piperazineacetamide;

N-[2-Chloro-4-[[2,3-dihydro-2-oxo-5-[4-(trifluoromethyl)phenyl]-1,3,4-oxadiazol-3-yl] methyl]-5-hydroxyphenyl]-4-phenyl-1-piperazineacetamide;

N-[2-Chloro-4-[[2,3-dihydro-2-oxo-5-[4-(trifluoromethyl)phenyl]-1,3,4-oxadiazol-3-yl] methyl]-5-hydroxyphenyl]-4-benzyl-1-piperazineacetamide;

N-[2-Chloro-4-[[2,3-dihydro-2-oxo-5-[4-(trifluoromethyl)phenyl]-1,3,4-oxadiazol-3-yl] methyl]-5-hydroxyphenyl]-2-(dimethylamino) acetamide;

N-[2-Chloro-4-[[2,3-dihydro-2-oxo-5-(1,1'-Biphenyl)-1,3,4-oxadiazol-3-yl]methyl]-5-hydroxyphenyl]-4-methyl-1-piperazineacetamide;

N-[2-Chloro-4-[[2,3-dihydro-2-oxo-5-[naphth-2-yl]-1,3,4-oxadiazol-3-yl]methyl]-5-hydroxyphenyl]-4-morpholineacetamide;

3-[(5-Chloro-2-hydroxyphenyl)methyl]-5-[4-(trifluoromethyl)phenyl]-1,3,4-oxadiazol-2(3H)-thione;

3-[[5-Chloro-4-(2,3-dihydro-2-oxo-1H-imidazol-1-yl)-2-hydroxyphenyl]-methyl]-5-[4-(trifluoromethyl)phenyl]-1,3,4-oxadiazol-2(3H)-one;

3-[[5-Chloro-4-(2,3-dihydro-2-thio-1H-imidazol-1-yl)-2-hydroxyphenyl]-methyl]-5-[4-(trifluoromethyl)phenyl-1,3,4-oxadiazol-2(3H)-one;

2-[(4-Amino-5-chloro-2-hydroxyphenyl)methyl]-2,4-dihydro-5-[4-(trifluoromethyl)phenyl]-3H-1,2,4-triazol-3-one;

2-[(4-Amino-5-chloro-2-hydroxyphenyl)methyl]-2,4-dihydro-5-[3,4-dichlorophenyl]-3H-1,2,4-triazol-3-one;

2-[(5-Chloro-2-hydroxyphenyl)methyl]-2,4-dihydro-5-[4-(trifluoromethyl)-phenyl]-3H-1,2,4-triazol-3-one;

5-(4-Amino-5-chloro-2-hydroxyphenyl)-3-[4-(trifluoromethyl)phenyl]-1,3,4-oxadiazole-2-(3H)-one;

5-(4-Amino-5-chloro-2-hydroxyphenyl)-3-phenyl-1,3,4-oxadiazole-2-(3H)-one;

5-(5-Chloro-2-hydroxyphenyl)-3-[4-(trifluoromethyl) phenyl]-1,3,4-oxadiazol-2(3H)-one;

5-(4-Amino-5-chloro-2-hydroxyphenyl)-3-[3,4-dichlorophenyl]-1,3,4-oxadiazole-2-(3H)-one;

1-(5-Chloro-2-hydroxyphenyl)-3-[4-(trifluoromethyl) phenyl]-1,2,4(4H)-triazol-5-one;

1-(5-Chloro-2-hydroxyphenyl)-3-[3-(trifluoromethyl) phenyl]-1,2,4(4H)-triazol-5-one;

1-(5-Chloro-2-hydroxyphenyl)-3-[2-(trifluoromethyl) phenyl]-1,2,4(4H)-triazol-5-one;

1-(5-Chloro-2-hydroxyphenyl)-3-[3,5-bis(trifluoromethyl)phenyl]-1,2,4(4H)-triazol-5-one;

1-(5-Chloro-2-hydroxyphenyl)-3-[2,4-bis(trifluoromethyl) phenyl]-1,2,4(4H)-triazol-5-one;

1-(5-Chloro-2-hydroxyphenyl)-3-[3-chloro-4-(trifluoromethyl)phenyl]-1,2,4(4H)-triazol-5-one; and 5-[5-Chloro-2-hydroxyphenyl]-2,4-dihydro-2-[4-(trifluoromethyl)phenyl]-1,2,4(3H)-triazol-3-one.

In another aspect, this invention provides a method for the treatment of or protection from disorders which are mediated by opening of the large conductance calcium-activated $K^+$ channels (BK channels) in a mammal in need thereof, which comprises administering to said mammal a therapeutically effective amount of a compound of Formula 1 or a nontoxic pharmaceutically acceptable salt, solvate or hydrate thereof. Preferably, the compounds of Formula 1 are useful in the treatment of ischemia, convulsions, asthma, irritable bowel syndrome, migraine, traumatic brain injury, male erectile dysfuntion, and urinary incontinence and other disorders sensitive to BK channel activating activity. Most preferably, the compounds of Formula 1 are useful in the treatment of cerebral ischemia.

In still another aspect, this invention provides pharmaceutical compositions comprising at least one compound of Formula 1 in combination with a pharmaceutical adjuvant, carrier or diluent.

Biological Activity

Potassium (K$^+$) channels are structurally and functionally diverse families of K$^+$-selective channel proteins which are ubiquitous in cells, indicating their central importance in regulating a number of key cell functions [Rudy, B., *Neuroscience*, 25:729–749 (1988)]. While widely distributed as a class, K$^+$ channels are differentially distributed as individual members of this class or as families. [Gehlert, D. R., et al., *Neuroscience*, 52:191–205 (1993)]. In general, activation of K$^+$ channels in cells, and particularly in excitable cells such as neurons and muscle cells, leads to hyperpolarization of the cell membrane, or in the case of depolarized cells, to repolarization. In addition to acting as an endogenous membrane voltage clamp, K$^+$ channels can respond to important cellular events such as changes in the intracellular concentration of ATP or the intracellular concentration of calcium (Ca$^{2+}$). The central role of K$^+$ channels in regulating numerous cell functions makes them particularly important targets for therapeutic development. [Cook, N. S., Potassium channels: Structure, classification, function and therapeutic potential. Ellis Horwood, Chinchester (1990)]. One class of K$^+$ channels, the large-conductance Ca$^{2+}$-activated K$^+$ channels (BK or BK channels), is regulated by transmembrane voltage, intracellular Ca$^{2+}$, and a variety of other factors such as the phosphorylation state of the channel protein. [Latorre, R., et al., *Ann. Rev. Physiol.*, 51:385–399 (1989)]. The large, single channel-conductance (generally>150 pS) and high degree of specificity for K$^+$ of BK channels indicates that small numbers of channels could profoundly affect membrane conductance and cell excitability. Additionally, the increase in open probability with increasing intracellular Ca$^{2+}$ indicates involvement of BK channels in the modulation of Ca$^{2+}$-dependent phenomena such as secretion and muscular contraction. [Asano, M., et al., *J. Pharmacol. Exp. Ther.*, 267:1277–1285 (1993)].

Openers of BK exert their cellular effects by increasing the open probability of these channels [McKay, M. C., et al., *J. Neurophysiol.*, 71:1873–1882 (1994); and Olesen, S.-P., *Exp. Opin. Invest. Drugs*, 3:1181–1188 (1994)]. This increase in the opening of individual BK channels collectively results in the hyperpolarization of cell membranes, particularly in depolarized cells, produced by significant increases in whole-cell BK-mediated conductance.

The ability of compounds described in the present invention to open BK channels and increase whole-cell outward (K$^+$) BK-mediated currents was assessed under voltage-clamp conditions by determining their ability to increase cloned mammalian (mSlo or hSlo) BK—mediated outward current heterologously expressed in Xenopus oocytes [Butler, A., et al., *Science*, 261:221–224 (1993); and Dworetzky, S. I., et al., *Mol. Brain Res.*, 27:189–193 (1994)]. The two BK constructs employed represent nearly structurally identical homologous proteins, and have proven to be pharmacologically identical in our tests. To isolate BK current from native (background, non-BK) current, the specific and potent BK channel-blocking toxin iberiotoxin (IBTX) [Galvez, A., et al., *J. Biol. Chem*, 265:11083–11090 (1990)] was employed at a supramaximal concentration (50 nM). The relative contribution of BK channels current to total outward current was determined by subtraction of the current remaining in the presence of IBTX (non-BK current) from the current profiles obtained in all other experimental conditions (control, drug, and wash). It was determined that at the tested concentration the compounds profiled did not effect non-BK native currents in the oocytes. All compounds were tested in at least 5 oocytes and are reported at concentrations of either 1, 5 or 20 μM; the effect of the selected compounds of Formula 1 on BK current was expressed as the percent of control IBTX-sensitive current and is listed in Table I. Recordings were accomplished using standard two-electrode voltage clamp techniques [Stuhmer, W., et al., *Methods in Enzymology*, Vol. 207:319–339 (1992)]; voltage-clamp protocols consisted of 500–750 ms duration step depolarizations from a holding potential of −60 mV to +140 mV in 20 mV steps. The experimental media (modified Barth's solution) consisted of (in mM): NaCl (88), NaHCO3 (2.4), KCl (1.0), HEPES (10), MgSO4 (0.82), Ca(NO3)2 (0.33), CaCl2 (0.41); pH 7.5.

TABLE I

Effect of Selected Compounds on BK Channels

| Example No. | Increase in BK Current‡ |
|---|---|
| 25 | ++ |
| 78 | +++ |
| 79 | +++ |
| 82 | ++** |
| 99 | ++ |
| 101 | ++ |
| 118 | ++ |
| 119 | + |
| 131 | ++* |
| 140 | +++ |
| 142 | ++ |
| 143 | ++ |
| 144 | +++ |

‡Unless otherwise noted, concentration of test compound = 20 μM; expressed as percent of increase over BK current in controls;
*Concentration = 2.5 μM
**Concentration = 1 μM
+ = 100–125%
++ = 125–175%
+++ = >175%

To determine the ability of these compounds to reduce cell loss resulting from neuronal ischemia, a standard rodent model of permanent focal ischemia, involving occlusion of the middle cerebral artery in the spontaneously hypertensive rat (MCAO model) was employed [Tamura, A., et al., *Journal of Cerebral Blood Flow and Metabolism*, Volume 1, 53–60, (1981)].

Selected compounds have been evaluated in the focal stroke model involving permanent middle cerebral artery occlusion (MCAO) in the spontaneously hypertensive rat. This procedure results in a reliably large neocortical infarct volume that is measured by means of vital dye exclusion in serial slices through the brain 24 hours after MCAO. In the present test, compounds were administered using an i.v. or i.p. route of administration at two hours after occlusion. For example, in this model, the compound of Example 82 significantly reduced the cortical infarct volume by about 14% when administered intraparitoneally (10 mg/kg) as a single bolus 2 hours after middle cerebral artery occlusion as compared to vehicle-treated (2% DMSO, 98% PG) control.

The results of the above in vitro and in vivo tests demonstrate that the compounds of the instant invention are potent openers of the large-conductance calcium-activated $K^+$ channels (BK channels). Thus, the compounds of the present invention are useful for the treatment of human disorders arising from dysfunction of cellular membrane polarization and conductance and, preferably, are indicated for the treatment of ischemia, convulsions, asthma, irritable bowel syndrome, migraine, traumatic brain injury, male erectile dysfunction, and urinary incontinence and other disorders sensitive to BK channel activating activity. Most preferably, the compounds of Formula 1 are useful in the treatment of cerebral ischemia.

Therefore, the compounds of Formula 1 or pharmaceutical compositions thereof are useful in the treatment, alleviation or elimination of disorders or other disorders associated with the BK channels. Such disorders include ischemia, convulsions, asthma, irritable bowel syndrome, migraine, traumatic brain injury, male erectile dysfunction, and urinary incontinence and other disorders sensitive to potassium channel openers.

In another embodiment, this invention includes pharmaceutical compositions comprising at least one compound of Formula 1 in combination with a pharmaceutical adjuvant, carrier or diluent.

In still another embodiment, this invention relates to a method of treatment or prevention of disorders responsive to opening of potassium channels in a mammal in need thereof, which comprises administering to said mammal a therapeutically effective amount of a compound of Formula 1 or a nontoxic pharmaceutically acceptable salt, solvate or hydrate thereof.

In yet another embodiment, this invention relates to a method for treating an ischemic condition in a mammal in need thereof, which comprises administering to said mammal a therapeutically effective amount of a compound of Formula 1 or a non-toxic pharmaceutically acceptable salt, solvate or hydrate thereof.

For therapeutic use, the pharmacologically active compounds of Formula 1 will normally be administered as a pharmaceutical composition comprising as the (or an) essential active ingredient at least one such compound in association with a solid or liquid pharmaceutically acceptable carrier and, optionally, with pharmaceutically acceptable adjuvants and excipients employing standard and conventional techniques.

The pharmaceutical compositions include suitable dosage forms for oral, parenteral (including subcutaneous, intramuscular, intradermal and intravenous) bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. Particularly useful is the administration of a compound of Formula 1 directly in parenteral formulations. The pharmaceutical compositions are prepared by conventional techniques appropriate to the desired preparation containing appropriate amounts of the active ingredient, that is, the compound of Formula 1 according to the invention. See, for example, *Remington's Pharmaceutical Sciences*, Mack Publishing Company, Easton, Pa., 17th edition, 1985.

The dosage of the compounds of Formula 1 to achieve a therapeutic effect will depend not only on such factors as the age, weight and sex of the patient and mode of administration, but also on the degree of potassium channel activating activity desired and the potency of the particular compound being utilized for the particular disorder of disease concerned. It is also contemplated that the treatment and dosage of the particular compound may be administered in unit dosage form and that the unit dosage form would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention to produce the desired therapeutic effect.

A suitable dose of a compound of Formula 1 or pharmaceutical composition thereof for a mammal, including man, suffering from, or likely to suffer from any condition as described herein is an amount of active ingredient from about 0.1 µg/kg to 100 mg/kg body weight. For parenteral administration, the dose may be in the range of 1 µg/kg to 100 mg/kg body weight for intravenous administration. The active ingredient will preferably be administered either continuously or in equal doses from one to four times a day. However, usually a small dosage is administered, and the dosage is gradually increased until the optimal dosage for the host under treatment is determined.

However, it will be understood that the amount of the compound actually administered will be determined by a physician, in the light of the relevant circumstances, including the condition to be treated, the choice of compound of be administered, the chosen route of administration, the age, weight, and response of the individual patient, and the severity of the patient's symptoms.

The following examples are given by way of illustration and are not to be construed as limiting the invention in any way inasmuch as many variations of the invention are possible within the spirit of the invention.

DESCRIPTION OF SPECIFIC EMBODIMENTS

In the following examples, all temperatures are given in degrees Centigrade. Melting points were recorded on a Gallenkamp capillary melting point apparatus temperatures are uncorrected. Proton magnetic resonance ($^1$H NMR) was recorded on a Bruker AC 300. All spectra were determined in the solvents indicated and chemical shifts are reported in δ units downfield from the internal standard tetramethylsilane (TMS) and interproton coupling constants are reported in Hertz (Hz). Splitting patterns are designated as follows: s, singlet; d, doublet; t, triplet; q, quartet; m, multiplet; br, broad peak; dd, doublet of doublet; bd, broad doublet; dt, doublet of triplet; bs, broad singlet; dq, doublet of quartet. Infrared (IR) spectra using potassium bromide (KBr) were determined on a Perkin Elmer 781 spectrometer from 4000 cm$^{-1}$ to 400 cm$^{-1}$, calibrated to 1601 cm$^{-1}$ absorption of a polystyrene film and reported in reciprocal centimeters (cm$^{-1}$). Low resolution mass spectra (MS) and the apparent molecular (MH$^+$) or (M-H)$^-$ was determined on a Finnigen TSQ 7000. High resolution mass spectra was determined on a Kratos MS50 in FAB mode using cesium iodide/glycerol as internal reference. The element analysis are reported as percent by weight.

The following preparations illustrate procedures for the preparation of intermediates and methods for the preparation of products according to this invention. It should also be evident to those skilled in the art that appropriate substitution of both the materials and methods disclosed herein will produce the examples illustrated below and those encompassed by the scope of this invention.

Preparation No. 1

EXAMPLES 1–6

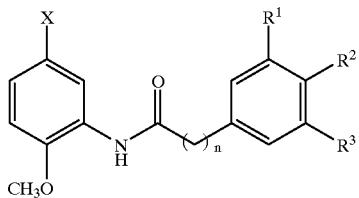

III$^{1-6}$

EXAMPLE 1

N-(5-Chloro-2-methoxyphenyl)-3,5-bis(trifluoromethyl)benzamide (III$^1$: X=Cl, n=0, R$_1$=R$_3$=CF$_3$, R$_2$=H)

5-Chloroansidine (5.6 g, 36.3 mmol) was dissolved in THF (350 mL) and solution of 3,5-bis(trifluoromethyl)benzoyl chloride (10.1 g, 36.6 mmol), dissolved in THF (85 ml), was added dropwise under N$_2$ at 0° C. followed by addition of triethylamine (5.3 mL, 1.7 mmol). The solution was stirred 18 h at 24° C. and filtered to remove Et$_3$N.HCl. Concentration by rotary evaporation removed the solvent and gave a white solid 13.08 g (90%). Recrystallized from ethanol/water (2:1) gave colorless needles mp 151–153° C.; IR(KBr, υ=cm$^{-1}$) 3298, 1654, 1534, 1292, 1276, 1188, 1136, 804; $^1$H NMR (300 MHz, DMSO-d$_6$) δ 3.83 (3H, s), 7.13 (1H, d, J=8.9 Hz), 7.26 (1 H, dd, J=8.8 Hz, 2.7 Hz), 7.76 (1 H, d, J=2.6 Hz), 8.33 (1H, br.s), 8.56 (2H, br.s), 10.25 (1H, br.s); MS(DCl)m/z: 398(MH$^+$). Anal. calcd. for C$_{16}$H$_{10}$ClF$_6$NO$_2$: C,48.32; H, 2.54; N, 3.52. Found: C, 48.35; H, 2.57; N, 3.49.

The following amides were prepared in a similar manner to Example 1.

EXAMPLE 2

N-(5-Chloro-2-methoxyphenyl)-4-(trifluoromethyl)benzamide (III$^2$: X=Cl, n=0, R$_1$=R$_3$=H, R$_2$=CF$_3$)

mp 113–115° C.; Anal. calcd. for C$_{15}$H$_{11}$ClF$_3$NO$_2$.0.1 H$_2$O: C, 54.34; H, 3.41; N, 4.23. Found: C, 54.37; H, 3.34; N, 4.18.

EXAMPLE 3

N-(5-Chloro-2-methoxyphenyl)-3-(trifluoromethyl)benzamide (III$^3$: X=Cl, n=0, R$_1$=CF$_3$, R$_2$=R$_3$=H)

mp 111–112.5° C.; Anal. calcd. for C$_{15}$H$_{11}$ClF$_3$NO$_2$: C, 54.65; H, 3.36; N, 4.25. Found: C, 54.62; H, 3.33; N, 4.19.

EXAMPLE 4

N-(5-Chloro-2-methoxyphenyl)-4-fluorobenzamide (III$^4$: X=Cl, n=0, R$_1$=R$_3$=H, R$_2$=F)

mp 131.5–134° C.; Anal. calcd. for C$_{14}$H$_{11}$ClFNO$_2$.0.05 H$_2$O: C, 59.93; H, 3.99; N, 4.99. Found: C, 59.86; H, 3.97; N, 4.97.

EXAMPLE 5

N-(2-Methoxy-5-trifluoromethylphenyl)-4-trifluoromethyl-benzamide (III$^5$: X=CF$_3$, n=0, R$_1$=R$_3$=H, R$_2$=CF$_3$)

mp 132–133° C.; Anal. calcd. for C$_{16}$H$_{11}$F$_6$NO$_2$: C, 52.90; H, 3.05; N, 3.86. Found: C, 52.78; H, 3.04; N, 3.87.

EXAMPLE 6

N-(5-Chloro-2-methoxyphenyl)-4-(trifluoromethyl)benzeneacetamide (III$^6$: X=Cl, n=1, R$_1$=R$_3$=H, R$_2$=CF$_3$)

mp 115–116° C.; Anal. calcd. for C$_{16}$H$_{13}$ClF$_3$NO$_2$.0.1 H$_2$O: C, 55.63; H, 3.85; N, 4.06. Found: C, 55.86; H, 3.72; N, 3.98.

EXAMPLES 7 AND 8

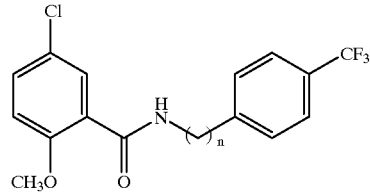

IV$^{7-8}$

EXAMPLE 7

5-Chloro-2-methoxy-N-[4-(trifluoromethyl)phenyl]benzamide (IV$^7$: n=0)

mp 131.5–132.5° C.; Anal. calcd. for C$_{15}$H$_{11}$ClF$_3$NO$_2$.0.01 H$_2$O: C, 54.62; H, 3.37; N, 4.25. Found: C, 54.61; H, 3.33; N, 4.18.

EXAMPLE 8

5-Chloro-2-methoxy-N-[4-(trifluoromethyl)phenyl]benzeneacetamide (IV$^8$: n=1)

mp 112–113° C.; Anal. calcd. for C$_{16}$H$_{13}$ClF$_3$NO$_2$: C, 55.91; H, 3.81; N, 4.07. Found: C, 55.97; H, 3.78; N, 4.07.

EXAMPLES 9 AND 10

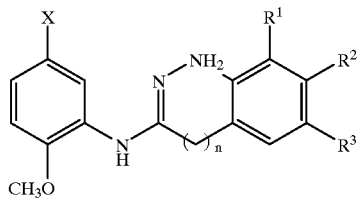

EXAMPLE 9

N-(5-chloro-2-methoxyphenyl)-3,5-bis(trifluoromethyl)benzene carbohydrazonamide ($V^9$: X=Cl, n=0, $R_1$=$R_3$=$CF_3$, $R_2$=H)

N-(5-Chloro-2-methoxyphenyl)-3,5-bis(trifluoromethyl)benzamide (8 g, 20.1 mmol) was dissolved in benzene (100 ml) under $N_2$ and phosphorous pentachloride (4.6 g, 22.1 mmol) added. The solution was heated at reflux for 3 h and solvent removed by rotary evaporation. The residue was taken up in THF (165 ml) and cannulated dropwise into a solution of anhydrous hydrazine (6.4 ml) in the same solvent (165 ml) at 0° C. under $N_2$. After being stirred 1 h at 24° C., the reaction mixture was poured into water (200 ml) and extracted with ethyl acetate (2×250 ml) and the organic phase washed with brine and dried over sodium sulfate. Concentration gave 7.69 g (93%) mp 117–120° C.; IR(KBr, υ=cm$^{-1}$) 3339, 3252, 1591, 1510, 1384, 1284, 1255, 1182, 1128; $^1$H NMR (300 MHz, CDCl$_3$) δ 3.93 (3H, s), 5.66 (2H, br.s), 5.94 (1H, br.s), 6.25–6.26 (1H, m), 6.77–6.84 (2H, m), 7.78 (1H, s), 8.01 (2H, s); MS(DCl)m/z: 412(MH$^+$). Anal. calcd. for $C_{16}H_{12}ClF_6N_3O$: C, 46.68; H, 2.94; N, 10.21. Found: C, 46.77; H, 2.83; N, 9.95.

EXAMPLE 10

N-(5-Chloro-2-methoxyphenyl)-4-(trifluoromethyl)benzene carbohydrazonamide ($VI^{10}$: X=Cl, n=0, $R_1$=$R_3$=H, $R_2$=$CF_3$)

The title amidrazone was prepared in a similar manner to example 9.

mp 94–95° C.; H. Res. MS calcd. for $C_{15}H_{13}ClF_3N_3O$: 344.0777; Found: 344.077; Dev: 2.2 ppm.

EXAMPLES 11–16

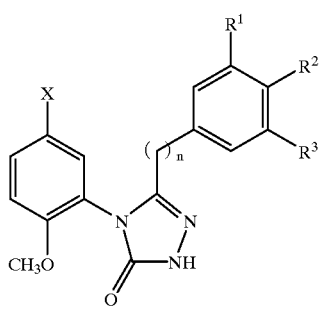

EXAMPLE 11

4-(5-Chloro-2-methoxyphenyl)-5-[3,5-bis(trifluoromethyl)phenyl]-2,4-dihydro-3H-1,2,4-triazol-3-one ($I^{11}$: X=Cl, n=0, $R_1$=$R_3$=$CF_3$, $R_2$=H)

N-(5-Chloro-2-methoxyphenyl)-3,5-bis(trifluoromethyl)benzene carbohydrazonamide (4 g, 9.7 mmol) was taken up in THF (600 ml) under $N_2$ and 1,1'-carbonyldiimidazole (1.9 g, 11.72 mmol) added. The solution was stirred for 18 h at 24° C. before solvent was removed by rotary evaporation. The residue was taken up in ethyl acetate (400 ml) and washed with 0.1N HCl solution (100 ml), water (100 ml) and brine prior to drying over MgSO$_4$. Recrystallization from acetonitrile gave 2.92 g (68.6%) mp 205.5–207° C. IR(KBr, υ=cm$^{-1}$) 3170, 3057, 1726, 1504, 1277, 1128; $^1$H NMR (300 MHz, DMSO-d$_6$) δ 3.48 (3H, s), 7.15 (1H, d, J=9.0 Hz), 7.55 (1H, dd, J=8.9 Hz, 2.6 Hz), 7.69 (1H, d, J=2.6 Hz), 7.87 (2H, br.s), 8.17 (1H, br.s), 12.50 (1H, br.s); MS(DCl) m/z: 438(MH$^+$). Anal. calcd. for $C_{17}H_{10}ClF_6N_3O_2$: C, 46.65; H, 2.30; N, 9.60. Found: C, 46.71; H, 2.20; N, 9.60.

The triazolones of Examples 12 through 18 were prepared using a procedure similar to Example 11.

EXAMPLE 12

4-(5-Chloro-2-methoxyphenyl)-5-[4-(trifluoromethyl)phenyl]-2,4-dihydro-3H-1,2,4-triazol-3-one ($I^{12}$: X=Cl, n=0, $R_1$=$R_3$=H, $R_2$=$CF_3$)

mp 250–253° C.; Anal. calcd. for $C_{15}H_{11}ClF_3N_3O_2$.0.03 $H_2O$: C, 51.91; H, 3.01; N, 11.35. Found: C, 52.11; H, 2.97; N, 11.32.

EXAMPLE 13

4-(5-Chloro-2-methoxyphenyl)-5-[3-(trifluoromethyl)phenyl]-2,4-dihydro-3H-1,2,4-triazol-3-one ($I^{13}$: X=Cl, n=0, $R_1$=$CF_3$, $R_2$=$R_3$=H)

mp 207.5–209° C.; Anal. calcd. for $C_{16}H_{11}ClF_3N_3O_2$: C, 51.98; H, 3.00; N, 11.37. Found: C, 52.12; H, 2.84; N, 11.51.

EXAMPLE 14

4-(5-Chloro-2-methoxyphenyl-5-(4-fluorophenyl)-2,4-dihydro-3H-1,2,4-triazol-3-one ($I^{14}$: X=Cl, n=0, $R_1$=$R_3$=H, $R_2$=F)

mp 270.5–273° C.; Anal. calcd. for $C_{15}H_{11}ClFN_3O_2$.0.02 $H_2O$: C, 56.30; H, 3.48; N, 13.13. Found: C, 56.25; H, 3.39; N, 13.08.

EXAMPLE 15

4-[2-Methoxy-5-(trifluoromethyl)phenyl]-5-[4-(trifluoromethyl)phenyl]-2,4-dihydro-3H-1,2,4-triazol-3-one ($I^{15}$: X=$CF_3$, n=0, $R_1$=$R_3$=H, $R_2$=$CF_3$)

mp 255–256° C.; Anal. calcd. for $C_{17}H_{11}F_6N_3O_2$: C, 50.63; H, 2.75; N, 10.42. Found: C, 50.61; H, 2.66; N, 10.45.

EXAMPLE 16

4-(5-Chloro-2-methoxyphenyl)-[[-5,4-(trifluoromethyl)phenyl]methyl]-2,4-dihydro-3H-1,2,4-triazol-3-one ($I^{16}$: X=Cl, n=1, $R_1$=$R_3$=H, $R_2$=$CF_3$)

mp 154–155° C.; Anal. calcd. for $C_{17}H_{13}ClF_3N_3O_2$: C, 53.21; H, 3.41; N, 10.95. Found: C, 53.10; H, 3.46; N, 10.89.

EXAMPLES 17 AND 18

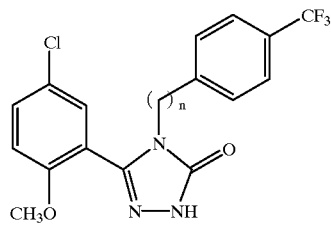

EXAMPLE 17

5-(5-Chloro-2-methoxyphenyl)-4-[4-(trifluoromethyl)phenyl]-2,4-dihydro-3H-1,2,4-triazol-3-one ($II^{17}$: n=0)

mp 213–214.5° C.; Anal. calcd. for $C_{16}H_{11}ClF_3N_3O_2$: C, 51.19; H, 3.02; N, 11.35. Found: C, 51.84; H, 2.95; N, 11.28.

EXAMPLE 18

5-(5-Chloro-2-methoxyphenyl)4-[[4-(trifluoromethyl)phenyl]methyl]-2,4-dihydro-3H-1,2,4-triazol-3-one ($II^{18}$: n=1)

mp 134–136° C.; Anal. calcd. for $C_{17}H_{13}ClF_3N_3O_2 \cdot 0.1 H_2O$: C, 52.94; H, 3.45; N, 10.89. Found: C, 52.94; H, 3.22; N, 10.95.

EXAMPLE 19

4-(5-Chloro-2-methoxyphenyl)-5-[4-(trifluoromethyl)phenyl]-2,4-dihydro-3H-1,2,4-triazol-3-thione ($VII^{19}$)

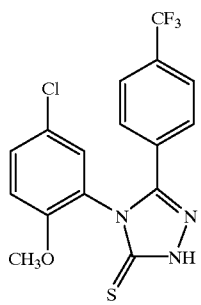

N-(5-Chloro-2-methoxyphenyl)-4-(trifluoromethyl)benzene carbohydrazonamide (2.5 g, 7.27 mmol) was dissolved in THF (450 ml) under $N_2$ and 1,1'-thiocarbonyldiimidazole (1.95 g, 11.0 mmol) added. The solution was stirred at reflux for 18 h and solvent removed by rotary evaporation. The residue was taken up in ethyl acetate (400 ml) and washed with 0.1N HCl solution (100 ml), water (100 ml) and brine prior to drying over $MgSO_4$. Recrystallization from acetonitrile gave 1.91 g (68%) mp 275–280° C.; IR(KBr, υ=cm$^{-1}$) 3080, 3058, 3020, 2916, 1506, 1488, 1322, 1288, 1174, 1130, 1110; $^1$H NMR (300 MHz, DMSO-d$_6$) δ 3.51 (3H, s), 7.17 (1H, d, J=9.0 Hz), 7.53–7.57 (3H, m), 7.69 (1H, d, J=2.6 Hz), 7.77 (2H, d, J=8.4 Hz.s), 14.29 (1H, s); MS(DCl)m/z: 386(MH$^+$). Anal. calcd. for $C_{16}H_{11}ClF_3N_3OS \cdot 0.06\ CH_3CN$: C, 49.87; H, 2.90; N, 11.04. Found: C, 50.03; H, 2.94; N, 11.07.

EXAMPLE 20

4-(5-Chloro-2-methoxyphenyl)-5-[4-(trifluoromethyl)phenyl]-4H-1,2,4-triazol-3-amine ($VIII^{20}$)

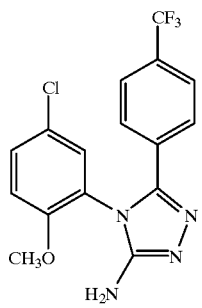

N-(5-Chloro-2-methoxyphenyl)-4-(trifluoromethyl)benzene carbohydrazonamide (1.5 g, 4.36 mmol) was dissolved in 1,4-dioxane (7 ml) and cyanogen bromide (475 mg, 4.48 mmol) was added. A solution of sodium bicarbonate (380 mg in 7 ml of water) was added dropise at room temperature and the reaction mixture was stirred for 3 h. An additional 7 ml of water was added to the heterogenous reaction mixture before filtration and rinse with water. Recrystallization from acetonitrile gave 922 mg (57.3%) mp 247–248° C.; IR(KBr, υ=cm$^{-1}$) 3416, 3076, 3052, 1652, 1561, 1504, 1322, 1110; $^1$H NMR (300 MHz, DMSO-d$_6$) δ 3.60 (3H, s), 5.92 (2H, s), 7.22 (1H, d, J=9.5 Hz), 7.47 (2H, d, 8.3 Hz), 7.54–7.57 (2H, m), 7.67 (1H, d, J=8.4 Hz).; MS(DCl)m/z: 369(MH$^+$). Anal. calcd. for $C_{16}H_{12}ClF_3N_4O$: C, 52.12; H, 3.28; N, 15.19. Found: C, 52.19; H, 3.20; N, 15.29.

EXAMPLE 21

1-(5-Chloro-2-methoxyphenyl)-5-[4-(trifluoromethyl)phenyl]-1H-imidazole ($XI^{21}$)

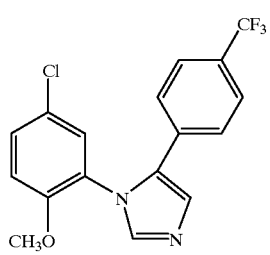

5-Chloroansidine (6.0 g, 38.2 mmol) and 4-ααα-trifluoro-tolualdehyde (6.6 g, 38.2 mmol) were dissolved in methanol (250 ml) and stirred for 3 h. The solvent was removed by evaporation and the residue taken up benzene (200 ml) and the solution heated under Dean-Stark conditions to remove traces of methanol prior to distillation of the benzene. The residue was taken up in DMF and tosylmethylisocyanide (7.46 g, 3.82 mmol) and DBU (0.5 ml, 3.82 mmol) were added under $N_2$. The reaction mixture was stirred at 24° C. for 48 h before being diluted with water (1 vol) and extracted with ethyl acetate. The organic phase was washed with water, brine, and dried. Chromatograhpy, elution with 30% ethyl acetate/benzene, gave 1 g (8%) mp 158–159° C.; IR(KBr, υ=cm⁻¹) 1504, 1462, 1324, 1260, 1176, 1122; ¹H NMR (300 MHz, CDCl₃) δ 3.49 (3H, s), 6.86 (1H, d, J=8.9 Hz), 7.20–7.24 (3H, m), 7.32–7.38 (2H, m), 7.48 (2H, d, J=8.2 Hz), 7.60 (1H, s); MS(DCl)m/z: 353 (MH⁺). Anal. calcd. for $C_{17}H_{12}ClF_3N_2O$: C, 57.88; H, 3.43; N, 7.94. Found: C, 58.08; H, 3.50; N, 7.91.

EXAMPLE 22

1-(5-Chloro-2-methoxyphenyl)-2-[4-(trifluoromethyl)phenyl]-1H-imidazole (IX²²)

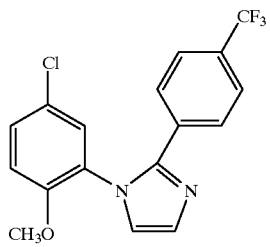

IX²²

N-(5-Chloro-2-methoxyphenyl)-4-(trifluoromethyl) benzamide (5.17 g, 15.7 mmol) was dissolved in benzene (100 ml) under N₂ and phosphorous pentachloride (3.61 g, 17.3 mmol) added. The solution was heated at reflux for 2.5 h before distillation in vacuo to remove solvent and phosphorosoxychloride. The residue was taken up in THF (55 ml) and cannulated dropwise into a solution of aminoacetaldehyde diethyl acetal (5 ml, 34.4 mmol) in 50 ml of the same solvent at 0° C. under N₂. After being stirred 18 h at 24° C., the reaction mixture was diluted with diethylether (1.5 vol) and filtered. The filtrate was concentrated by rotary evaporation to give an oil (7.63 g) which was dissolved in benzene (500 ml). Two equivalents of p-TsOH.H₂O (6 g, 30 mmol) was added and the solution heated at reflux for 2 h under Dean-Stark conditions. The solution was concentrated by rotary evaporation and the residue was partitioned between ethyl acetate and water. The aqueous phase was extrated with ethyl acetate and the combined organic layers were washed with water and brine before drying over MgSO₄. Chromatography on SiO₂, elution with 10% ethyl acetate/ methylene chloride gave a solid 4.15 g (75%). mp 151–152.5° C.; IR(KBr, υ=cm⁻¹) 1504, 1464, 1324, 1284, 1246, 1176, 1122, 1108, 1074,846; ¹H NMR (300 MHz, DMSO-d₆) δ 3.48 (3H, s), 7.17–7.21 (2H, m), 7.43 (1H, d, J=1.3 Hz), 7.51–7.59 (4H, m), 7.66 (2H, d, J=8.4 Hz); MS(DCl)m/z: 353(MH⁺). Anal. calcd. for $C_{17}H_{12}ClF_3N_2O$: C, 57.89; H, 3.43; N, 7.94. Found: C, 57.74; H, 3.40; N, 7.88.

The imidazoles of Examples 23 and 24 were prepared in a manner similar to that of Example 22.

EXAMPLES 23 AND 24

X²³⁻²⁴

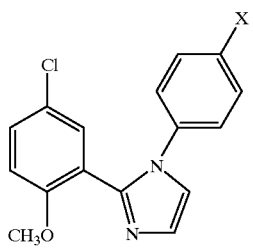

EXAMPLE 23

2-(5-Chloro-2-methoxyphenyl)-1-[4-(trifluoromethyl)phenyl]-1H-imidazole (X²³: X=CF₃)

mp 95–106° C.; Anal. calcd. for $C_{17}H_{12}ClF_3N_2O$: C, 57.89; H, 3.43; N, 7.94. Found: C, 58.20; H, 3.56; N, 7.87.

EXAMPLE 24

2-(5-Chloro-2-methoxyphenyl)-1-phenyl-1H-imidazole (X²⁴: X=H)

mp 97–102° C.; Anal. calcd. for $C_{16}H_{13}ClN_2O.0.06\ H_2O$: C, 67.24; H, 4.63; N, 9.80. Found: C, 67.02; H, 4.56; N, 9.72.

EXAMPLES 25–30

I²⁵⁻³⁰

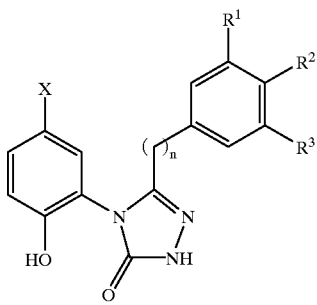

EXAMPLE 25

4-(5-Chloro-2-hydroxyphenyl)-5-[3,5-bis(trifluoromethyl)phenyl]-2,4-dihydro-3H-1,2,4-triazol-3-one (I²⁵: X=Cl, n=0, $R_1=R_3=CF_3$, R2=H)

5-[3,5-Bis(trifluoromethyl)phenyl]-4-(5-chloro-2-methoxy phenyl)-2,4-dihydro-3H-1,2,4-triazol-3-one (1.6 g, 3.6 mmol) was admixed with pyridine hydrochloride (6.7 g, 58 mmol) and heated at 225° C. for 1 h. After being cooled, the solid was covered with ethyl acetate (25 ml) and water (15 ml) and subjected to ultrasonication (bath) for several minutes in order to break the solid free from the glass wall. The organic suspension was diluted with ethyl acetate (100 ml) washed with water (25 ml), saturated sodium carbonate solution (25 ml), and brine. Concentration gave a solid 1.46 g (95%) which was recrystallized from acetonitrile. mp 275–278° C. IR(KBr, υ=cm⁻¹) 3166, 1681, 1314, 1275, 1180, 1140; ¹H NMR (300 MHz, DMSO₆) δ 6.92 (1H, d, J=8.8 Hz), 7.38 (1H, dd, J=8.8 Hz, 2.6 Hz), 7.58 (1H, d, J=2 Hz), 7.91 (2H, s), 8.17 (1H, s), 10.45 (1H, s), 10.45 (1H, s), 12,44 (1H, s); MS(DCl)m/z: 424(MH$^+$). Anal. calcd. for $C_{16}H_8ClF_6N_3O_2$: C, 45.36; H, 1.90; N, 9.92. Found: C, 45.28; H, 1.89; N, 9.77.

The phenols of Examples 26 through 36 were prepared in a manner similar to Example 25.

EXAMPLE 26

4-(5-Chloro-2-hydroxyphenyl)-5-[4-(trifluoromethyl)phenyl]-2,4-dihydro-3H-1,2,4-triazol-3-one ($I^{26}$: X=Cl, n=0, $R_1=R_3$=H, $R_2=CF_3$)

mp 292–294° C.; Anal. calcd. for $C_{15}H_9ClF_3N_3O_2$: C, 50.68; H, 2.60; N, 11.73. Found: C, 51.04; H, 2.74; N, 11.55.

EXAMPLE 27

4-(5-Chloro-2-hydroxyphenyl)-5-[3-(trifluoromethyl)phenyl]-2,4-dihydro-3H-1,2,4-triazol-3-one ($I^{27}$: X=Cl, n=0, $R_1=CF_3$, $R_2=R_3$=H)

mp 232.5–233.5° C.; Anal. calcd. for $C_{15}H_9ClF_3N_3O_2$.0.05 EtOAc: C, 50.70; H, 2.63; N, 11.67. Found: C, 50.62; H, 2.56; N, 11.64.

EXAMPLE 28

4-(5-Chloro-2-hydroxyphenyl)-5-(4-fluorophenyl)-2,4-dihydro-3H-1,2,4-triazol-3-one ($I^{28}$: X=Cl, n=0, $R_1=R_3$=H, $R_2$=F)

mp 270.5–272.5° C.; Anal. calcd. for $C_{14}H_9ClFN_3O_2$.0.075 $H_2O$: C, 54.77; H, 3.00; N, 13.69. Found: C, 54.77; H, 3.04; N, 13.71.

EXAMPLE 29

[4,2-Hydroxy-5-(trifluoromethyl)phenyl]-5-[4-(trifluoromethyl)phenyl]-2,4-dihydro-3H-1,2,4-triazol-3-one ($I^{29}$: X=$CF_3$, n=0, $R_1=R_3$=H, $R_2=CF_3$)

mp 270–274° C.; Anal. calcd. for $C_{16}H_9F_6N_3O_2$: C, 48.88; H, 2,42; N, 10.69. Found: C, 49.36; H, 2.24; N, 10.82.

EXAMPLE 30

4-(5-Chloro-2-hydroxyphenyl)-5-[[(trifluoromethyl)phenyl]methyl]-2,4-dihydro-3H-1,2,4-triazol-3-one ($I^{30}$: X=Cl, n=1, $R_1=R_3$=H, $R_2=CF_3$)

mp 270–274° C.; Anal. calcd. for $C_{16}H_{11}ClF_3N_3O_2$: C, 51.98; H, 3.00; N, 11.37. Found: C, 51.92; H, 2.88; N, 11.23.

EXAMPLE 31

4-(5-Chloro-2-hydroxyphenyl)-5-[4-(trifluoromethyl)phenyl]-2,4-dihydro-3H-1,2,4-triazol-3-thione ($VII^{31}$)

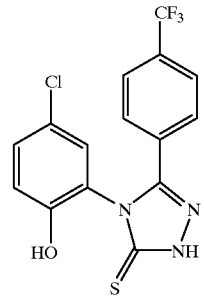

$VII^{31}$ mp 274–276° C.; H. Res. MS calcd. for: $C_{15}H_9ClF_3N_3OS$: 372.0185; Found: 372.0197; Dev: 3.2 ppm.

EXAMPLE 32

4-Chloro-2-[2-[4-(trifluoromethyl)phenyl]-1H-imidazol-1-yl]phenol ($IX^{32}$)

mp 252–254° C.;

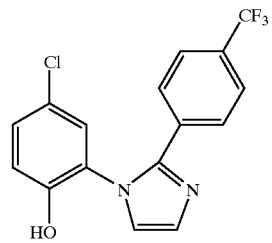

$IX^{32}$

Anal. calcd. for $C_{16}H_{10}ClF_3N_2O$: C, 56.74; H, 2.98; N, 8.27. Found: C, 56.65; H, 2.94; N, 8.14.

EXAMPLES 33 AND 34

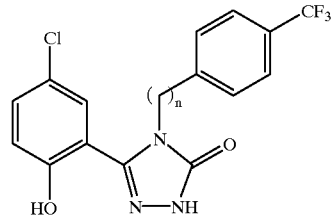

$II^{33-34}$

EXAMPLE 33

5-(5-Chloro-2-hydroxyphenyl)-4-[4-(trifluoromethyl)phenyl]-2,4-dihydro-3H-1,2,4-triazol-3-one ($II^{33}$: n=0)

mp 236–238.5° C.; Anal. calcd. for $C_{15}H_9ClF_3N_3O_2$.0.1 EtOAc: C, 50.75; H, 2.71; N, 11.53. Found: C, 50.97; H, 2.81; N, 11.32.

EXAMPLE 34

5-(5-Chloro-2-hydroxyphenyl)-4-[[4-(trifluoromethyl)phenyl]methyl]-2,4-dihydro-3H-1,2,4-triazol-3-one (II[34]: n=1)

mp 217–219° C.; Anal. calcd. for $C_{16}H_{11}ClF_3N_3O_2 \cdot 0.1\ H_2O$: C, 51.72; H, 3.04; N, 11.31. Found: C, 51.95; H, 2.90; N, 11.31.

EXAMPLES 35 AND 36

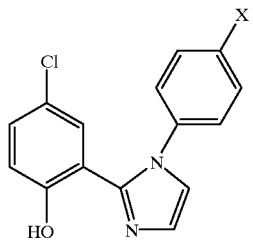

X[35-36]

EXAMPLE 35

4-Chloro-2-[1-[4-(trifluoromethyl)phenyl]-1H-imidazol-2-yl]phenol (X[35]: X=CF$_3$)

mp 110–112.5° C.; Anal. calcd. for $C_{16}H_{10}ClF_3N_2O \cdot 0.01\ H_2O$: C, 56.52; H, 3.01; N, 8.24. Found: C, 56.68; H, 2.86; N, 8.18.

EXAMPLE 36

4-Chloro-2-[1-phenyl-1H-imidazol-2-yl]phenol (X[36]: X=H)

mp 137–138.5° C.; Anal. calcd. for $C_{15}H_{11}ClN_2O$: C, 66.55; H, 4.10; N, 10.35. Found: C, 66.76; H, 4.24; N, 10.26.

EXAMPLE 37

4-Chloro-2-[3-amino-[5-[4-(trifluoromethyl)phenyl]-4H-1,2,4-triazol-4-yl]]phenol (VIII[37])

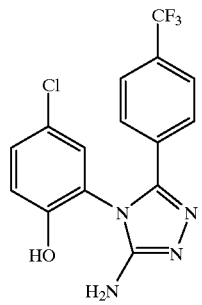

VIII[37]

4-(5-Chloro-2-methoxyphenyl)-5-[4-(trifluoromethyl)phenyl]-4H-1,2,4-triazol-3-amine (1.5 g, 4.1 mmol) was taken up in methylene chloride (forms suspension), cooled to 0° C. under N$_2$, and from 3 to 6 eq. boron tribromide (25 ml, 1.0M in CH$_2$Cl$_2$) added. The reaction was stirred at 24° C. for 18 h, and 1N sodium hydroxide (80 ml) was added and the solvent was removed by rotary evaporation and the residue was taken up in ethyl acetate and enough THF added to complete dissolution. After being washed with 0.1N HCl solution and brine the solution was dried over MgSO4. Chromatography, elution 1% AcOH/5% methanol in dichloromethane gave 795 mg (55%). mp 147–155° C. H. Res. MS calcd. for $C_{15}H_{10}ClF_3N_4O$: 355.0574; Found: 355.0566; Dev: 2.3 ppm.

EXAMPLE 38

1-(5-Chloro-2-hydroxyphenyl)-5-[4-(trifluoromethyl)phenyl]-1H-imidazole (XI[38])

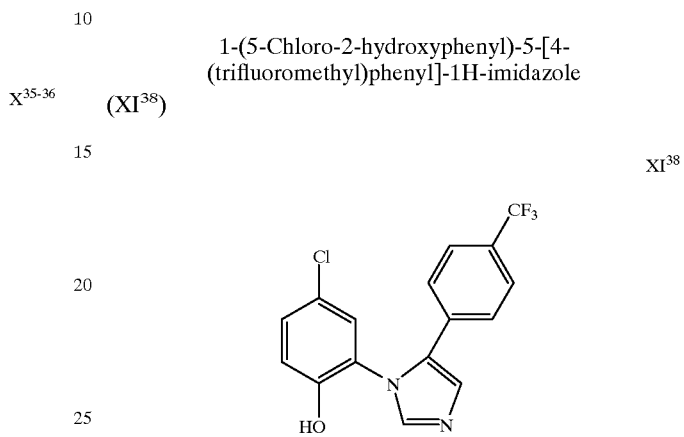

XI[38]

The title phenol was prepared by the BBr$_3$ method of Example 37.

mp 220–225° C.; Anal. calcd. for $C_{16}H_{10}ClF_3N_2O \cdot 0.15\ H_2O$: C, 56.06; H, 2.94; N, 8.17. Found: C, 55.65; H, 2.94; N, 7.81.

Preparation No. 2

EXAMPLE 39

N-(5-Chloro-2-methoxyphenyl)-N'-(2-oxo-2-phenylethyl)urea (XII[39])

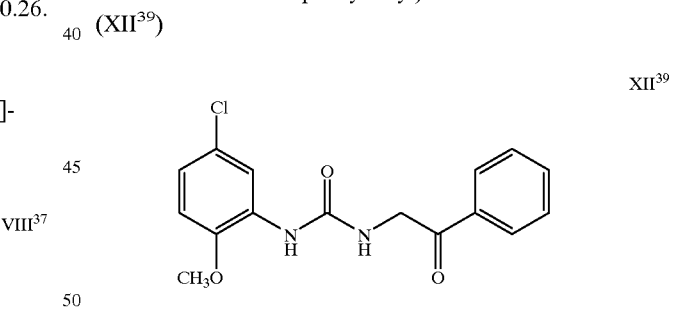

XII[39]

5-Chloro-2-methoxyphenylisocyanate (5.3 g, 29 mmol) was dissolved in THF (250 ml) under N$_2$ and heated to 60° C. To this solution was added 2-aminoacetophenone-HCl (5 g, 29 mmol) followed by triethylamine (3.8 g, 30 mmol). After being stirred 1.5 h, the reaction mixture was diluted with ethyl acetate (2 vol) and washed with 1N HCl solution, saturated NaCO$_3$ solution, and brine before being dried, MgSO$_4$. Concentration gave a solid which was washed with diethylether 6 g (65%). mp 171–173° C.; IR(KBr, $\upsilon$=cm$^{-1}$) 3336, 1706, 1644, 1600, 1560, 1482, 1262, 1220, 1182, 1126; $^1$H NMR (300 MHz, CDCl$_3$) δ 3.79 (3H, s), 4.84 (2H, d, J=4.3 Hz), 5.97 (1H, br.s), 6.71 (1H, d, J=8.7 Hz), 6.88 (1H, dd, J=8.7 Hz, 2.5 Hz), 7.97–8.00 (2H, m), 8.18 (1H, d, J=2.5 Hz); MS(DCl)m/z: 319(MH$^+$); Anal. calcd. for $C_{16}H_{15}ClN_2O_3$: C, 60.29; H, 4.74; N, 8.79. Found: C, 60.17; H, 4.64; N, 8.70.

EXAMPLE 40

1-(5-Chloro-2-methoxyphenyl)-1,3-dihydro-2H-imidazol-2-one (XIII$^{40}$)

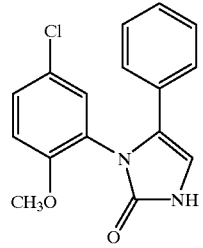

XIII$^{40}$

N-(5-Chloro-2-methoxyphenyl)-N'-(2-oxo-2-phenylethyl) urea (4 g, 12.7 mmol) was added to cold (0° C.) concentrated sulfuric acid and stirred for 3 h. The reaction mixture was poured into ice water (2 vol), and extracted with ethyl acetate, washed with saturated NaHCO$_3$ solution and brine before drying over MgSO$_4$. Recrystallization from diethylether/acetonitrile gave 1.35 g (36%). mp 133–134° C.; IR(KBr, υ=cm$^{-1}$) 2962, 1628, 1576, 1236, 1144, 1130; $^1$H NMR (300 MHz, CDCl$_3$) δ 3.90 (3H, s), 6.77 (1H, d, J=8.6 Hz), 6.91 (1H, dd, J=8.6 Hz, 2.5 Hz), 7.16 (1H, s), 7.22–7.27 (1H, m), 7.35–7.40 (2H, m), 7.51–7.55 (3H, m), 8.29 (1H, d, J=2.5 Hz); MS(DCl)m/z: 301 (MH$^+$); Anal. calcd. for C$_{16}$H$_{13}$ClN$_2$O$_2$: C, 63.90; H, 4.36; N, 9.31. Found: C, 63.66; H, 4.30; N, 9.21.

EXAMPLE 41

1-(5-Chloro-2-hydroxyphenyl)-1,3-dihydro-5-phenyl-2H-imidazol-2-one (XIII$^{41}$)

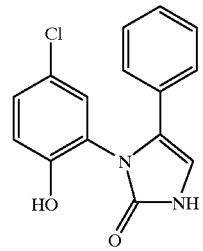

XIII$^{41}$

The title phenol was prepared according to the BBr$_3$ method of Example 37 above.

mp 190–192° C.; Anal. calcd. for C$_{15}$H$_{11}$ClN$_2$O$_2$: C, 62.83; H, 3.87; N, 9.77. Found: C, 62.87; H, 3.92; N, 9.82.

Preparation No. 3

EXAMPLE 42

1-(5-Chloro-2-methoxyphenyl)-5-phenyl-2,4-imidazolidinedione (XIV$^{42}$)

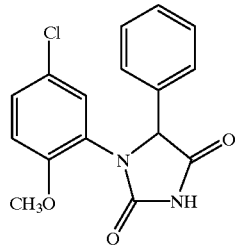

XIV$^{42}$

N-(5-Chloro-2-methoxyphenyl)urea (1 g, 5 mmol) and phenylglyoxal monohydrate (760 mg, 5 mmol) were taken up in absolute ethanol (100 ml) and acetic acid (1 ml) and 1 ml of conc. HCl added. The reaction mixture was heated at reflux 3.5 h and allowed to stand at 24° C. for 18 h prior to concentration by rotary evaporation. The residue was dissolved in ethyl acetate, washed with sat'd NaHCO$_3$ solution and brine. Recrystallization from methylene chloride/hexanes gave 1 g (63%) mp 200° C.; IR(KBr, υ=cm$^{-1}$) 3168, 3064, 1772, 1701, 1504, 1444, 1426, 1408, 1260, 1190, 1150; $^1$H NMR (300 MHz, CDCl$_3$) δ 3.59 (3H, s), 5.60 (1H, s), 6.80 (1H, d, J=8.8 Hz), 7.14–7.37 (7H, m), 8.92 (1H, br.s); MS(DCl)m/z: 317(MH$^+$); Anal. calcd. for C$_{16}$H$_{13}$ClN$_2$O$_3$: C, 60.67; H, 4.13; N, 8.84. Found: C,60.47; H, 4.12; N, 8.80.

EXAMPLE 43

1-(5-Chloro-2-hydroxyphenyl)-5-phenyl-2,4-imidazolidinedione (XIV$^{43}$)

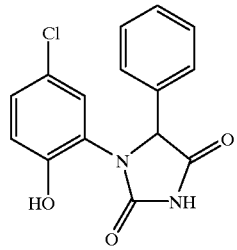

XIV$^{43}$

The title phenol was prepared according to the BBr$_3$ method of Example 37.

mp 235–236° C.; Anal. calcd. for C$_{15}$H$_{11}$ClN$_2$O$_3$: C, 59.51; H, 3.66; N, 9.25. Found: C, 59.27; H, 3.66; N, 9.51.

Preparation No. 4

Oxadiazolone starting materials were prepared according to the procedures set out in M. D. Mullican, et al. *J. Med. Chem.* 36, 1090 (1993).

EXAMPLES 44–55

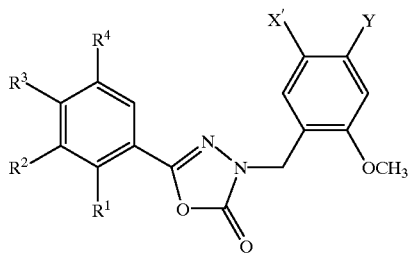

XV⁴⁴⁻⁵⁵

EXAMPLE 44

3-[[4-(Acetylamino)-5-chloro-2-methoxyphenyl]methyl]-5-[3,4-dichlorophenyl]-1,3,4-oxadiazol-2(3H)-one ($XV^{44}$: X'=Cl, Y=NHAc, $R^1$=$R^4$=H, $R^2$=$R^3$=Cl)

5-(3,4-Dichlorophenyl)-1,3,4-oxadiazol-2(3H)-one (2.0 g, 8.66 mmol), N-[4-(bromomethyl)-2-chloro-5-methoxyphenyl]acetamide [JP 49049929] (2.2 g, 8.67 mmol), $K_2CO_3$ (1.9 g, 13.8 mmol) and KI (cat.) were heated at reflux in acetonitrile (50 ml) for 18 h. After being cooled, the reaction mixture was poured into water (300 ml), stirred vigourously, and filtered. Recrystallization from acetonitrile water gave pale yellow crystals 2.2 g (57.8%). mp 200–201.5° C. IR(KBr, υ =$cm^{-1}$) 3340, 1804, 1404, 1014, 850, 736; $^1$H NMR (300 MHz, $CDCl_3$) δ 2.21 (3H, s), 3.83 (3H, s), 4.87 (2H, s), 7.22 (1H, s), 7.49 (1H, d, J=8.4 Hz), 7.60 (1H, dd, J=8.4 Hz, 2.0 Hz), 7.64 (1H, br.s), 7.86 (1H, d, J=2.0 Hz), 8.11(1H, s); MS(ESl)m/z: 440(M-H⁻). Anal. calcd. for $C_{18}H_{14}Cl_3N_3O_4$: C, 48.84; H, 3.19; N, 9.49. Found: C, 49.07; H, 3.17; N, 9.61.

The following oxadiazolones were prepared in a manner similar to Example 44.

EXAMPLE 45

3-[[4-(Acetylamino)-5-chloro-2-methoxyphenyl]methyl]-5-[3,5-dichlorophenyl]-1,3,4-oxadiazol-2(3H)-one ($XV^{45}$: X'=Cl, Y=NHAc, $R^1$=$R^3$=H, $R^2$=$R^4$=Cl)

mp 144–145° C.; Anal. calcd. for $C_{18}H_{14}Cl_3N_3O_4$: C, 48.84; H, 3.19; N, 9.49. Found: C, 48.83; H, 3.35; N, 9.72.

EXAMPLE 46

3-[(4-(Acetylamino)-5-chloro-2-methoxyphenyl)methyl]-5-[4-(trifluoromethyl)phenyl]-1,3,4-oxadiazol-2(3H)-one ($XV^{46}$: X'=Cl, Y=NHAc, $R_1$=$R^2$=$R^4$=H, $R^3$=$CF_3$)

mp 202–205.5° C.; Anal. calcd. for $C_{19}H_{15}ClF_3N_4O_4$·0.1 $H_2O$·0.1 THF: C, 51.69; H, 3.58; N, 9.32. Found: C, 51.71; H, 3.49; N, 9.30.

EXAMPLE 47

3-[(4-(Acetylamino)-5-chloro-2-methoxyphenyl)methyl]-5-([1,1'-biphenyl]-4-yl)]-1,3,4-oxadiazol-2(3H)-one ($XV^{47}$: X'=Cl, Y=NHAc, $R^1$=$R^2$=H, $R^3$=Ph)

mp 203–204° C.; Anal. calcd. for $C_{24}H_{20}ClN_3O_3$: C, 64.07; H, 4.48; N, 9.34. Found: C, 64.02; H, 4.52; N, 9.21.

EXAMPLE 48

3-[(4-(Acetylamino)-5-chloro-2-methoxyphenyl)methyl]-5-(2-naphthalenyl)-1,3,4-oxadiazol-2(3H)-one ($XV^{48}$: X'=Cl, Y=NHAc, $R^1$=$R^4$=H, $R^3$=$R^4$=—$C_2H_2$—)

mp 209–211° C.; Anal. calcd. for $C_{22}H_{18}ClN_3O_4$: C, 62.34; H, 4.28; N, 9.91. Found: C, 62.15; H, 4.37; N, 10.02.

EXAMPLE 49

3-[2-Methoxyphenyl)methyl]-5-[4-(trifluoromethyl)phenyl]-1,3,4-oxadiazol-2(3H)-one ($XV^{49}$: X'=H, Y=H, $R^1$=$R^2$=$R^4$=H, $R^3$=$CF_3$)

mp 107.5–108.5° C.; Anal. calcd. for $C_{17}H_{13}F_3N_2O_3$: C, 58.29; H, 3.74; N, 8.00. Found: C, 58.30; H, 3.61; N, 7.90.

EXAMPLE 50

3-[(5-Chloro-2-methoxyphenyl)methyl]-5-[4-(trifluoromethyl)phenyl]-1,3,4-oxadiazol-2(3H)-one ($XV^{50}$: X'=Cl, Y=H, $R^1$=$R^2$=$R^4$=H, $R^3$=$CF_3$)

mp 144–145° C.; Anal. calcd. for $C_{17}H_{12}ClF_3N_2O_3$·0.1 $H_2O$: C, 52.81; H, 3.19; N, 7.25. Found: C, 53.03; H, 3.20; N, 7.31.

EXAMPLE 51

3-[(2-Methoxy-5-chlorophenyl)methyl]-5-[3,5-bis(trifluoromethyl)phenyl]-1,3,4-oxadiazol-2(3H)-one ($XV^{51}$: X'=Cl, Y=H, $R^1$=$R^3$=H, $R^2$=$R^4$=$CF_3$)

mp 127–128° C.; Anal. calcd. for $C_{18}H_{11}ClF_6N_2O_3$: C, 47.75; H, 2,45; N, 6.19. Found: C, 47.83; H, 2,42; N, 6.17.

EXAMPLE 52

3-[[2-Methoxy-5-chlorophenyl]methyl]-5-[2-chloro-5-(trifluoromethyl)-phenyl]-1,3,4-oxadiazol-2(3H)-one ($XV^{52}$: X'=Cl, Y=H, $R^1$=Cl, $R^3$=$R^2$=H, $R^4$=$CF_3$)

mp 151–152° C.; Anal. calcd. for $C_{17}H_{11}Cl_2F_3N_2O_3$: C, 48.71; H, 2.64; N, 6.68. Found: C, 48.39; H, 2.36; N, 6.78.

EXAMPLE 53

3-[[2-Methoxy-5-chlorophenyl]methy]5-[3,5-dichlorophenyl]-1,3,4-oxadiazol-2(3H)-one ($XV^{53}$: X'=Cl, Y=H, $R^1$=Cl, $R^1$=$R^3$=H, $R^2$=$R^4$=Cl)

mp 172–173° C.; Anal. calcd. for $C_{16}H_{11}Cl_3N_2O_3$: C, 49.83; H, 2.87; N, 7.26. Found: C, 49.75; H, 2.86; N, 7.31.

EXAMPLE 54

3-[(5-Chloro-2-methoxyphenyl)methyl]-5-[2-fluoro-4-(trifluoromethyl)-phenyl]1,3,4-oxadiazol-2(3H)-one ($XV^{54}$: X'=Cl, Y=H, $R^1$=F, $R^1$=$R^3$=H, $R^2$=$R^4$=$CF_3$)

mp 126–128° C.; Anal. calcd. for $C_{17}H_{11}ClF_4N_2O_3$: C, 50.70; H, 2.75; N, 6.96. Found: C, 50.55; H, 2.66; N, 7.07.

EXAMPLE 55

3-[(5-Chloro-2-methoxyphenyl)methyl]-5-[4-fluoro-3-(trifluoromethyl)-phenyl]-1,3,4-oxadiazol-2(3H)-one ($XV^{55}$: X'=Cl, Y=H, $R^1$=$R^4$=H, $R^2$=$CF_3$, $R^3$=F)

mp 118–119° C.; Anal. calcd. for $C_{17}H_{11}ClF_4N_2O_3$: C, 50.70; H, 2.75; N, 6.96. Found: C, 50.70; H, 2.72; N, 7.01.

EXAMPLES 56 AND 57

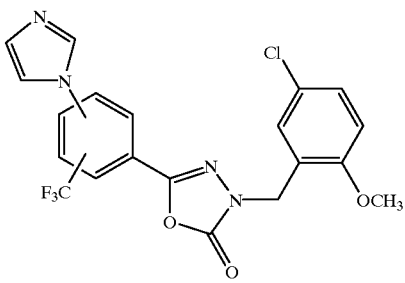

XVII[56-57]

EXAMPLE 56

3-[(5-Chloro-2-methoxyphenyl)methyl]-5-[2-(1H-imidazol-1-yl)-4-(trifluoromethyl)phenyl]-1,3,4-oxadiazol-2(3H)-one (XVII[56])

3-[(5-Chloro-2-methoxyphenyl)methyl]-5-[2-fluoro-4-(trifluoromethyl) phenyl]-1,3,4-oxadiazol-2(3H)-one (1.2 g, 2.97 mmol) and imidazole (269 mg, 3.95 mmol) were taken up in DMF (7 ml) under $N_2$ at room temperature and (135 mg, 4.6 mmol) sodium hydride (80%) was added in portions and the reaction mixture was heated at 80° C. for 3 h. The solution was diluted with saturated ammonium chloride solution and extract with ethyl acetate. The organic phase was washed with water, brine, and dried over $MgSO_4$. Concentration onto $SiO_2$, elution with 15% ethyl acetate/chloroform gave 1.16 g (61%).

mp 143.5–151° C.; Anal. calcd. for $C_{20}H_{14}ClF_3N_4O_3$: C, 53.29; H, 3.13; N, 12,43. Found: C, 53.36; H, 2.95; N, 12.24.

The following imidazole was prepared in a similar manner to Example 56.

EXAMPLE 57

3-[(5-Chloro-2-methoxyphenyl)methyl]-5-[4-(1H-imidazol-1-yl)-3-(trifluoromethyl)phenyl]-1,3,4-oxadiazol-2(3H)-one (XVII[57])

mp 148–150° C.; Anal. calcd. for $C_{20}H_{14}ClF_3N_4O_3$: C, 53.29; H, 3.13; N, 12,43. Found: C, 53.15; H, 3.10; N, 21.24.

EXAMPLE 58

4-(Acetylmethylamino)-5-chloro-2-methoxybenzoic acid, methyl ester

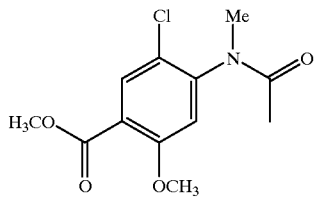

4-(Acetylamino)-5-chloro-2-methoxybenzoic acid, methyl ester (10.0 g, 38.08 mmol) was dissolved in anhydrous THF (250 ml) under $N_2$ and 1.23 g of sodium hydride (80%, 41.0 mmol) added in portions. Methyl iodide (2.5 ml, 40.1 mmol) was added and the reaction mixture heated at reflux for 5 h during which time additional MeI and NaH were added to drive the reaction to completion. Water was added, and the solution was concentrated by rotary evaporation and the residue taken up in ethyl acetate and washed with brine and dried over $MgSO_4$. Chromatography on $SiO_2$, elution with 55% ethyl acetate/hexanes gave 4.77 g (45%); mp 105.5–107° C.; IR(KBr, $\upsilon=cm^{-1}$) 3040, 1712, 1662, 1242; $^1$H NMR (300 MHz, DMSO-$d_6$) δ 1.72 (3H, s), 3.07 (3H, s), 3.79 (3H, s), 3.84 (3H, s), 7.41 (1H, s), 7.81 (1H, s); MS(DCl)m/z: 272 (MH$^+$). Anal. calcd. for $C_{12}H_{14}ClNO_4$: C, 53.05; H, 5.19; N, 5.15. Found: C, 53.05; H, 5.05; N, 4.96.

EXAMPLE 59

4-(Ethylmethylamino)-5-chloro-2-methoxybenzenemethanol

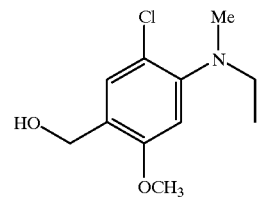

4-(Acetylmethylamino)-5-chloro-2-methoxybenzoic acid, methyl ester (2 g, 7.36 mmol) was taken up in anhydrous THF (50 ml) and 40 ml of diethylether. Lithium aluminum hydride (558 mg, 14.7 mmol) was added in portions and the reaction mixture stirred for 2 h before being cooled to 0° C. and quenched with 1N sodium hydroxide solution. The resulting suspension was filtered and the filtered salts washed extensively with THF. The filtrate was concentrated by rotary evaporation to give 1.6 g (89.5%) of an oil found to be a 5:1 mixture of product to 4-(acetylmethylamino)-5-chloro-2-methoxybenzenemethanol. Product: $^1$H NMR (300 MHz, DMSO-$d_6$) δ 1.06 (3H, t, J=7.03 Hz),2.69 (3H, s), 3.01 (2H, q, J=7.0 Hz), 3.77 (3H, s), 4.39 (2H, d, J=5.7 Hz), 5.01 (1H, t, J=5.7 Hz), 6.69 (1H, s), 7.27 (1H, s).

EXAMPLE 60

2-Methoxy-5-(4-morpholinylmethyl)benzenemethanol

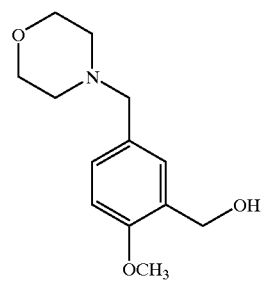

Step A: 4-[(4-Methoxyphenyl)methyl]morpholine Intermediate

4-Methyoxybenzylchloride (25 g, 0.16 mol), morpholine (14 g, 0.16 mol), and potassium carbonate (22 g, 0.16 mol) were taken up in acetonitrile and KI (8.7 g, 0.04 mol) added. The reaction mixture was heated at reflux for 18 h, filtered, and the filtrate concentrated and azeotropped with benzene to give 17.5 g (88%) as an oil; IR(film, $\upsilon=cm^{-1}$) 2956, 2806, 1514, 1246, 1118, 866; $^1$H NMR (300 MHz, DMSO-$d_6$) δ

2.29 (4H, br. s), 3.35 (2H, s), 3.53 (4H, t, J=4.4 Hz), 3.71 (3H, s), 6.86 (2H, d, J=8.5 Hz), 7.19 (2H, d, J=8.5 Hz); MS(DCl)m/z: 208 (MH+).

Step B: 2-Methoxy-5-(4-morpholinylmethyl) benzenemethanol

4-[(4-Methoxyphenyl)methyl]morpholine (5 g, 24.1 mmol), and co-solvent N, N, N', N', N''-pentamethyidiethylenetriamine (PMDTA) (5.4 ml, 26.0 mmol) were cooled to −78° C. in anhydrous THF under $N_2$ and 20 ml of sec-BuLi (1.3 M, 26.0 mmol) added via syringe. The reaction mixture was stirred 2 h and DMF (3.5 ml, 40 mmol) was added followed by slow warming to room temperature. The solution was concentrated and the residue taken up in ethyl acetate and washed with brine and dried.

The resultant aldehyde was taken up in methanol (500 ml) under $N_2$ and sodium borohydride (875 mg, 23.0 ml) was added in portions at room temperature. After being stirred 4.5 h, water (20 ml) was added and the solution concentrated by rotary evaporation. The residue was partitioned between ethyl acetate and water and the organic phase washed with brine. Chromatography on $SiO_2$, elution with methanol/ ethyl acetate/hexanes (1:2:7) gave 2.3 g (40%) of the alcohol as an oil; IR(film, υ=cm$^{-1}$) 3400, 2810, 1612, 1500, 1250, 1116, 1034; $^1$H NMR (300 MHz, DMSO-d$_6$) δ 2.30 (4H, br. s), 3.36 (2H, s), 3.54 (4H, t, J=5.6 Hz), 3.73 (3H, s), 4.46 (2H, d, J=5.6 Hz), 4.99 (1H, t, J=5.6 Hz), 6.85 (1H, d, J=8.3 Hz) 7.10 (1H, dd, J=8.2 Hz, 1.6 Hz), 7.30 (1H, s); MS(DCl) m/z: 238 (MH+).

EXAMPLE 61

5-(1H-imidazol-1-yl)-2-methoxybenzoic acid, methyl ester

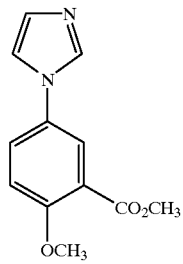

5-Bromo-2-methoxybenzoic acid, methyl ester (5 g, 20.4 mmol), imidazole (1.4 g, 20.6 mmol), and potassium carbonate (2.9 g, 20.7 mmol) were heated to 145° C. in DMF under $N_2$ as cuprous iodide (1.5 g, 7.9 mmol) was added in portions. The reaction was stirred at this temperature for 18 h, allowed to cool, and filtered through a celite plug. The filtered salts were washed extensively with methanol, the filtrate concentrated in vacuo, and the residue taken up in ethyl acetate, washed with water, brine, and dried. Chromatography on $SiO_2$, elution with methanol/ethyl acetate/ hexanes (1:1:3) gave 3 g (63%); IR(KBr, υ=cm$^{-1}$) 3430, 1726, 1512, 1232, 1068; $^1$H NMR (300 MHz, DMSO-d$_6$) δ 3.80 (3H, s), 3.85 (3H, s), 7.07 (1H, s), 7.27 (1H, d, J=8.8 Hz), 7.69 (1H, s), 7.76 –7.82 (2H, m) 8.18 (1H, s); MS(DCl) m/z: 233 (MH+).

EXAMPLE 62

5-(1H-Imidazol-1-yl)-2-methoxybenzenemethanol

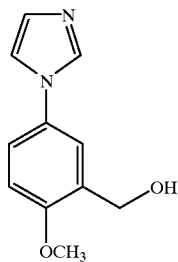

5-(1H-Imidazol-1-yl)-2-methoxybenzoic acid, methyl ester (2 g, 8.6 mmol) was cooled to 0C in anhydrous THF under $N_2$ and LiAlH$_4$ was added. The reaction mixture stirred for 18 h at 24° C,. and water (0.7 ml) followed 15% sodium hydroxide solution (0.7 ml) and water (0.7 ml) was sequentially added dropwise. The resultant suspension was filtered and concentrated to give 1.3 g (74%); $^1$H NMR (300 MHz, DMSO-d$_6$) δ 3.81(3H, s), 4.52 (2H, d, J=4.3 Hz), 5.18 (1H, br. s), 7.04 –7.06 (2H, m), 7.43 (1H, dd, J=8.7 Hz, 2.8 Hz), 7.52 (1H, d, J=2.8 Hz) 7.58 (1H, s), 8.07 (1H, s); MS(DCl)m/z: 205 (MH+).

EXAMPLE 63

2-Methoxy-5-(1-methyl-1H-imidazol-2-yl) benzenemethanol

Step A: [(5-Bromo-2-methoxyphenyl)methoxy]dimethyl(1, 1-dimethylethyl)silane

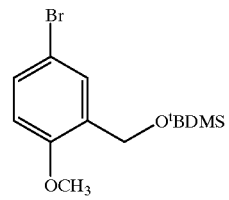

5-Bromo-o-anisaldehyde (30 g, 0.14 mol) was dissolved in THF (30 ml) and 500 ml of methanol. Sodium borohydride (8 g, 0.21 mol) was added in portions over 10 min. and the solution stirred for 3 h and quenched with 5% HCl solution. The solvent was removed by rotary evaporation and the residue taken up in ethyl acetate, washed with 1N HCl solution, water, and brine before drying over MgSO$_4$. Concentration gave an oil 29.4 g (97.2%).

The alcohol (20.0 g, 0.092 mol), t-butyldimethylsilyl chloride (15.28 g, 0.10 mol), and imidazole (13.82 g, 0.20 mol) were stirred in DMF (100 ml) for 18 h. The solution was poured into water (250 ml) and extracted with hexanes/ diethylether (1:2). The organic phase was washed with 1N HCl solution, water, brine, and dried over MgSO$_4$. Concentration gave an oil which crystallized on standing 29.9 g (98%); mp 28–29.5° C.; IR(KBr, υ=cm$^{-1}$) 2954, 2930, 1488, 1464, 1258, 1094; $^1$H NMR (300 MHz, DMSO-d$_6$) δ 0.06 (6H, s), 0.89 (9H, s), 3.75 (3H, s), 4.63 (2H, s), 6.90 (1H, d, J=8.6 Hz), 7.37 (1H, dd, J=8.6 Hz, 2.6 Hz), 7.42 (1H, d, J=2.5 Hz); MS(DCl)m/z: 331 (MH+).

Anal. calcd. for $C_{14}H_{23}BrO_2Si$: C, 50.75; H, 7.00. Found: C, 50.89; H, 6.95.

Step B: 2-Methoxy-5-(1-methyl-1H-imidazol-2-yl)benzenemethanol

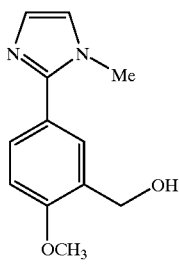

n-Butyllithium (5.2 mL of 2.5 M in hexanes) was added dropwise to N-methyl imidazole (2 g, 24.4 mmol) in THF (26 mL) under $N_2$ at −78° C., and the solution stirred 2.5 h before zinc chloride (3.33 g, 24.4 mmol) dissolved in 22 mL of the same solvent was added and the cold bath was removed. After 30 min, tetrakis (triphenylphosphine) palladium (0) (172 mg, 0.15 mmol) was added followed by a THF solution (14 ml) of [(5-bromo-2-methoxyphenyl)methoxy]dimethyl(1,1-dimethylethyl)silane (9.7 g, 29.3 mmol). The reaction mixture was stirred at reflux 2 h, cooled to room temperature, additional zinc chloride (6.77 g, 24.4 mmol) dissolved in 30 ml of THF added, and the solution brought back to reflux for 3 h. The solvent was removed by rotary evaporation and a solution of EDTA disodium salt (56.4 g in 700 ml of water) was added and the pH adjusted to ~8. The product was extrated with chloroform, and the organic phase washed with water, brine, and dried ($MgSO_4$). Purification by flash column chromatography on $SiO_2$ (elution with 35% THF/benzene) gave 4.32 g (53%).

The material was taken up in THF (45 ml) and 17 ml of tetra-n-butylammonium fluoride solution (1M in THF, 9.33 mol) added dropwise. The reaction mixture was stirred for 4 h, ammonium chloride solution (5 ml) added followed by saturated $NaCO_3$ solution, and extration into ethyl acetate. The organic phase washed with brine and concentrated. Recrystallization from ethyl acetate gave 2.22 g (79%); mp 116.5–118° C.; IR(KBr, $\upsilon=cm^{-1}$) 3170, 1612, 1506, 1478, 1358, 1252, 1054; $^1H$ NMR (300 MHz, DMSO-$d_6$) δ 3.69 (3H, s), 3.81 (3H, s), 4.53 (2H, d, J=5.7 Hz), 5.16 (1H, t, J=5.7 Hz), 6.92 (1H, d, J=1.1 Hz), 7.01 (1H, d, J=8.5 Hz), 7.18 (1H, d, J=1.0 Hz), 7.50 (1H, dd, J=8.5 Hz, 2.2 Hz), 7.68 (1H, d, J=2.2 Hz); MS(DCl)m/z: 219 (MH+). Anal. calcd. for $C_{12}H_{14}N_2O_2$: C, 66.04; H, 6.47; N, 12.84. Found: C, 66.13; H, 6.09; N, 12.84.

EXAMPLE 64

2-Methoxy-5-(2-pyridinyl)benzenemethanol

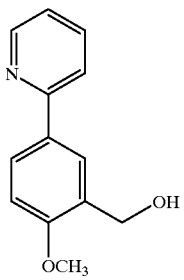

The 2-pyridinyl derivative was prepared in a similar manner, as described in Example 63.

mp 92–93° C.; IR(KBr, $\upsilon=cm^{-1}$)3324, 1584, 1562, 1436, 1272, 1042, 782; $^1H$ NMR (300 MHz, DMSO-$d_6$) δ 3.82 (3H, s), 4.56 (2H, d, J=5.7 Hz), 5.13 (1H, t, J=5.7 Hz), 7.02 (1H, d, J=8.6 Hz), 7.23–7.27 (1H, m), 7.77–7.86 (2H,m), 7.94 (1H, dd, J=8.6 Hz, 2,4 Hz), 8.17 (1H, d, J=2.3 Hz) 8.59 −8.62 (1H, m); MS(DCl)m/z: 216 (MH+). Anal. calcd. for $C_{13}H_{13}NO_2$: C, 72.54; H, 6.09; N, 6.51. Found: C,72.66; H, 6.01; N, 6.49.

EXAMPLES 65–67

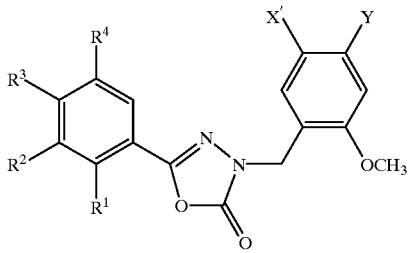

$XV^{65-67}$

EXAMPLE 65

3-[[2-Methoxy-5-(4-morpholinylmethyl)phenyl]methyl]-5-[4-trifluoromethyl)phenyl]-1,3,4-oxadiazol-2(3H)-one ($XV^{65}$: X'=morpholinylmethyl, Y=H, $R^1=R^2=R^4=H$, $R^3=CF_3$)

5-[4-(Trifluoromethyl)phenyl]-1,3,4-oxadiazol-2(3H)-one (1 g, 4.3 mmol), 2-methoxy-(4-morpholinylmethyl)benzyl alcohol (1.05 g, 4.3 mmol), and triphenylphosphene (1.1 g, 4.3 mmol) were dissolved in THF (100ml) at 0° C. under $N_2$. Diethylazodicarboxylate (0.68 ml, 4.3 mmol) was added dropwise and the solution stirred for 18 h at 24° C. Concentration on $SiO_2$, and elution with 20% THF/benzene gave 1.35 g (70%) crystallized from diethylether.

mp 124–125° C.; Anal. calcd. for $C_{22}H_{22}F_3N_3O_4$: C, 58.80; H, 4.93; N, 9.35. Found: C, 58.70; H, 4.81; N, 9.16.

The following oxadiazolones were prepared by a Mitsunobu procedure similar to Example 65.

EXAMPLE 66

3-[5-Chloro-4-[(ethylmethylamino)-2-methoxyphenyl]methyl]-5-[4-trifluoromethyl)phenyl]-1,3,4-oxadiazol-2(3H)-one ($XV^{66}$: X'=ethylmethylamino, Y=H, $R^1=R^2=R^4=H$, $R^3=CF_3$)

mp 105–107° C.; Anal. calcd. for $C_{20}H_{19}ClF_3N_3O_3$: C, 54.37; H, 4.33; N, 9.51. Found: C, 54.27; H, 4.32; N, 9.41.

EXAMPLE 67

3-[[2-Methoxy-5-(2-pyridinyl)phenyl]methyl]-5-[4-(trifluoromethyl)-phenyl]-1,3,4-oxadiazol-2(3H)-one ($XV^{67}$: X'=2-pyridinyl, Y=H, $R^1=R^2=R^4=H$, $R^3=CF_3$)

mp 165–166° C.; Anal. calcd. for $C_{22}H_{16}F_3N_3O_3$: C, 61.83; H, 3.77; N, 9.83. Found: C, 60.48; H, 3.87; N, 9.66.

EXAMPLES 68 AND 69

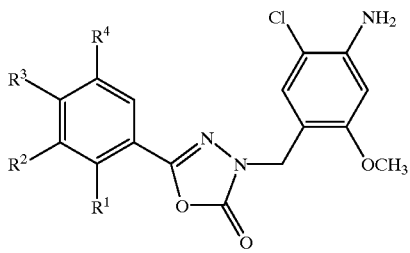

EXAMPLE 68

3-[(4-Amino-5-chloro-2-methoxyphenyl)methyl]-5-[3,4-dichlorophenyl]-1,3,4-oxadiazol-2(3H)-one (XVI[68]: $R^1=R^4=H$, $R^2=R^3=Cl$)

N-[2-Chloro-4-[[1,5-dihydro-5-oxo-3-[3,4-dichlorophenyl]-1,2,4-oxadiazol-1-yl]methyl]-5-methoxyphenyl]acetamide (1 g, 2,45 mmol) was taken up in absolute ethanol (110 ml) and concentrated HCl solution (11 ml) added and the reaction mixture heated at reflux for 1 h. The solvent was removed by rotary evaporation and the residue taken up in ethyl acetate (some THF added to dissolve) and washed with NaHCO$_3$ solution, brine, and dried (MgSO$_4$). Concentration gave 903 mg (92%). mp 196–197.5° C.; $^1$H NMR (300 MHz, DMSO-d$_6$) δ 3.69 (3H, s), 4.74 (2H, s), 6.57 (1H, s), 6.68 (3H, Br.s), 7.17 (1H, s), 7.70 (1H, dd, J=8.4 Hz, 1.9 Hz), 7.77 (1H, d, J=8.4 Hz), 7.89 (1H, d, J=1.9 Hz). $^{13}$CNMR (75 MHz, DMSO-d$_6$) δ 156.70, 152.43, 150.49. 144.06, 134.23, 132.23, 131.65, 130.15, 126.90, 125.41, 124.04, 112.81, 109.16, 99.40, 55.63, 44.06; MS(DCl)m/z: 400(MH$^+$).

EXAMPLE 69

3-[(4-Amino-5-chloro-2-methoxyphenyl)methyl]-5-[4-(trifluoromethyl)-phenyl]-1,3,4-oxadiazol-2(3H)-one, Hydrochloride Salt (XVI[69]: $R^1=R^2=R^4=H$, $R^3=CF_3$)

The title aniline was prepared in a similar manner to Example 68.

mp>190° C. (dec); Anal. calcd. for $C_{17}H_{13}ClF_3N_3O_3 \cdot 1.0$ HCl: C, 46.81; H, 3.24; N, 9.63. Found: C, 46.97; H, 3.19; N, 9.54.

EXAMPLES 70–74

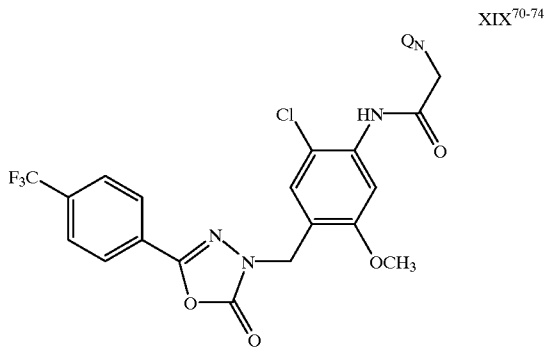

EXAMPLE 70

2-Bromo-N-[2-chloro-4-[[2,3-dihydro-2-oxo-5-[4-(trifluoromethyl)phenyl]-1,3,4-oxadizol-3-yl]methyl]-5-methoxyphenyl]acetamide (XIX[70]: $Q_N=Br$)

3-[(4-Amino-5-chloro-2-methoxyphenyl)methyl]-5-[4-(trifluoromethyl) phenyl]-1,3,4-oxadiazol-2(3H)-one (3 g, 7.5 mmol) and pyridine (0.68 ml, 8.41 mmol) were dissolved in THF (35 ml) under N$_2$ and cooled to 0° C. Bromoacetyl bromide (0.72 ml, 8.26 mmol) was added dropwise and the reaction mixture stirred for 18 h at 24° C. before being partitioned between ethyl acetate (400 ml) and 0.1N HCl solution (50 ml). The organic phase was washed with saturated NaHCO$_3$ solution and brine, and dried over MgSO$_4$. Active carbon (500 mg) was added and the solution filtered through a plug of Celite. Concentration gave 3.8 g (98%); mp 140–182° C. (dec); IR(KBr, υ=cm$^{-1}$) 3348, 2972, 1784, 1672, 1594, 1234, 1168, 1066; $^1$H NMR (300 MHz, DMSO-d$_6$) δ 3.77 (3H, s), 4.15 (2H, s), 4.90 (2H, s), 7.47–7.48 (2H, m), 7.86 (2H, d, J=8.4 Hz), 7.96 (1H, d, J=8.3 Hz), 9.30 (1H, s); MS(ESI)m/z: 520(MH$^+$); Anal. calcd. for $C_{18}H_{14}BrClF_3N_3O_4$: C, 43.83; H, 2.71; N, 8.07. Found: C, 43.68; H, 2.54; N, 7.77.

EXAMPLE 71

N-[2-Chloro-4-[[2,3-dihydro-2-oxo-5-[4-(trifluoromethyl)phenyl]-1,3,4-oxadiazol-3-yl]methyl]-5-methoxyphenyl]-4-morpholineacetamide (XIX[71]: $Q_N=$morpholine)

2-Bromo-N-[2-Chloro-4-[[1,5-dihydro-5-oxo-3-[4-(trifluoromethyl)phenyl]-1,2,4-oxadizol-1-yl]methyl]-5-hydroxyphenyl] acetamide (1 g, 1.9 mmol), morpholine (167 mg, 1.9 mmol), potassium carbonate (262 mg, 1.9 mmol) and Kl (78 mg) were dissolved in acetonitrile (100 ml) and heated at reflux for 3.5 h. The reaction mixture was filtered, concentrated by rotary evaporation, and the residue taken up in ethyl acetate and washed with water and brine. Recrystallization from acetonitrile gave 900 mg (90%). mp 178–179° C.; IR(KBr, υ=cm$^{-1}$) 3434, 2848, 1772, 1696, 1528, 1324, 1118; $^1$H NMR (300 MHz, DMSO-d$_6$) 67 2.56 (4H, br. s), 3.18 (2H, s), 3.65 (4H, t, J=4.3 Hz), 3.78 (3H, s), 4.88 (2H, s), 7.50 (1H, s), 7.88 (2H, d, J=8.5 Hz), 7.96 (2H, d, J=8.4 Hz), 8.04 (1H, s), 9.94 (1H, s); MS(ESI)m/z: 527 (MH$^+$); Anal. calcd. for $C_{23}H_{22}ClF_3N_4O_5$: C, 52,43; H, 4.21; N, 10.63. Found: C, 52.31; H, 4.08; N, 10.56.

The compounds of Examples 72–74 were prepared in a manner similar to that of Example 71.

EXAMPLE 72

N-[2-Chloro-4-[[2,3-dihydro-2-oxo-5-[4-(trifluoromethyl)phenyl]-1,3,4-oxadiazol-3-yl]methyl]-5-methoxyphenyl]-4-methyl-1-piperazineacetamide (XIX[72]: $Q_N=$N-methylpiperazine)

mp 190.5–192.5° C.; Anal. calcd. for $C_{24}H_{25}ClF_3N_5O_4$: C, 53.39; H, 4.67; N, 12.97. Found: C, 53.34; H, 4.72; N, 12.80.

EXAMPLE 73

N-[2-Chloro-4-[[2,3-dihydro-2-oxo-5-[4-(trifluoromethyl)phenyl]-1,3,4-oxadiazol-3-yl]methyl]-5-methoxyphenyl]-4-phenyl-1-piperazineacetamide (XIX[73]: $Q_N=$N-phenylpiperazine)

mp 228–230° C.; Anal. calcd. for $C_{29}H_{27}ClF_3N_5O_4$: C, 57.89; H, 4.52; N, 11.63. Found: C, 57.90; H, 4.54; N, 11.59.

EXAMPLE 74

N-[2-Chloro-4-[[2,3-dihydro-2-oxo-5-[4-(trifluoromethyl)phenyl]-1,3,4-oxadiazol-3-yl]methyl]-5-methoxyphenyl]-2-(dimethylamino)acetamide (XIX[74]: $Q_N=$dimethylamine)

mp 140.5–143.5° C.; Anal. calcd. for $C_{21}H_{20}ClF_3N_4O_4 \cdot 0.1\ H_2O$: C, 51.81; H, 4.19; N, 11.51. Found: C, 51.42; H, 4.24; N, 10.90.

EXAMPLE 75

3-[(5-Chloro-2-methoxyphenyl)methyl]-5-[4-trifluoromethyl)phenyl]-1,3,4-oxadiazol-2(3H)-thione (XVIII[75])

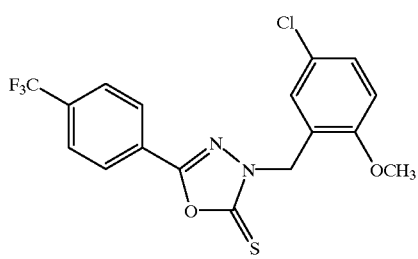

XVIII[75]

3-(5-Chloro-2-methoxyphenyl)-5-[4-(trifluoromethyl)phenyl]-1,3,4-oxadiazol-2(3H)-one (1 g, 2.7 mmol) and Lawesson's reagent (800 mg, 1.98 mmol) were heated at reflux in toluene (50 ml) for 18 h. An additional 400 mg of reagent was added and the reaction heated at reflux 48 h. Concentration on $SiO_2$ and elution with 10% ethyl acetate/hexanes gave an oil. Crystallization occurred upon standing in diethylether/ethyl acetate and gave 800 mg (77%). mp 158–159° C.; IR(KBr, $\upsilon = cm^{-1}$) 3456, 1608, 1492, 1450, 1332, 1318, 1250, 1166, 1112; $^1$H NMR (300 MHz, DMSO-$d_6$) δ 3.82 (3H, s), 5.27 (2H, s), 7.08 (1H, d, J=8.6 Hz), 7.34–7.40 (2H, m), 7.93 (2H, d, J=8.5 Hz), 8.07 (2H, d, J=8.3 Hz); MS(DCl)m/z: 401 (MH$^+$); Anal. calcd. for $C_{17}H_{12}ClF_3N_2O_2S$: C, 50.94; H, 3.02; N, 6.99. Found: C, 50.87; H, 3.00; N, 7.04.

EXAMPLES 76 AND 77

XX[76-77]

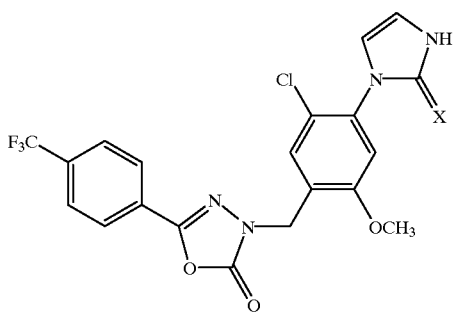

EXAMPLE 76

3-[[5-Chloro-4-(2,3-dihydro-2-oxo-1H-imidazol-1-yl)-2-methoxyphenyl]-methyl]-5-[4-(trifluoromethyl)phenyl]-1,3,4-oxadiazol-2(3H)-one (XX[76]: X=O)

3-[(4-Amino-5-chloro-2-methoxyphenyl)methyl]-5-[4-(trifluoromethyl) phenyl]-1,3,4-oxadiazol-2(3H)-one (1.14 g, 2.9 mmol) and triethylamine (1.0 ml, 6.8 mmol) were taken up in anhydrous THF (20 ml) and transferred dropwise by cannula into a 20% solution of phosgene in toluene at 0° C. under $N_2$. The reaction was stirred 2.5 h at 24° C., diluted with diethylether (1 vol), and filtered through a celite plug. Concentrated by rotary evaporation to gave a solid which was dissolved in dichloromethane (50 ml) under $N_2$ and aminoacetaldehyde (0.42 ml, 2.9 mmol) was added. The solution was stirred 3 h and concentrated to remove solvent. The residue was taken up in 25 ml of formic acid (88%) and stirred 18 h at 24° C. The formic acid was removed by rotary evaporation the residue taken up in ethyl acetate, washed with saturated $NaHCO_3$ solution and brine, and dried. Concentration on $SiO_2$, and elution with 45% THF/benzene gave 850 mg (65%). mp 201–202° C.; IR(KBr, $\upsilon = cm^{-1}$)3414, 1792, 1694, 1330, 1236, 1136; $^1$H NMR(300 MHz, CDCl$_3$) δ 3.86 (3H, s), 4.97 (2H, s), 6.38 (2H, br. s), 6.99 (1H, s), 7.40 (1H, s), 7.71 (2H, d, J=8.4 Hz), 7.94 (2H, d, J=8.2 Hz), 10.28 (1H, br. s); MS(ESI)m/z: 465 (M-H$^-$); Anal. calcd. for $C_{20}H_{14}ClF_3N_4O_4 \cdot 0.1\ H_2O$: C, 51.20; H, 3.06; N, 11.94. Found: C, 51.18; H, 3.10; N, 11.99.

EXAMPLE 77

3-[[5-Chloro-4-(2,3-dihydro-2-thio-1H-imidazol-1-yl)-2-methoxyphenyl]-methyl]-5-[4-(trifluoromethyl)phenyl]-1,3,4-oxadiazol-2(3H)-one (XX[77]: X=S)

The title compound was prepared in a similar manner to Example 76 using thiophosgene in place of phosgene.

mp 184–185° C.; Anal. calcd. for $C_{20}H_{14}ClF_3N_4O_3S$: C, 49.75; H, 2.92; N, 11.60. Found: C, 49.56; H, 2.82; N, 11.53.

EXAMPLES 78–80

XVI[78-80]

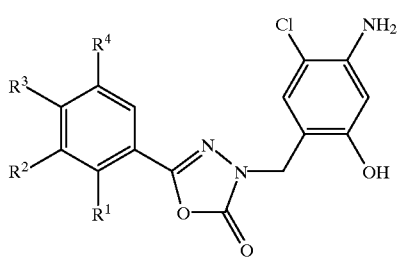

EXAMPLE 78

3-[(4-Amino-5-chloro-2-hydroxyphenyl)methyl]-5-[3,4-dichlorophenyl]-1,3,4-oxadiazol-2(3H)-one (XVI[78]: $R^1=R^4=H$, $R^2=R^3=Cl$)

3-[(4-Amino-5-chloro-2-methoxyphenyl)methyl]-5-[3,4-dichlorophenyl]-1,3,4-oxadiazol-2(3H)-one (903 mg, 2.25 mmol) was taken up in dichloromethane (55 ml) and cooled to 0° C. under $N_2$ and 12 ml of boron tribromide (1.0 M in $CH_2Cl_2$) was added. The reaction mixture was stirred for 18 h at 24° C. and poured dropwise into 200 ml of saturated $NaHCO_3$ solution at 0° C. with rapid stirring. The product was extracted with ethyl acetate (some THF added for solubility), washed with brine, and dried over $MgSO_4$. Trituration with boiling methanol gave 853 mg (97%); mp 202–203° C.; IR(KBr, $\upsilon=cm^{-1}$) 3364, 3296, 1804, 1166, 738; $^1$H NMR (300 MHz, DMSO-$d_6$) δ 4.72 (2H, s), 5.31 (2H, s), 6.29 (1H, s), 7.04 (1H, s), 7.71 (1H, dd, J=8.4 Hz, 2.0 Hz), 7.78 (1H, d, J=8.4 Hz), 7.90 (1H, d, J=1.9 Hz), 9.57 (1H, s); MS(ESI)m/z: 384 (M-H$^-$); Anal. calcd. for $C_{15}H_{10}Cl_3N_3O_3$: C, 46.60; H, 2.61; N, 10.87. Found: C, 46.56; H, 2.52; N, 10.62.

The following phenols, Examples 79 through 107, were prepared by the $BBr_3$ method of example 78.

EXAMPLE 79

3-[[4-(Amino)-5-chloro-2-hydroxyphenyl]methyl]-5-[3,5-dichlorophenyl]-1,3,4-oxadiazol-2(3H)-one ($XVI^{79}$: $R^1=R^3=H$, $R^2=R^4=Cl$)

mp 219–220° C.; Anal. calcd. for $C_{15}H_{10}Cl_3N_3O_3$: C, 46.60; H, 2.61; N, 10.87. Found: C, 46.49; H, 2.80; N, 10.65.

EXAMPLE 80

3-[(4-Amino-5-chloro-2-hydroxyphenyl)methyl]-5-[4-(trifluoromethyl)-phenyl]-1,3,4-oxadiazol-2(3H)-one ($XVI^{180}$: $R^1=R^2=R^4=H$, $R^3=CF_3$)

mp 210–212° C.; Anal. calcd. for $C_{16}H_{11}ClF_3N_3O_3 \cdot 0.1$ $H_2O$; $0.1$ $CH_3CN$: C, 49.68; H, 2.96; N, 11.09. Found: C, 49.68; H, 2.73; N, 10.99.

EXAMPLES 81–87

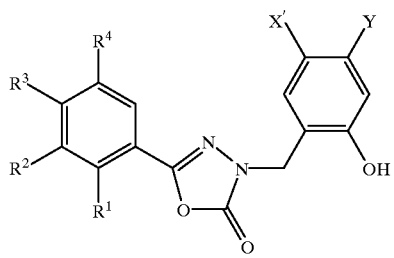

$XV^{81-87}$

EXAMPLE 81

3-[2-Hydroxyphenyl)methyl]-5-[4-(trifluoromethyl]phenyl]-1,3,4-oxadiazol-2(3H)-one ($XV^{81}$: X'=H, Y=H, $R^1=R^2=R^4=H$, $R^3=CF_3$)

mp 181–182° C.; Anal. calcd. for $C_{16}H_{11}F_3N_2O_3$: C, 57.15; H, 3.30; N, 8.33. Found: C, 57.14; H, 3.35; N, 8.19.

EXAMPLE 82

3-[(5-Chloro-2-hydroxyphenyl)methyl]-5-[4-(trifluoromethyl)phenyl]-1,3,4-oxadiazol-2(3H)-one ($XV^{82}$: X'=Cl, Y=H, $R^1=R^2=R^4=H$, $R^3=CF_3$)

mp 217–218° C.; Anal. calcd. for $C_{16}H_{10}ClF_3N_2O_3$: C, 51.84; H, 2.72; N, 7.56. Found: C, 51.88; H, 2.58; N, 7.57.

EXAMPLE 83

3-[[2-Hydroxy-5-chlorophenyl]methyl]-5-[3,5-bis(trifluoromethyl)phenyl]-1,3,4-oxadiazol-2(3H)-one ($XV^{83}$: X'=Cl, Y=H, $R^1=R^3=H$, $R^3=R^4=CF_3$)

mp 171–172° C.; Anal. calcd. for $C_{17}H_9ClF_6N_2O_3$: C, 46.54; H, 2.07; N, 6.39. Found: C, 46.82; H, 2.07; N, 6.30.

EXAMPLE 84

3-[(5-Chloro-2-hydroxyphenyl)methyl]-5-[4-fluoro-3-(trifluoromethyl)-phenyl]-1,3,4-oxadiazol-2(3H)-one ($XV^{84}$: X'=Cl, Y=H, $R^1=R^4=H$, $R^2=CF_3$, $R^4=F$)

mp 163.5–165.5° C.; Anal. calcd. for $C_{16}H_9ClF_4N_2O_3$: C, 49.44; H, 2.30; N, 7.21. Found: C, 49.15; H, 2.16; N, 7.17.

EXAMPLE 85

3-[[2-Hydroxy-5-chlorophenyl]methyl]-5-[2-chloro-5-(trifluoromethyl)-phenyl]-1,3,4-oxadiazol-2(3H)-one ($XV^{85}$: X'=Cl, Y=H, $R^1=Cl$, $R^2=R^3=H$, $R^4=CF_3$)

mp 177–179° C.; Anal. calcd. for $C_{16}H_9Cl_2F_3N_2O_3$: C, 47.43; H, 2.24; N, 6.91. Found: C, 47.40; H, 2.24; N, 6.96.

EXAMPLE 86

3-[[2-Hydroxy-5-chlorophenyl]methyl]-5-[3,5-dichlorophenyl]-1,3,4-oxadiazol-2(3H)-one ($XV^{86}$: X'=Cl, Y=H, $R^1=R^3=H$, $R^2=R^4=Cl$)

mp 207–209° C.; Anal. calcd. for $C_{15}H_9Cl_3N_2O_3$: C, 48.48; H, 2,44; N, 7.54. Found: C, 48.51; H, 2.37; N, 7.61.

EXAMPLE 87

3-[(5-Chloro-2-hydroxyphenyl)methyl]-5-[2-fluoro-4-(trifluoromethyl)-phenyl]-1,3,4-oxadiazol-2(3H)-one ($XV^{87}$: X'=Cl, Y=H, $R^1=F$, $R^2=R^4=H$, $R^3=CF_3$)

mp 202–204.5° C.; Anal. calcd. for $C_{16}H_9ClF_4N_2O_3 \cdot 0.1$ EtOAc: C, 49.55; H, 2,49; N, 7.05. Found: C, 49.57; H, 2.51; N, 6.91.

EXAMPLES 88 AND 89

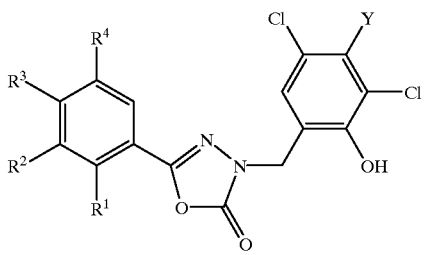

$XVII^{88-89}$

EXAMPLE 88

3-[(4-Acetylamino)-3,5-dichloro-2-hydroxyphenyl)methyl]-5-[3,4-dichlorophenyl]1,3,4-oxadiazol-2(3H)-one ($XVII^{88}$: Y=NHAc, $R^1=R^4=H$, $R^2=R^3=Cl$)

3-[[4-(Acetylamino)-5-chloro-2-methoxyphenyl]methyl]-5-[3,4-dichlorophenyl]-1,3,4-oxadiazol-2(3H)-one (2 g, 4.3 mmol) was taken up in dichloromethane (75 ml) and cooled to 0° C. under $N_2$ and 20 ml of boron tribromide (1.0 M in $CH_2Cl_2$) was added. The reaction mixture was stirred for 18 h at 24° C. and poured dropwise into 250 ml of saturated $NaHCO_3$ solution at 0° C. with rapid stirring. The product was extracted with ethyl acetate and THF (added for solubility), washed with brine, and dried over $MgSO_4$ gave 1.9 g (98%).

The resulting phenol (1 g, 2.3 mmol) was taken up in toluene (150 ml) and catalytic diisobutylamine (3.5 µl) added followed by sulfuryl chloride (0.3 ml, 3.7 mmol). The solution was heated at 68° C. over a period of 72 h during which time additional sulfuryl chloride (1.63 ml, 20.3 mmol) was added until the reaction was complete. The precipitate was filtered, washed with toluene, and dried to give 879 mg (81%). Recrystallization gave: mp 246–247° C.; IR(KBr, υ=cm$^{-1}$) 3379, 3231, 1780, 1657, 1473, 1409, 1134; $^1$H NMR (300 MHz, DMSO-$d_6$) δ 2.05 (3H, s), 4.97 (2H, s), 7.45 (1H, s), 7.73–7.81 (2H, m), 7.92–7.96 (1H, 9.81 (1H, s), 10.01 (1H, s); MS(ESI)m/z: 460 (M–H$^-$). Anal. calcd. for $C_{17}H_{11}Cl_4N_3O_4 \cdot 0.05$ $H_2O$: C,44.01; H, 2,41; N, 9.06. Found: C, 43.85; H, 2.33; N, 9.23.

The chlorination was performed according to the procedure described in R. A. Sheldon, etal. *Tet. Lett.* 36, 3893 (1995).

EXAMPLE 89

3-[(4-Amino-3,5-dichloro-2-hydroxyphenyl)methyl]-5-[3,4-dichlorophenyl]1,3,4-oxadiazol-2(3H)-one (XVII[89]: Y=NH$_2$, R$^1$=R$^4$=H, R$^2$=R$^3$=Cl)

3-[(4-Acetylamino)-3,5-dichloro-2-hydroxyphenyl)methyl]-5-[3,4-dichlorophenyl]-1,3,4-oxadiazol-2(3H)-one (521 mg, 1.1 mmol) was taken up in absolute ethanol (60 ml) and concentrated HCl solution (12 ml) was added. The solution was heated at reflux over a period of 22 h during which time additional hydrochloric acid (6 ml) was added until the reaction was complete. After cooling, the precipitate was filtered and dried to give 299 mg (63%); mp 200.5–202° C.; IR(KBr, υ=cm$^{-1}$) 3343, 1780, 1609, 1447, 1289, 1214, 1166; $^1$H NMR (300 MHz, DMSO-d$_6$) δ 4.83 (2H, s), 5.48 (2H, s), 7.17 (1H, s), 7.69–7.73 (1H, m), 7.75–7.78 (1H, m), 7.90–7.81 (1H, m), 9.49 (1H, s). MS(ESI)m/z: 418 (M-H$^-$). Anal. calcd. for C$_{15}$H$_9$Cl$_4$N$_3$O$_4$: C, 42.79; H, 2.16; N, 9.98; Cl, 33.68. Found: C, 42.71; H, 2.09; N, 9.77; Cl, 34.11.

EXAMPLES 90 AND 91

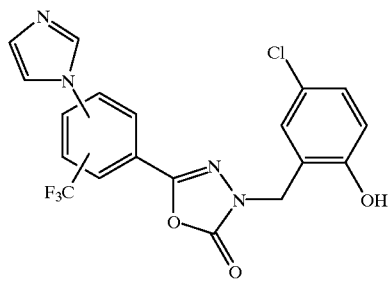

XVIII[90-91]

EXAMPLE 90

3-[(5-Chloro-2-hydroxyphenyl)methyl]-5-[2-(1H-imidazol-1-yl)-4-(trifluoromethyl)phenyl]-1,3,4-oxadiazol-2(3H)-one (XVIII[90]: 2-Im, 4-CF$_3$)

mp 242–243° C.; Anal. calcd. for C$_{19}$H$_{12}$F$_3$N$_4$O$_3$: C, 52.25; H, 2.77; N, 12.83. Found: C, 51.99; H, 2.72; N, 12,46.

EXAMPLE 91

3-[(5-Chloro-2-hydroxyphenyl)methyl]-5-[4-(1H-imidazol-1-yl)-3-(trifluoromethyl)phenyl]-1,3,4-oxadiazol-2(3H)-one (XVIII[91]: 4-Im, 3-CF$_3$)

mp 178–180° C.; Anal. calcd. for C$_{19}$H$_{12}$F$_3$N$_4$O$_3$.0.25 H$_2$O;.0.1 EtOAc: C, 51.77; H, 2.98; N, 12,45. Found: C, 51.60; H, 2.73; N, 12,44.

EXAMPLES 92–98

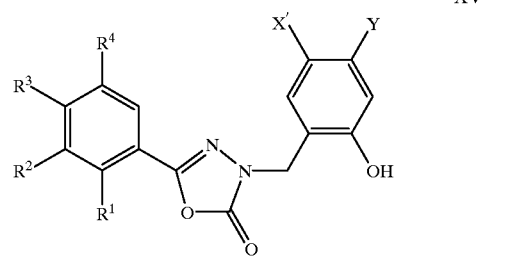

XV[92-98]

EXAMPLE 92

3-[[2-Hydroxy-5-(4-morpholinylmethyl)phenyl]methyl]-5-[4-trifluoromethyl)phenyl]-1,3,4-oxadiazol-2(3H)-one (XV[92]: X'=morpholinylmethyl, Y=H, R$^1$=R$^2$=R$^4$=H, R$^3$=CF$_3$) Foam.

Anal. calcd. for C$_{21}$H$_{20}$F$_3$N$_3$O$_4$.0.1 H$_2$O; .0.2 C$_6$H$_6$: C, 58.94; H, 4.32; N, 9.34. Found: C, 58.97; H, 4.44; N, 8.86.

EXAMPLE 93

3-[5-Chloro-4-[(ethylmethylamino)-2-hydroxyphenyl]methyl]-5-[4-trifluoromethyl)phenyl]-1,3,4-oxadiazl-2(3H)-one (XV[93]: X'=ethylmethylamino, Y=H, R$^1$=R$^2$=R$^4$=H, R$^3$=CF$_3$)

mp 132–133° C.; Anal. calcd. for C$_{19}$H$_{17}$ClF$_3$N$_3$O$_3$: C, 53.34; H, 4.01; N, 9.82. Found: C, 53.09; H, 3.90; N, 9.82.

EXAMPLE 94

3-[[2-Hydroxy-5-(2-pyridinyl)phenyl]methyl]-5-[4-(trifluoromethyl)phenyl]-1,3,4-oxadiazol-2(3H)-one (XV[94]: X'=2-pyridinyl, Y=H, R$^1$=R$^2$=R$^4$=H, R$^3$=CF$_3$)

mp 198–200° C.; Anal. calcd. for C$_{21}$H$_{14}$F$_3$N$_3$O$_3$.1.0 H$_2$O; .1.0 HCl: C, 53.91; H, 3.66; N, 8.98. Found: C, 53.65; H, 3.55; N, 9.00.

EXAMPLE 95

3-[[5-(1-Methyl-1H-imidazol-2-yl)-2-hydroxyphenyl]methyl-5-[4-(trifluoromethyl)phenyl]-1,3,4-oxadiazol-2(3H)-one (XV[95]: X'=1-methyl-1H-imidazol-2-yl, Y=H, R$^1$=R$^2$=R$^4$=H, R$^3$=CF$_3$)

mp 177–180° C.; Anal. calcd. for C$_{20}$H$_{15}$F$_3$N$_4$O$_3$.0.15 H$_2$O: C, 57.32; H, 3.68; N, 13.37. Found: C, 57.48; H, 3.66; N, 12.95.

EXAMPLE 96

3-[[2-hydroxy-5-(1-methyl-1H-imidazo-2-yl)phenyl]methyl]-5-[3,5-bis(trifluoromethyl)phenyl]-1,3,4-oxadiazol-2(3H)-one (XV[96]: X'=1-methyl-1H-imidazol-2-yl, Y=H, R$^1$=R$^3$=H, R$^2$=R$^4$=CF$_3$)

mp 203–206° C.; Anal. calcd. for C$_{21}$H$_{14}$F$_6$N$_4$O$_3$.0.1 H$_2$O: C, 51.82; H, 2.96; N, 11.51. Found: C, 51.63; H, 2.94; N, 11.50.

EXAMPLE 97

3-[[2-Hydroxy-5-(1H-imidazol-1-yl)phenyl]methyl]-5-[4-(trifluoromethyl)-phenyl]-1,3,4-oxadiazol-2(3H)-one (XV[97]: X'=1H-imidazol-1-yl, Y=H, R$^1$=R$^2$=R$^4$=H, R$^3$=CF$_3$)

Anal. calcd. for $C_{19}H_{13}F_3N_4O_3$: C, 56.72; H, 3.26; N, 13.93. Found: C, 56.63; H, 3.22; N, 13.90.

EXAMPLE 98

3-[[2-Hydroxy-5-(1H-imidazol-1-yl)phenyl]methyl]-5-[3,5-bis(trifluoro-methyl)phenyl]-1,3,4-oxadiazol-2(3H)-one ($XV^{98}$: X'=1H-imidazol-1-yl, Y=H, $R^1=R^3=H$, $R^2=R^4=CF_3$)

mp 209–211° C.; Anal. calcd. for $C_{20}H_{12}F_6N_4O_3$: C, 51.07; H, 2.57; N, 11.91. Found: C, 50.87; H, 2,44; N, 12.01.

EXAMPLES 99–106

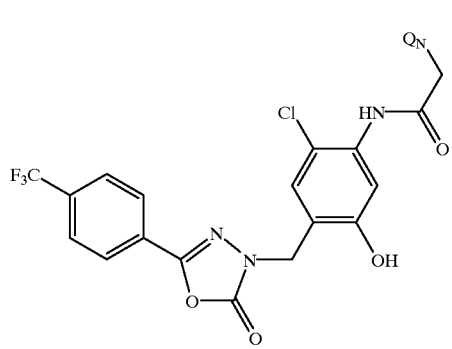

$XX^{99-106}$

EXAMPLE 99

N-[2-Chloro-4-[[1,5-dihydro-5-oxo-3-[4-(trifluoromethyl)phenyl]-1,2,4-oxadiazol-1-yl]methyl]-5-hydroxyphenyl]-4-morpholineacetamide ($XX^{99}$: $Q_N$=morpholine)

mp 240–2410° C.; Anal. calcd. for $C_{22}H_{20}ClF_3N_4O_5$: C, 51.52; H, 3.93; N, 10.92. Found: C, 51.49; H, 3.91; N, 10.80.

EXAMPLE 100

N-[2-Chloro-4-[[(2,3-dihydro-2-oxo-5-[4-(trifluoromethyl)phenyl]-1,3,4-oxadiazol-3-yl]methyl]-5-hydroxyphenyl]-4-thiomorpholineacetamide ($XX^{100}$: $Q_N$=thiomorpholine)

mp 250–252° C.; Anal. calcd. for $C_{22}H_{20}ClF_3N_4O_4S$: C, 49.96; H, 3.81; N, 10.59 Found: C, 50.15; H, 3.96; N, 10.35.

EXAMPLE 101

N-[2-Chloro-4-[[2,3-dihydro-2-oxo-5-[4-(trifluoromethyl)phenyl]-1,3,4-oxadiazol-3-yl]methyl]-5-hydroxyphenyl]-4-methyl-1-piperazineacetamide, dihydrochloride salt ($XX^{101}$: $Q_N$=N-methylpiperazine)

mp >220° C. (dec). Anal. calcd. for $C_{23}H_{23}ClF_3N_5O_4$.2.06 HCl; .0.7 EtOH; .0.2 $H_2O$: C, 46.02; H, 4.70; N, 11.00. Found: C, 45.97; H, 4.67; N, 10.77.

EXAMPLE 102

N-[2-Chloro-4-[1,2,3-dihydro-2-oxo-5-[4-(trifluoromethyl)phenyl]-1,3,4-oxadiazol-3-yl]methyl]-5-hydroxyphenyl]-4-phenyl-1-piperazineacetamide, dihydrochloride salt ($XX^{102}$: $Q_N$=N-phenylpiperazine)

mp 220–235° C.; Anal. calcd. for $C_{28}H_{25}ClF_3N_5O_4$.1.75 HCl; .0.15 $H_2O$: C,51.53; H, 4.17; N, 10.73. Found: C, 51.81; H, 4.33; N, 9.92.

EXAMPLE 103

N-[2-Chloro-4-[[2,3-dihydro-2-oxo-5-[4-(trifluoromethyl)phenyl]-1,3,4-oxadiazol-3-yl]methyl]-5-hydroxyphenyl]-4-benzyl-1-piperazineacetamide ($XX^{103}$: $Q_N$=N-benzylpiperazine)

mp 187.5–190° C.; Anal. calcd. for $C_{29}H_{27}ClF_3N_5O_4$: C, 57.86; H, 4.52; N, 11.63. Found: C, 57.89; H, 4.36; N, 11.53.

EXAMPLE 104

N-[2-Chloro-4-[[2,3-dihydro-2-oxo-5-[4-(trifluoromethyl)phenyl]-1,3,4-oxadiazol-3-yl]methyl]-5-hydroxyphenyl]-2-(dimethylamino)acetamide, hydrochloride salt ($XX^{104}$: $Q_N$=dimethylamino)

mp>233° C. (dec). Anal. calcd. for $C_{20}H_{18}ClF_3N_5O_4$.1.0 HCl; 0.5 $H_2O$; .0.1 $Et_2O$: C, 46.79; H, 4.04; N, 10.70. Found: C, 46.53; H, 3.99; N, 10.64.

EXAMPLE 105

N-[2-Chloro-4-[[2,3-dihydro-2-oxo-5-(1,1'-biphenyl)-1,3,4-oxadiazol-3-yl]methyl]-5-hydroxyphenyl]-4-methyl-1-piperazineacetamide, bis-hydrochloride salt ($XX^{105}$: $CF_3$=Ph, $Q_N$=N-methylpiperazine)

mp 244–247° C.; Anal. calcd. $C_{28}H_{28}ClN_5O_4$.2.0 HCl; .0.34$H_2O$: C, 54.86; H, 5.05; N, 11.42. Found: C, 54.33; H, 4.93; N, 11.10.

EXAMPLE 106

N-[2-Chloro-4-[[2,3-dihydro-2-oxo-5-[naphth-2-yl]-1,3,4-oxadiazol-3-yl]methyl]-5-hydroxyphenyl]-4-morpholineacetamide, hydrochloride salt ($XX^{106}$: $CF_3$=benzo, $Q_N$=morpholine)

mp 170.5–176° C.; Anal. calcd. for $C_{25}H_{23}ClN_4O_5$.1.0 HCl; .0.5$H_2O$: C, 55.57; H, 4.66; N, 10.37. Found: C, 55.49; H, 4.59; N, 10.21.

EXAMPLE 107

3-[(5-Chloro-2-hydroxyphenyl)methyl]-5-[4-(trifluoromethyl)phenyl]-1,3,4-oxadiazol-2(3H)-thione ($XIX^{107}$)

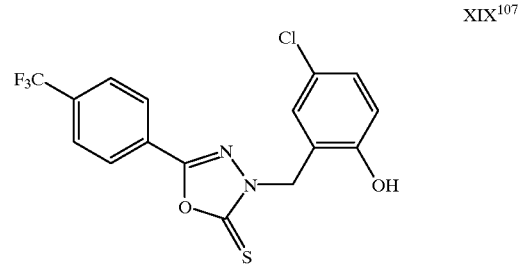

$XIX^{107}$ mp 192–194° C.; Anal. calcd. for $C_{16}H_{10}ClF_3N_2O_2S$: C, 49.69; H, 2.61; N, 7.24. Found: C, 49.82; H, 2.77; N, 7.14.

EXAMPLES 108 AND 109

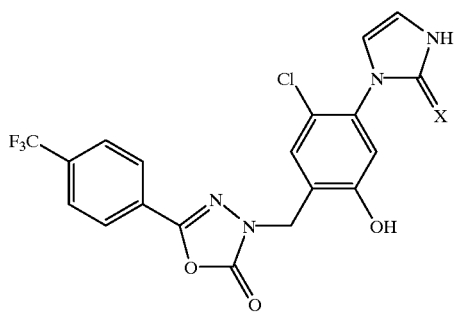

XXI[108-109]

EXAMPLE 108

3-[[5-Chloro-4-(2,3-dihydro-2-oxo-1H-imidazol-1-yl)-2-hydroxyphenyl]-methyl]-5-[4-(trifluoromethyl)phenyl]-1,3,4-oxadiazol-2(3H)-one (XXI[108]: X=O)

mp 231–233° C.; Anal. calcd. for $C_{19}H_{12}ClF_3N_4O_4$: C, 50.40; H, 2.67; N, 12.37. Found: C, 50.18; H, 2.66; N, 12.27.

EXAMPLE 109

3-[[5-Chloro-4-(2.3-dihydro-2-thio-1H-imidazol-1-yl)-2-hydroxyphenyl]-methyl]-5-[4-(trifluoromethyl)phenyl]-1,3,4-oxadiazol-2(3H)-one (XXI[109]: X=S)

mp 201–203° C.; Anal. calcd. for $C_{19}H_{12}ClF_3N_4O_3S$: C, 48.68; H, 2.58; N, 11.95. Found: C, 48.65; H, 2.54; N, 11.84.

Preparation No. 5

The starting oxadiazoles were prepared according to the procedure disclosed in D. H. Boschelli, et al. *J. Med. Chem.* 3, 1802 (1993).

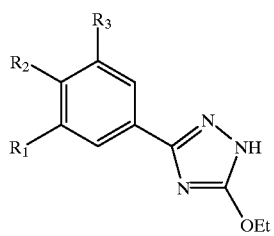

EXAMPLE 110

3-Ethoxy-5-[4-(trifluoromethyl)phenyl]-4H-1,2,4-triazole ($R_1$=$R_3$=H, $R_2$=$CF_3$)

5-[4-(Trifluoromethyl)phenyl]1,3,4-oxadiazol-2-amine (10 g, 44 mmol) and potassium hydroxide (7.4 g, 0.132 mol) dissoved in abs. ethanol (300 ml) were heated at reflux for 3 h. After being cooled to 24° C., the solution was neutralized with acetic acid and concentrated by rotary evaporation. The residue was taken up in ethyl acetate and washed with water and brine. Recrystallization from acetonitrile/ether (2:1) gave 9 g (82%); mp 151–152° C.; IR(KBr, υ=cm$^{-1}$) 2996, 1534, 1460, 1330, 1162, 1130, 1070; $^1$H NMR (300 MHz, DMSO-d$_6$) δ 1.35 (3H, t, J=7.1 Hz), 4.38 (2H, q, J=7.0 Hz), 7.82 (2H, d, J=8.3 Hz), 8.10 (2H, d, J=8.1 Hz), 13.64 (1H, br. s); MS(DCl)m/z: 258 (MH$^+$); Anal. calcd. for $C_{11}H_{10}F_3N_3O$: C, 51,37; H, 3.92; N, 16.34. Found: C, 51.40; H, 3.74; N, 16.28.

EXAMPLE 111

3-Ethoxy-5-[3,4-dichlorophenyl]-4H-1,2,4-triazole ($R_1$=$R_2$=Cl, $R_3$=H)

The title ethoxytriazole was prepared in a similar manner to Example 110.

mp 165–165.5° C.; Anal. calcd. for $C_{10}H_9Cl_2N_3O$: C, 46.54; H, 3.51; N, 16.28. Found: C, 46.49; H, 3.56; N, 16.34.

EXAMPLES 112–114

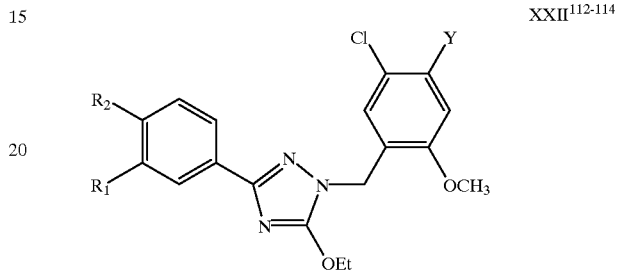

XXII[112-114]

EXAMPLE 112

N-[2-Chloro-4-[5-ethoxy-3-[[4-(trifluoromethyl)phenyl]methyl]-1H-1,2,4-triazol-1-yl]-methoxyphenyl]acetamide (XXII[112]: Y=NHAc, $R_1$=H, $R_2$=$CF_3$)

3-Ethoxy-5-[4-(trifluoromethyl)phenyl]-4H-1,2,4-triazole (1.76 g, 6.8 mmol) and N-[4-(bromomethyl)-2-chloro-5-methoxyphenyl]acetamide [JP 49049929] (2.0 g, 6.8 mmol) were dissolved in anhydrous DMF at 24° C. and 2 eqv. (408 mg, 14 mmol) of sodium hydride (80%) was added in portions under $N_2$. The reaction mixture was stirred 18 h and poured into water (2 vol) and extracted with ethyl acetate, washed with brine, and dried. Chromatography, elution with 20% THF/benzene gave gave 1.2 g (34%) of product, and 1.1 g (33%) of a regioisomer. IR(KBr, υ=cm$^{-1}$) 3298, 1664, 1560, 1326, 1160, 1114; $^1$H NMR(300 MHz, DMSO-d$_6$/CDCl$_3$) δ 1,39 (3H, t, J=7.1 Hz), 2.08 (3H, s), 3.75 (3H, s), 4.53 (2H,q, J=7.1 Hz), 5.07 (2H, s), 7.15 (1H, s), 7.47 (1H, s), 7.75 (2d, J=8.3 Hz), 8.07 (2H, d, J=8.1 Hz), 9.48 (1H, s); MS(ESI)m/z: 469 (MH$^+$). Anal. calcd. for $C_{21}H_{20}ClF_3N_4O_3$: C, 53.80; H, 4.30; N, 11.95. Found: C, 53.93; H, 4.44; N, 11.85.

The following products were prepared in a similar manner to Example 112.

EXAMPLE 113

N-[2-Chloro-4-[5-ethoxy-3-[[3,4-dichlorophenyl]methyl]-1H-1,2,4-triazol-1-yl]-methoxyphenyl]acetamide (XXII[113]: Y=NHAc, $R_1$=$R_2$=Cl).

mp 197–198° C.; Anal. calcd. for $C_{20}H_{19}Cl_3N_4O_3$: C,51.14; H, 4.08; N, 11.93. Found: C, 51.15; H, 4.17; N, 12.15.

EXAMPLE 114

1-[(5-Chloro-2-methoxyphenyl)methyl]-5-ethoxy-3-[4-(trifluoromethyl)-phenyl]-1H-1,2,4-triazole (XXII[114]: Y=H, $R_1$=H, $R_2$=$CF_3$).

mp 74–76° C.; Anal. calcd. for $C_{19}H_{17}ClF_3N_3O_2$: C, 55.42; H, 4.16; N, 10.20. Found: C, 55.80; H, 4.43, N; 9.65.

EXAMPLES 115–117

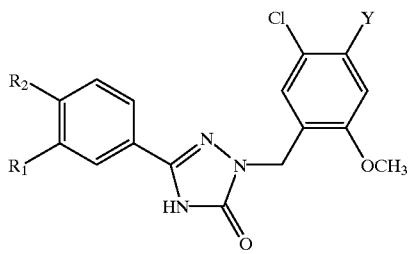

XXIII[115-117]

EXAMPLE 115

2-[(4-Amino-5-chloro-2-methoxyphenyl)methyl]-2, 4-dihydro-5-[4-(trifluoromethyl)phenyl]-3H-1,2,4-triazol-3-one (XXIII[115]: Y=NH$_2$, R$_1$=H, R$_2$=CF$_3$).

N-[2-Chloro-4-[5-ethoxy-3-[[4-(trifluoromethyl)phenyl]methyl]-1H-1,2,4-triazol-1-yl]-methoxyphenyl]acetamide (1.5 g, 3.2 mmol) was taken up in absolute ethanol (100 ml) and 10 ml concentrated HCl solution and heated at reflux for 20 min. Upon cooling a precipitate formed which was filtered and suspended in ethyl acetate (some THF added to dissolve) and washed with NaHCO$_3$ solution, brine, and dried (MgSO$_4$). mp>270° C. (subl); IR(KBr, υ=cm$^{-1}$) 3442, 3344, 1680, 1622, 1324, 1164, 1128, 1066; $^1$H NMR (300 MHz, DMSO-d$_6$) δ 3.70 (3H, s), 4.74 (2H, s), 5.36 (2H, s), 6.44 (1H, s), 6.89 (1H, s), 7.83 (2H, d, J=8.4 Hz), 7.95 (2H, d, J=8.2 Hz), 12,43 (1H, s); MS(ESI)m/z: 397 (M-H$^-$); Anal. calcd. for $C_{17}H_{14}ClF_3N_4O_2$.0.1 H$_2$O: C, 50.95; H, 3.58; N, 13.98. Found: C, 50.66; H, 3.71; N, 13.44.

The following triazolones were prepared in a similar manner to Example 115.

EXAMPLE 116

2-[(4-Amino-5-chloro-2-methoxyphenyl)methyl]-2, 4-dihydro-5-[3,4-dichlorophenyl]-3H-1,2,4-triazol-3-one (XXIII[116]: Y=NH$_2$, R$_1$=R$_2$=Cl)

mp 265–268° C.; Anal. calcd. for $C_{16}H_{13}Cl_3N_4O_2$: C, 48.08; H, 3.28; N, 14.02. Found: C, 48.71; H, 3.58; N, 13.08.

EXAMPLE 117

2-[(5-Chloro-2-methoxyphenyl)methyl]-2,4-dihydro-5-[4-(trifluoromethyl)-phenyl]-3H-1,2,4-triazol-3-one (XXIII[117]: Y=H, R$_1$=H, R$_2$=CF$_3$)

mp 245–246° C.; Anal. calcd. for $C_{17}H_{13}ClF_3N_3O_2$: C, 53.21; H, 3,41; N, 10.95. Found: C, 53.15; H, 3.39, N; 10.93.

The following phenols were prepared according to the BBr$_3$ method of Example 78.

EXAMPLES 118–120

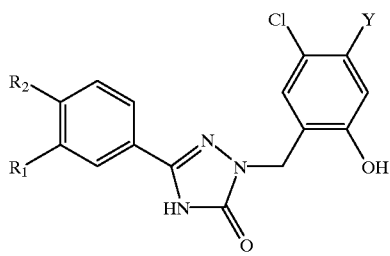

XXIII[118-120]

EXAMPLE 118

2-[(4-Amino-5-chloro-2-hydroxyphenyl)methyl]-2, 4-dihydro-5-[4-(trifluoromethyl)phenyl]-3H-1,2,4-triazol-3-one (XXIII[118]: Y=NH$_2$, R$_1$=H, R$_2$=CF$_3$)

Anal. calcd. for $C_{16}H_{12}ClF_3N_4O_2$.0.5 H$_2$O: C, 48.81; H, 3.33; N, 14.23. Found: C, 49.10; H, 3.42; N, 14.05.

EXAMPLE 119

2-[(4-Amino-5-chloro-2-hydroxyphenyl)methyl]-2, 4-dihydro-5-[3,4-dichlorophenyl]-3H-1,2,4-triazol-3-one (XXIII[119]: Y=NH$_2$, R$_1$=R$_2$=Cl)

mp 290–293° C.; Anal. calcd. for $C_{15}H_{11}Cl_3N_4O_2$.0.1 H$_2$O: C, 46.48; H, 2.92; N, 14.45. Found: C, 46.94; H, 2.84; N, 14.29.

EXAMPLE 120

2-[(5-Chloro-2-hydroxyphenyl)methyl]-2,4-dihydro-5-[4-(trifluoromethyl)-phenyl]-3H-1,2,4-triazol-3-one (XXIII[120]: Y=H, R$_1$=H, R$_2$=CF$_3$)

mp >280° C.; Anal. calcd. for $C_{16}H_{11}ClF_3N_3O_2$: C, 51.98; H, 3.00; N, 11.37. Found: C, 52.01; H, 3.04, N; 11.35.

Preparation No. 6

EXAMPLE 121

5-Chloro-3-[2-oxo-2-[4-(trifluoromethyl)phenyl]ethyl]-2(3H)-benzoxazolone (XXIV[121])

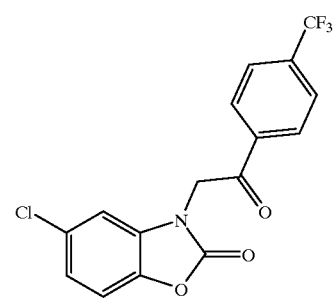

XXIV[121]

Bromine (0.67 ml, 13 mmol) was added dropwise to a solution of 4'-(trifluoromethyl)acetophenone (2.5 g, 13 mmol) in diethylether (20 ml) and 1,4-dioxane (10 ml) at room temperature. Chlorzoxazone (2.19 g, 13 mmol) was treated with sodium hydride (400 mg, 13 mmol) in DMF for 15 min. under $N_2$ and transferred by cannulation into the freshly prepared solution of bromide. The reaction mixture was stirred at 60° C. for 3 h, and poured into water (1 vol). The product was extracted with ethyl acetate, and the organic layer washed with water and brine and dried. Concentration gave a solid 4.4 g (93%) which was recrystallized from acetonitrile. mp 188–189° C.; IR(KBr, υ=cm$^{-1}$) 1776, 1704, 1330, 1226, 1122; $^1$H NMR (300 MHz, DMSO-d$_6$) δ 5.64 (2H, s), 7.20 (1H, dd, J=8.6 Hz, 2.1 Hz), 7.44 (1H, d, J=8.5 Hz), 7.57 (1H, d, J=2.1 Hz), 7.99 (2H, d, J=8.3 Hz), 8.27 (2H, d, J=8.1 Hz); MS(DCl)m/Z: 356 (MH$^+$) Anal. calcd. for $C_{16}H_9ClF_3NO_3$: C, 54.03; H, 2.55; N, 3.94. Found: C, 53.73; H, 2,43; N, 3.88.

EXAMPLE 122

1-(5-Chloro-2-hydroxyphenyl)-1,3-dihydro-4-[4-(trifluoromethyl)phenyl-2H-imidazol-2-one (XXV$^{122}$)

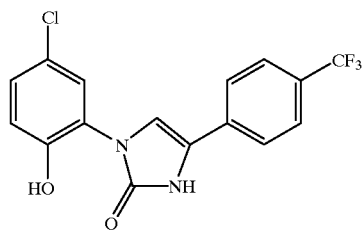

XXV$^{122}$

5-Chloro-3-[2-oxo-2-[4-(trifluoromethyl)phenyl]ethyl]-2(3 H)-benzoxazolone (1 g, 2.8 mmol) and ammonium acetate (2.1 g, 28 mmol) were taken up in acetic acid (100 ml) and heated at 100° C. for 2 h. The solution was poured into water (2 vol) and extracted into dichloromethane. Concentration gave a solid which was recrystallized from acetonitrile/AcOH(10:1). mp 278–279° C.; IR(KBr, υ=cm$^{-1}$)2980, 1668, 1624, 1498, 1328, 1170, 1136, 1066; $^1$H NMR (300 MHz, DMSO-d$_6$) δ 7.01 (1H, d, J=8.7 Hz), 7.26 (1H, dd, J=8.7 Hz, 2.6 Hz), 7.46 (1 d, J=2.6 Hz), 7.52 (1H, d, J=1.6 Hz), 7.72 (2H, d, J=8.6 Hz), 7.78 (2H, d, J=8.5 Hz), 10.27 (1H, s), 11.27 (1H, s); MS(ESI)m/z: 355 (MH$^+$). Anal. calcd. for $C_{16}H_{10}ClF_3N_2O_2$: C, 54.18; H, 2.84; N, 7.90. Found: C, 53.98; H, 2.89; N, 7.92.
Preparation No. 7

EXAMPLE 123

4-(Acetylamino)-5-chloro-2-methoxybenzoic acid, 4-(trifluoromethyl)-phenylhydrazide
(Y=NHAc, R$_1$=CF3, R$_2$=H)

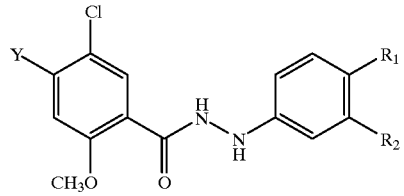

Iso-butylchloroformate (1.6 ml, 16.4 mmol) was added dropwise to a solution of 4-(acetylamino)-5-chloro-2-methoxybenzoic acid (4 g, 16.4 mmol) and 4-methylmorpholine (1.8 ml, 16.4mmol) in 400 ml of anhydrous THF at 0° C. and stirred for 0.5 h at room temperature before addition of 4-(trifluoromethyl)phenylhydrazine (2.9 g, 16.4 mmol) dissolved in 80 ml of the same solvent. The reaction mixture was stirred 8 h, diluted with ethyl acetate (1 vol), washed with water, saturated NaHCO3 solution, and brine. Concentration gave a solid which was recrystallized from acetonitrile 5.7 g (86%); mp 217–219° C.; IR(KBr, υ=cm$^{-1}$) 3410, 3286, 1704, 1670, 1500, 1338, 1238, 1104; $^1$H NMR (300 MHz, DMSO-d$_6$) δ 2.15 (3H, s), 3.88 (3H, s), 6.88 (2H, d, J=8.5 Hz), 7.49 (2H, d, J=8.5 Hz), 7.68 (1H, s), 7.76 (1H, s), 8.61 (1H, br. s), 9.62 (1H, br. s) 10.01 (1H, br. s); MS(ESI)m/z: 400 (M−H$^-$); Anal. calcd. for $C_{17}H_{15}ClF_3N_3O_3$: C, 50.82; H, 3.76; N, 10.46. Found: C, 50.68; H, 3.79; N, 10.45.

The following hydrazides were prepared using the procedure of Example 123.

EXAMPLE 124

4-(Acetylamino)-5-chloro-2-methoxybenzoic acid, phenylhydrazide
(Y=NHAc, R$_1$=R$_2$=H)
mp 180–181 ° C.; Anal. calcd. for $C_{16}H_{16}ClN_3O_3$: C, 57.58; H, 4.83; N, 12.59. Found: C, 57.44; H, 4.77; N, 12.72.

EXAMPLE 125

5-Chloro-2-methoxybenzoic acid, 2-[4-(trifluoromethyl)phenyl]hydrazide
(Y=H, R$_1$=CF3, R$_2$=H)
mp 183.5–184.5° C.; Anal. calcd. for $C_{15}H_{12}ClF_3N_2O_2$: C, 52.27; H, 3.51; N, 8.13. Found: C, 52.17; H, 3.53; N, 8.08.

EXAMPLES 126–130

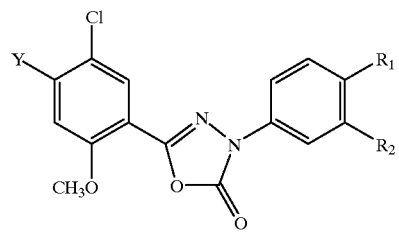

XXVI$^{126-130}$

EXAMPLE 126

N-[2-Chloro-4-[2,3-dihydro-2-oxo-3-[4-(trifluoromethyl)phenyl]-1,3,4-oxadiazol-5-yl]-5-methoxyphenyl]acetamide
(XXVI$^{126}$: Y=NHAc, R$_1$=CF3, R$_2$=H)
4-(Acetylamino)-5-chloro-2-methoxybenzoic acid, 4-(trifluoromethyl) phenylhydrazide (5.7 g, 14.2 mmol) was dissolved in THF (500 ml) under $N_2$. and 1,1'-carbonyldiimidazole (2.3 g, 14.2 mmol) and triethylamine (1.5 ml, 14.2 mmol) added. The solution was stirred for 18 h at 24° C. before solvent was removed by rotary evaporation. The residue was taken up in ethyl acetate (400 ml) and washed with 0.1N HCl solution (100 ml), water (100 ml) and brine prior to drying over MgSO$_4$. Recrystallization from acetonitrile gave 3.3 g (55%); mp 235–236° C. IR(KBr, υ=cm$^{-1}$) 3348, 1772, 1690, 1334, 1234, 1116; $^1$H NMR (300 MHz, DMSO-d$_6$) δ 2.18 (3H, s), 3.89 (3H, s), 7.51 (1H, s), 7.79–7.93 (3H, m), 8.05 (2H, d, J=8.5 Hz), 9.67 (1H, br. s); MS(ESI)m/z: 426 (M−H$^-$); Anal. calcd. for $C_{18}H_{13}ClF_3N_3O_4$: C, 50.54; H, 3.06; N, 9.82. Found: C, 50.43; H, 3.01; N, 9.88.

The following oxadiazolones were prepared in a fashion similar to that of Example 126.

EXAMPLE 127

N-[2-Chloro-4-[2,3-dihydro-2-oxo-3-phenyl]-1,3,4-oxadiazol-5-yl]-5-methoxyphenyl]acetamide (XXVI[127]: Y=NHAc, $R_1=R_2=H$)

mp 216–217° C.; Anal. calcd. for $C_{17}H_{14}ClN_3O_4$: C, 56.76; H,3.92; N, 11.68. Found: C, 56.52; H, 3.76; N, 11.81.

EXAMPLE 128

5-(5-Chloro-2-methoxyphenyl)-3-[4-(trifluoromethyl)phenyl]-1,3,4-oxadiazol-2(3H)-one (XXVI[128]: Y=H, $R_1$=CF3, $R_2$=H)

mp 126.5–128° C.; Anal. calcd. for $C_{16}H_{10}ClF_3N_2O_3$: C, 51.84; H, 2.72; N, 7.56. Found: C, 51.69; H, 2.77; N, 7.53.

The following anilines were by hydrolysis of the acetate according to the procedure described in Example 68.

EXAMPLE 129

5-(4-Amino-5-chloro-2-methoxyphenyl)-3-phenyl-1,3,4-oxadiazol-2(3H)-one (XXVI[129]: Y=NH$_2$, $R_1=R_2=H$)

mp 193–195° C.; Anal. calcd. for $C_{15}H_{12}ClN_3O_3$: C, 56.70; H, 3.81; N, 13.23. Found: C,56.44; H, 3.91; N, 12.30.

EXAMPLE 130

5-(4-Amino-5-chloro-2-methoxyphenyl)-3-[3,4-dichlorophenyl]-1,3,4-oxadiazol-2(3H)-one (XXVI[130]: Y=NH$_2$, $R_1=R_2$=Cl)

mp 220–221° C.; Anal. calcd. for $C_{15}H_{10}Cl_3N_3O_3$: C, 46.60; H, 2.61; N, 10.87. Found: C, 46.31; H, 2.57; N, 10.65.

The following phenols were prepared according to the BBr$_3$ method of Example 78.

EXAMPLES 131–134

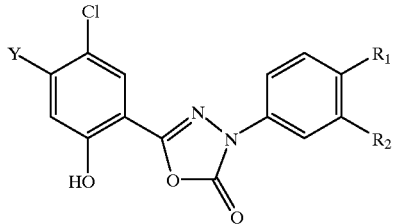

XXVI[131-134]

EXAMPLE 131

5-(4-Amino-5-chloro-2-hydroxyphenyl)-3-[4-(trifluoromethyl)phenyl]-1,3,4-oxadiazole-2-(3H)-one (XXVI[131]: Y=NH$_2$, $R_1$=CF$_3$, $R_2$=H)

mp 266–268° C.; Anal. calcd. for $C_{15}H_9ClF_3N_3O_3$: C, 48.47; H, 2,44; N, 11,30. Found: C, 48.37; H, 2.38; N, 11.42.

EXAMPLE 132

5-($_4$-Amino-5-chloro-2-hydroxyphenyl)-3-phenyl-1,3,4-oxadiazole-2-(3H)-one (XXVI[132]: Y=NH$_2$, $R_1=R_2=H$)

mp 280–282° C.; Anal. calcd. for $C_{14}H_{10}ClN_3O_3$: C, 55.37; H, 3.32; N, 13.84. Found: C, 55.13; H, 3.38; N, 13.74.

EXAMPLE 133

5-(5-Chloro-$_2$-hydroxyphenyl)-3-[4-(trifluoromethyl)phenyl]-1,3,4-oxadiazol-2(3H)-one (XXVI[133]: Y=H, $R_1$=CF3, $R_2$=H)

mp 214–215° C.; Anal. calcd. for $C_{15}H_8ClF_3N2O_3$: C, 50.51; H, 2.26; N, 7.85. Found: C, 50.07; H, 2.1 1; N, 7.96.

EXAMPLE 134

5-(4-Amino-5-cloro-2-hydroyphenyl)-3-[3,4-dichlorophenyl]1,3,4-oxadiazole-2-(3H)-one (XXVI[134]: Y=NH$_2$, $R_1=R_2$=Cl)

mp>300° C.; Anal. calcd. for $C_{14}H_8Cl_3N_3O_3$: C, 45.13; H, 2.16; N, 11.28. Found: C, 45.26; H, 2.12; N, 11.13.

Preparation No. 8

EXAMPLE 135 a-Oxo4-(trifluoromethyl)benzeneacetic acid. 2-(5-chloro-2-methoxyphenyl) hydrazone (XXVI[135]: $R_1=R_3=R_4=H$, $R_2=CF_3$)

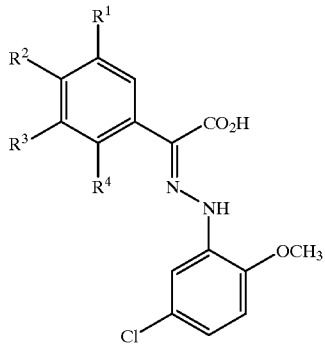

XXVII[135]

A solution of 4-bromobenzotrifluoride (22.5 g, 0.1 mol) in anhydrous diethylether (30 ml) was added dropwise to a stirred suspension of magnesium turnings (3.65 g, 0.15 mol) activated with catalytic amount of dibromoethane (0.5 ml) in ether (30 ml) over 30 min.

The mixture was heated at reflux for 2 h, allowed to cool, and added dropwise over 30 min to a cold (−78° C.) stirred solution of dry diethyl oxalate (14.6 g, 0.1 mol) in 50 ml of the same solvent. The resultant mixture was warmed to −20° C. over 1 h and maintained at +20° C. for 1 hr before being acidified by slow addition of 1 N HCl. The organic layer was washed with saturated NaHCO$_3$ solution, brine, and dried over Na$_2$SO$_4$.

Concentration followed by vacuum distillation gave a liquid 22.1 g (90%): bp 88–90° C. 0.75 torr.

The oxalate (12.3 g, 0.05 mol) was hydrolyzed upon being stirred with 3N NaOH (50 mL) in THF (50 mL) while being heated at feflux for 6 hr. The THF was removed by rotary evaporation, and the aqueous residue was cooled (0° C.) and acidified with 6N HCl. Extraction with EtOAc, wash with brine, and dry (Na$_2$SO$_4$) afforded [4-(trifluoromethyl)-phenyl]glyoxylic acid as a golden oil which upon standing under vacuum solidified to a light yellow solid (10.2 g, 93%): mp 63–65° C.

Neat 5-chloro-2-methoxyphenylhydrazine (1.73 g, 10 mmol) was added portionwise to a stirred solution of [4-

(trifluoromethyl)phenyl]-glyoxylic acid (2.18 g, 10 mmol) in absolute ethanol and the resultant bright yellow suspension was stirred at room temperature for 30 min before heating at reflux for an addtional 30 min. Solvent was removed by rotary evaporation and the product recrystallized from EtOAc-hexanes to afford the desired hydrazone carboxylic acid (3.57 g, 96%): mp 210–212° C.; IR (KBr, cm$^{-1}$) 3300-2300, 1660, 1230, 1160, 1116; $^1$H NMR (300 MHz, DMSO-d$_6$) d 3.91 (3 H, s), 6.98 (1H, m), 7.10 (1H, d, J=8.7 Hz), 7.44 (1H, d, J=2.5 Hz), 7.75 (2 H, d, J=8.1 Hz), 7.92 (2 H, d, J=8.1 Hz), 12.62 (1H, brd s); MS m/e 371 (M-H)$^-$.

EXAMPLE 136–138

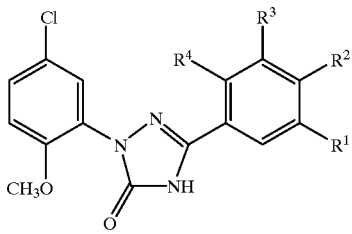

XXVIII$^{136-138}$

EXAMPLE 136

2-(5-Chloro-2-methoxyphenyl)-2,4-dihydro-5-[4-(trifluoromethyl)phenyl]-1,2,4(3H)-triazol-3-one (XXVIII$^{136}$: $R_1=R_3=R_4=H$, $R_2=CF_3$)

Diphenylphosphoryl azide (1.51 g, 5.5 mmol) was added to a stirred solution of α-oxo-4-(trifluoromethyl) benzeneacetic acid, 2-(5-chloro-2-methoxy-phenyl) hydrazone (1.86 g, 5 mmol) and triethylamine (0.77 mL, 5.5 mmol) in dry toluene (60 mL). The resultant yellow solution was heated at reflux for 3 h, diluted with ethyl acetate, and poured into saturated NaHCO$_3$ solution (100 mL) with vigorous stirring. After separation of the organic layer, the aqueous phase was further extracted with ethyl acetate and the combined organic extracts were washed with water, brine, and dried (Na$_2$SO$_4$). Evaporation of the solvents followed by trituration with warm ether gave a white solid 1.69 g (91%): mp 251–253° C.; IR (KBr, cm$^{-1}$) 2900, 1700, 1330, 1290, 1130; $^1$H NMR (300 MHz, DMSO-d$_6$) δ 3.79 (3H, s), 7.23 (1H, dd, J=8.1, 1.2 Hz), 7.51 (1H, d, J=8.1 Hz), 7.53 (1H, d, J=1.2 Hz), 7.88 (2H, d, J=8.2 Hz), 12.6 (1H, br s); MS (DCl)m/z: 370 (MH$^+$). Anal. calcd. for C$_{16}$H$_{11}$ClF$_3$N$_3$O$_2$.0.17H$_2$O: C, 51.55; H, 3.06; N, 11.27. Found: C, 51.54; H, 2.94; N, 11.07.

The compounds of the following Examples were prepared according to the method in Example 136.

EXAMPLE 137

2-(5-Chloro-2-methoxyphenyl)-2,4-dihydro-5-[3-(trifluoromethyl)phenyl]-1,2,4-(3H)-triazol-3-one (XXVIII$^{137}$: $R_1=CF_3$, $R_2=R_3=R_4=H$)

mp 240–243° C.; Anal. calcd. for C$_{16}$H$_{11}$ClF$_3$N$_3$O$_2$: C, 51.98 H, 3.00; N, 11,37. Found: C, 51.89; H, 3.02; N, 11.43.

EXAMPLE 138

2-(5-Chloro-2-methoxyphenyl)-2,4-dihydro-5-[3,5-bis(trifluoromethyl)phenyl]-1,2,4(3H)-triazol-3-one (XXVIII$^{138}$: $R_1=R_3=CF_3$, $R_2=R_4=H$)

mp 227–230° C.; Anal. calcd. for C$_{17}$H$_{10}$ClF$_6$N$_3$O$_2$: C, 46.65 H, 2.30; N, 9.60. Found: C, 46.82; H, 2.23; N, 9.55.

EXAMPLE 139

5-[5-Chloro-2-methoxyphenyl]-2,4-dihydro-2-[4-(trifluoromethyl)phenyl]-1,2,4(3H)-triazol-3-one (XXIX$^{139}$)

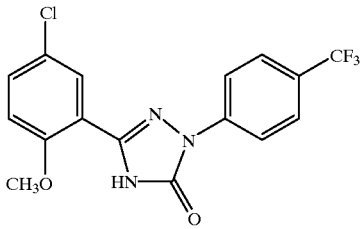

XXIX$^{139}$ mp 265.5–267.5° C.; Anal. calcd. for C$_{16}$H$_{11}$ClF$_3$N$_3$O$_2$: C, 51.97; H, 3.00; N, 11,37. Found: C, 51.90; H, 2.96; N, 11.43.

The following phenols were prepared according to the BBr$_3$ method of Example 78.

EXAMPLES 140–145

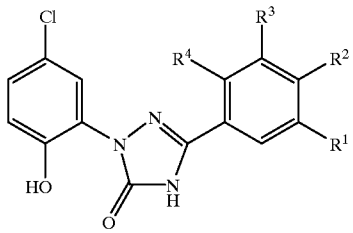

XXVIII$^{140-145}$

EXAMPLE 140

2-(5-Chloro-2-hydroxyphenyl)-2,4-dihydro-5-[4-(trifluoromethyl)phenyl]-1,2,4(3H)-triazol-3-one (XXVIII$^{140}$: $R_1=R_3=R_4=H$, $R_2=CF_3$)

mp 252–255° C.; Anal. calcd. for C$_{15}$H$_9$ClF$_3$N$_3$O$_2$.0.1 H$_2$O: C, 50.40; H, 2.59; N, 11.75. Found: C, 50.39; H, 2,46; N, 11.63.

EXAMPLE 141

2-(5-Chloro-2-hydroxyphenyl)-2,4-dihydro-5-[3-(trifluoromethyl)phenyl]-1,2,4(3H)-triazol-3-one (XXVIII$^{141}$: $R_1=CF_3$, $R_2=R_3=R_4=H$)

mp 240–245° C.; Anal. calcd. for C$_{15}$H$_9$ClF$_3$N$_3$O$_2$: C, 50.65; H, 2.55; N, 11.81. Found: C, 50.21; H, 2.50; N, 11.62.

EXAMPLE 142

2-(5-Chloro-2-hydroxyphenyl)-2,4-dihydro-5-[2-(trifluoromethyl)phenyl]-1,2,4(3H)-triazol-3-one (XXVIII$^{142}$: $R_4=CF_3$, $R_1=R_2=R_3=H$)

mp 167–170° C.; Anal. calcd. for C$_{15}$H$_9$ClF$_3$N$_3$O$_2$.0.78H$_2$O: C, 48.72; H, 2.87; N, 11,36. Found: C, 48.73; H, 2.51; N, 11,32.

EXAMPLE 143

2-(5-Chloro-2-hydroxyphenyl)-2,4-dihydro-5-[3,5-bis(trifluoromethyl)phenyl]-1,2,4(3H)-triazol-3-one (XXVIII$^{143}$: $R_1=R_3=CF_3$, $R_2=R_4=H$)

mp 250–253° C.; Anal. calcd. for $C_{16}H_8ClF_6N_3O_2 \cdot 0.5H_2O$: C, 44.41; H, 2.10; N, 9.71. Found: C, 44.62; H, 2.04; N, 9.61.

EXAMPLE 144

2-(5-Chloro-2-hydroxyphenyl)-2,4-dihydro-5-[2,4-bis(trifluoromethyl)phenyl]-1,2,4(3H)-triazol-3-one ($XXVIII^{144}$: $R_1=R_3=H$, $R_2=R_4=CF_3$)

mp 270–275° C.; Anal. calcd. for $C_{16}H_8ClF_6N_3O_2 \cdot 1 H_2O \cdot 0.25\, CH_2Cl_2$: C, 42.16; H, 2.28; N, 9.08. Found: C, 41.82; H, 2.18; N, 8.91.

EXAMPLE 145

2-(5-Chloro-2-hydroxyphenyl)-2,4-dihydro-5-[3-chloro-4-(trifluoromethyl)phenyl]-1,2,4(3H)-triazol-3-one ($XXVIII^{145}$: $R_1=Cl$, $R_2=CF_3$, $R_3=R_4=H$)

mp 220–224° C.; Anal. calcd. for $C_{15}H_8Cl_2F_3N_3O_2$: C, 46.18; H, 2.07; N, 10.77. Found: C, 45.99; H, 2.07; N, 10.54.

EXAMPLE 146

5-[5-Chloro-2-hydroxyphenyl]-2,4-dihydro-2-[4-(trifluoromethyl)phenyl]-1,2,4(3H)-triazol-3-one ($XXIX^{146}$)

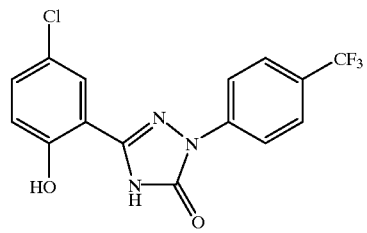

$XXIX^{146}$ mp >305° C.; Anal. calcd. for $C_{15}H_9ClF_6N_3O_2$: C, 50.65; H, 2.55; N, 11.81. Found: C, 50.66; H, 2.67; N, 11.73.

Reasonable variations, such as those which would occur to a skilled artisan, can be made herein without departing from the scope of the invention.

We claim:

1. A compound of the Formula (1)

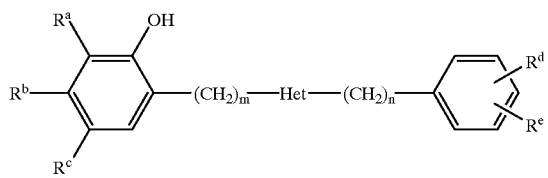

(1)

wherein "Het" is a moiety selected from the group consisting of (B),(D),(E) and (H)

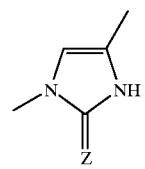
(B)

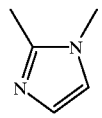
(D)

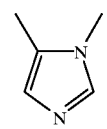
(E)

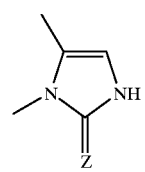
(H)

wherein

Z is independently for each occurrence selected from O or S; $R^a$, $R^b$ and $R^c$ each are independently selected from hydrogen, halogen, OH, $CF_3$, $NO_2$, or

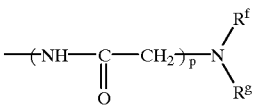

provided $R^c$ is not hydrogen; and when $R^a$ and $R^b$ are hydrogen, $R^c$ may be a heterocyclic moiety selected from the group consisting of imidazol-1-yl, morpholinomethyl, N-methylimidazol-2-yl, and pyridin-2-yl;

$R^d$ and $R^e$ each are independently selected from hydrogen, halogen, $CF_3$, $NO_2$ or imidazol-1-yl;

m,n and p each are independently selected from an integer of 0 or 1; and $R^f$ and $R^g$ each are independently hydrogen; $C_{1-4}$ alkyl; or $R^f$ and $R^g$, taken together with the nitrogen atom to which they are attached, is a heterocyclic moiety selected from the group consisting of N-methylpiperazine, morpholine, thiomorpholine, N-benzylpiperazine and imidazolinone;

or a nontoxic pharmaceutically acceptable salt or solvate thereof.

2. A compound of claim 1 in which "Het" is an imidazole moeity of group (D) or (E), and m=n=0.

3. A compound of claim 2 selected from the group consisting of:

4-Chloro-2-[2-[4-(trifluoromethyl)phenyl]-1H-imidazol-1-yl]phenol;

4-Chloro-2-[1-[4-(trifluoromethyl)phenyl]-1H-imidazol-2-yl]phenol;

4-Chloro-2-[1-phenyl-1H-imidazol-2-yl]phenol; and 1-(5-chloro-2-hydroxyphenyl)-5-[4-(trifluoromethyl)phenyl]-1H-imidazole.

4. The compound of claim 1 which is 1-(5-chloro-2-hydroxyphenyl)-1,3-dihydro-5-phenyl-2H-imidazol-2-one.

5. A pharmaceutical composition for the treatment of disorders responsive to openers of the large conductance calcium-activated potassium channels comprising a therapeutically effective amount of a compound as defined in claim 1 in association with a pharmaceutically acceptable carrier or diluent.

6. A method for the treatment of disorders responsive to opening of the large conductance calcium-activated potassium channels in a mammal in need thereof, which comprises administering to said mammal a therapeutically effective amount of a compound as defined in claim 1.

7. A method of claim 6 wherein said disorder is ischemia, convulsions, asthma, irritable bowel syndrome, migraine, traumatic brain injury, male erectile dysfunction and urinary incontinence.

8. The method of claim 7 wherein the disorder is cerebral ischemia.

* * * * *